United States Patent
Darteil et al.

(10) Patent No.: US 7,253,296 B2
(45) Date of Patent: Aug. 7, 2007

(54) ACYLATED AMINOPROPANEDIOLS AND ANALOGUES AND THERAPEUTIC USES THEREOF

(75) Inventors: Raphaël Darteil, Lille (FR); Karine Caumont-Bertrand, Frelinghien (FR); Jamila Najib, Santes (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 10/541,225

(22) PCT Filed: Feb. 12, 2004

(86) PCT No.: PCT/FR2004/000319

§ 371 (c)(1),
(2), (4) Date: Jul. 1, 2005

(87) PCT Pub. No.: WO2004/074239

PCT Pub. Date: Sep. 2, 2004

(65) Prior Publication Data

US 2006/0069156 A1    Mar. 30, 2006

(30) Foreign Application Priority Data

Feb. 12, 2003 (FR) ................... 03 01688

(51) Int. Cl.
*C07C 55/22* (2006.01)
*A61K 31/195* (2006.01)

(52) U.S. Cl. .................. 554/101; 554/85; 554/102; 554/110; 554/111; 554/127; 560/25; 560/129; 560/147; 560/196; 514/513; 514/547; 514/562

(58) Field of Classification Search .............. 560/25, 560/129, 147, 196; 554/102, 110, 111, 127, 554/85, 101; 514/513, 547, 562
See application file for complete search history.

(56) References Cited

FOREIGN PATENT DOCUMENTS

| JP | 2000-169443 | 6/2000 |
|---|---|---|
| WO | 99/10321 | 3/1999 |

OTHER PUBLICATIONS

Witten et al, Cancer, vol. 15, pp. 1041-1055, 1962.*
International Search Report of PCT/FR2004/000319, mailed Aug. 10, 2004.
Database WPI, Section Ch, Week 200036, Derwent Publications Ltd., AN 2000-328909, XP0002257696.
M.D. Rahman et al., "Effects of sulphur-containing analogues of stearic acid on growth and fatty acid biosynthesis in the protozoan crithidia-fasciculata", Journal of Medicinal Chemistry, vol. 31, No. 8, Aug. 1988, pp. 1656-1659, XP002257466, American Chemical Society.

* cited by examiner

*Primary Examiner*—Shailendra Kumar
(74) *Attorney, Agent, or Firm*—Nixon & Vanderhye P.C.

(57) ABSTRACT

The invention relates to novel acylated aminopropanediols and the nitrogen and sulfur analogues thereof, pharmaceutical compositions comprising same, therapeutic uses thereof, in particular for the treatment of cerebral ischemia. The invention also provides a method of preparing said derivatives.

33 Claims, 3 Drawing Sheets

ACYLATED AMINOPROPANEDIOLS AND ANALOGUES AND THERAPEUTIC USES THEREOF

This application is the US national phase of international application PCT/FR2004/000319, filed 12 Feb. 2004, which designated the U.S. and claims priority of FR 03/01688, filed 12 Feb. 2003, the entire contents of each of which are hereby incorporated by reference.

The invention relates to novel acylated aminopropanediols and the nitrogen and sulfur analogues thereof, pharmaceutical compositions comprising same, therapeutic uses thereof, in particular for the treatment of cerebral ischemia. The invention also provides a method of preparing said derivatives.

The inventive compounds have advantageous antioxidant and anti-inflammatory pharmacological properties. The invention also describes methods of therapeutic treatment using said compounds and pharmaceutical compositions comprising same. In particular, the inventive compounds are useful for preventing or treating stroke.

In France, cerebrovascular disease (150,000 new cases annually) is the third leading cause of mortality and the leading cause of disability in adults. Ischemic and hemorrhagic stroke respectively account for 80% and 20% of all cerebrovascular accidents. Ischemic stroke is an important therapeutic issue that must be addressed in order to reduce the morbidity and mortality of cerebrovascular disease. Progress has been made not only in treating the acute phase of ischemia but also in preventing same. It is therefore important to keep in mind that the identification and management of risk factors are essential in the treatment of this pathology.

Drug-based treatments of cerebral ischemia are based on different strategies. A first strategy comprises preventing the occurrence of cerebral ischemic accidents through prevention of risk factors (hypertension, hypercholesterolemia, diabetes, atrial fibrillation, etc.) or through prevention of thrombosis, in particular with the help of antiplatelet drugs or anticoagulants (Adams 2002) and (Gorelick 2002).

A second strategy comprises treating the acute phase of ischemia, so as to attenuate its long-term consequences (Lutsep and Clark 2001).

The pathophysiology of cerebral ischemia can be described as follows: the ischemic penumbra, an intermediate zone between the ischemic focus where the neurons are necrotized and the intact nerve tissue, is the site of a pathophysiological cascade which leads over the course of a few days to neuronal death, if reperfusion does not occur or if neuroprotection is insufficient. The first event, which takes place in the first few hours, is a massive release of glutamate which leads to neuron depolarization and cellular oedema. Calcium influx into the cell induces mitochondrial damage leading to the release of free radicals and the induction of enzymes that promote degradation of neuronal membranes. Calcium influx into the cell induces mitochondrial damage leading to the release of free radicals and the induction of enzymes that promote degradation of neuronal membranes. Calcium influx and free radical production in turn activate certain transcription factors, such as NF-κB. Said activation induces inflammatory processes such as induction of endothelial adhesion proteins, polynuclear neutrophil infiltration of the ischemic focus, microglial activation, induction of enzymes like nitric oxide (NO) synthase type II or cyclooxygenase type II. These inflammatory processes lead to release of NO or prostanoids which are toxic to the cell. Together, these processes result in a phenomenon of apoptosis inducing irreversible lesions (Dirnagl, Iadecola et al. 1999).

The concept of prophylactic neuroprotection is based on experimental data in animal models demonstrating ischemic tolerance. In fact, different procedures applied prior to experimentally induced brain ischemia attenuate the severity of the latter. Various stimuli can induce brain ischemic tolerance: preconditioning (brief ischemia preceding prolonged ischemia); heat stress; administration of a low dose of bacterial lipopolysaccharide (Bordet, Deplanque et al. 2000).

Said stimuli induce tolerance mechanisms which activate signals triggering protective mechanisms. Different triggering mechanisms have been identified: cytokines, inflammatory pathways, free radicals, NO, ATP-dependent potassium channels, adenosine. The observed lag time between the onset of early events and ischemic tolerance stems from the need for protein synthesis. Various types of proteins have been shown to induce ischemic tolerance: heat shock proteins, antioxidant enzymes and anti-apoptotic proteins (Nandagopal, Dawson et al. 2001).

Thus there is a real need for compounds capable of preventing the development of risk factors for cerebrovascular accidents such as atherosclerosis, diabetes, obesity, and the like, capable of providing prophylactic neuroprotection but also active neuroprotection in the acute phase of cerebral ischemia.

The PPARs ($\alpha$, $\beta$, $\gamma$) belong to the hormone-activated nuclear receptor family. When activated by binding with their ligand, they heterodimerize with Retinoid-X-Receptor (RXR) and bind to "Peroxisome Proliferator Response Elements" (PPREs) located in the promoter sequence of target genes. Binding of PPAR to PPRE thereby induces expression of the target gene (Fruchart, Staels et al. 2001).

The PPARs are distributed in a wide variety of organs, although they all exhibit a certain degree of tissue specificity with the exception of PPARβ the expression of which appears to be ubiquitous. PPARα expression is particularly high in liver and in the intestinal lumen whereas PPARγ is expressed mainly in fat tissue and spleen. The three subtypes ($\alpha$, $\beta$, $\gamma$) are expressed in the central nervous system. Cells such as oligodendrocytes and astrocytes more particularly express the PPARα subtype (Kainu, Wikstrom et al. 1994).

The target genes of PPARs control lipid and glucose metabolism. However, recent discoveries suggest that the PPARs participate in other biological processes. PPAR activation by their ligands induces changes in the transcriptional activity of genes which modulate the inflammatory process, antioxidant enzymes, angiogenesis, cell proliferation and differentiation, apoptosis, the activities of iNOS, MMPases and TIMPs (Smith, Dipreta et al. 2001) and (Clark 2002).

Free radicals play a role in a very wide range of pathologies including allergy, tumor initiation and promotion, cardiovascular diseases (atherosclerosis, ischemia), genetic and metabolic disorders (diabetes), infectious and degenerative diseases (prion, etc.) and in ophthalmic disorders (Mates, Perez-Gomez et al. 1999).

Reactive oxygen species (ROS) are produced during normal cell functioning. ROS comprise the hydroxyl radical (OH]), superoxide anion ($O_2^-$), hydrogen peroxide ($H_2O_2$) and nitric oxide (NO). Said species are very labile and, due to their high chemical reactivity, constitute a danger to the biological functions of cells. They induce lipid peroxidation, oxidation of certain enzymes and very extensive oxidation of proteins leading to degradation thereof. Protection against lipid peroxidation is a vital process in aerobic organisms, because peroxidation products can cause DNA damage.

Thus a deregulation or modification of the equilibrium between the production, processing and elimination of radical species by natural antioxidant defenses leads to the establishment of processes that are deleterious to the cell or organism.

ROS are processed via an antioxidant system that comprises an enzymatic component and a non-enzymatic component. The enzymatic system is composed of several enzymes which have the following characteristics:

Superoxide dismutase (SOD) destroys the superoxide radical by converting it to peroxide. The peroxide in turn is acted upon by another enzyme system. Low levels of SOD are continuously produced by aerobic respiration. Three classes of SOD have been identified in humans, each containing Cu, Zn, Fe, Mn, or Ni as cofactor. The three forms of human SOD are distributed as follows: a cytosolic Cu—Zn SOD, a mitochondrial Mn—SO and an extracellular SOD.

Catalase is very efficient at converting hydrogen peroxide ($H_2O_2$) to water and oxygen. Hydrogen peroxide is enzymatically catabolized in aerobic organisms. Catalase also catalyzes the reduction of a variety of hydroperoxides (ROOH).

Glutathione peroxidase uses selenium as cofactor and catalyzes the reduction of hydroperoxides (ROOH and $H_2O_2$) by using glutathione, and thereby protects cells against oxidative damage.

Non-enzymatic antioxidant defenses of cells comprise molecules which are synthesized or supplied in the diet.

Antioxidant molecules are present in different cell compartments. Detoxification enzymes for example eliminate free radicals and are essential to cell life. The three most important types of antioxidant compounds are the carotenoids, vitamin C and vitamin E (Gilgun-Sherki, Melamed et al. 2001).

To avoid the phenomenon of apoptosis induced by cerebral ischemia and its resultant effects, the inventors have developed novel compounds capable of preventing the development of the risk factors described earlier and capable of exerting a prophylactic neuroprotective activity, but also of providing active neuroprotection during the acute phase of cerebral ischemia.

The inventors have also shown that the compounds according to the invention concurrently display PPAR activator, antioxidant and anti-inflammatory properties and, as such, said compounds have an important therapeutic or prophylactic potential in cerebral ischemia.

The present invention thus provides a novel family of compounds exhibiting advantageous pharmacological properties useful for the preventive or curative treatment of cerebral ischemia. The invention also provides for methods for preparing said derivatives.

The compounds of the invention are represented by general formula (I):

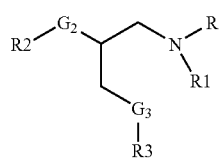

in which:

G2 and G3 independently represent an oxygen atom, a sulfur atom or N—R4 group, G2 and G3 not simultaneously representing a N—R4 group, R and R4 independently represent a hydrogen atom or a linear or branched alkyl group, saturated or not, optionally substituted, containing from 1 to 5 carbon atoms, R1, R2 and R3, which are the same or different, represent a hydrogen atom, a CO—R5 group or a group corresponding to the formula CO—$(CH_2)_{2n+1}$—X—R6, at least one of the groups R1, R2 or R3 being a group corresponding to the formula CO—$(CH_2)_{2n+1}$—X—R6, R5 is a linear or branched alkyl group, saturated or not, optionally substituted, possibly comprising a cyclic group, the main chain of which contains from 1 to 25 carbon atoms, X is a sulfur atom, a selenium atom, a SO group or a $SO_2$ group, n is a whole number comprised between 0 and 11, R6 is a linear or branched alkyl group, saturated or not, optionally substituted, possibly comprising a cyclic group, the main chain of which contains from 3 to 23 carbon atoms, preferably 10 to 23 carbon atoms and optionally one or more heterogroups selected in the group consisting of an oxygen atom, a sulfur atom, a selenium atom, a SO group and $SO_2$ group, with the exception of compounds having formula (I) in which G2R2 and G3R3 simultaneously represent hydroxyl groups.

In compounds represented by general formula (I) according to the invention, the R5 group or groups, which are the same or different, preferably represent a linear or branched alkyl group, saturated or unsaturated, substituted or not, the main chain of which contains from 1 to 20 carbon atoms, even more preferably 7 to 17 carbon atoms, still more preferably 14 to 17. In compounds represented by general formula (I) according to the invention, the R5 group or groups, which are the same or different, can also represent a lower alkyl group containing 1 to 6 carbon atoms, such as in particular the methyl, ethyl, propyl, isopropyl, butyl, isobutyl, pentyl or hexyl group.

In compounds represented by general formula (I) according to the invention, the R6 group or groups, which are the same or different, preferably represent a linear or branched alkyl group, saturated or unsaturated, substituted or not, the main chain of which contains from 3 to 23 carbon atoms, preferably 13 to 20 carbon atoms, even more preferably 14 to 17 carbon atoms, and still more preferably 14 carbon atoms.

Specific examples of saturated long chain alkyl groups for R5 or R6 are in particular the groups $C_7H_{15}$, $C_{10}H_{21}$, $C_{11}H_{23}$, $C_{13}H_{27}$, $C_{14}H_{29}$, $C_{15}H_{31}$, $C_{16}H_{33}$, $C_{17}H_{35}$. Specific examples of unsaturated long chain alkyl groups for R5 or R6 are in particular the groups $C_{14}H_{27}$, $C_{14}H_{25}$, $C_{15}H_{29}$, $C_{17}H_{29}$, $C_{17}H_{31}$, $C_{17}H_{33}$, $C_{19}H_{29}$, $C_{19}H_{31}$, $C_{21}H_{31}$, $C_{21}H_{35}$, $C_{21}H_{37}$, $C_{21}H_{39}$, $C_{23}H_{45}$ or the alkyl chains of eicosapentanoic (EPA) $C_{20:5}$ (5, 8, 11, 14, 17) and docosahexanoic (DHA) $C_{22:6}$ (4, 7, 10, 13, 16, 19) acids.

Examples of branched long chain alkyl groups are in particular the groups $(CH_2)_n$—$CH(CH_3)C_2H_5$, $(CH=C(CH_3)$—$(CH_2)_2)_{n'}$—$CH=C(CH_3)_2$ or $(CH_2)_{2x+1}$—$C(CH_3)_2$—$(CH_2)_{n'''}$—$CH_3$ (x being a whole number equal to or comprised between 1 and 11, n' being a whole number equal to or comprised between 1 and 22, n'' being a whole number equal to or comprised between 1 and 5, n''' being a whole number equal to or comprised between 0 and 22, and (2x+n''') being less than or equal to 22, preferably less than or equal to 20).

As indicated earlier, the alkyl groups R5 or R6 can optionally comprise a cyclic group. Examples of cyclic groups are in particular cyclopropyl, cyclobutyl, cyclopentyl and cyclohexyl.

As indicated earlier, the alkyl groups R5 or R6 can optionally be substituted by one or more substituents, which are the same or different. The substituents are preferably selected in the group consisting of a halogen atom (iodine, chlorine, fluorine, bromine) and a —OH, =O, —$NO_2$, —$NH_2$, —CN, —O—$CH_3$, —$CH_2$—OH, —$CH_2OCH_3$, —$CF_3$ and —COOZ group (Z being a hydrogen atom or an alkyl group, preferably containing from 1 to 5 carbon atoms).

The invention also concerns the optical and geometrical isomers of said compounds, the racemates, salts, hydrates thereof and the mixtures thereof.

Compounds represented by formula (Ia) are compounds corresponding to formula (I) according to the invention in which a single one of the groups R1, R2 or R3 represents a hydrogen atom.

Compounds represented by formula (Ib) are compounds corresponding to formula (I) according to the invention in which two of the groups R1, R2 or R3 represent a hydrogen atom.

The invention also encompasses the prodrugs of the compounds represented by formula (I) which, after administration to a subject, are converted to compounds represented by formula (I) and/or metabolites of compounds represented by formula (I) which display therapeutic activities, particularly for the treatment of cerebral ischemia, which are similar to compounds represented by formula (I).

Moreover, in the group CO—$(CH_2)_{2n+1}$—X—R6, X most preferably represents a sulfur or selenium atom and advantageously a sulfur atom.

Moreover, in the group CO—$(CH_2)_{2n+1}$—X—R6, n is preferably comprised between 0 and 3, more specifically comprised between 0 and 2 and in particular is equal to 0.

In the compounds represented by general formula (I) according to the invention, R6 can contain one or more heterogroups, preferably 0, 1 or 2, more preferably 0 or 1, selected in the group consisting of an oxygen atom, a sulfur atom, a selenium atom, a SO group or a $SO_2$ group.

A specific example of a CO—$(CH_2)_{2n+1}$—X—R6 group according to the invention is the group CO—$CH_2$—S—$C_{14}H_{29}$.

Preferred compounds in the spirit of the invention are therefore compounds represented by general formula (I) hereinabove in which at least one of the groups R1, R2 and R3 represents a CO—$(CH_2)_{2n+1}$—X—R6 group in which X represents a sulfur or selenium atom and preferably a sulfur atom and/or R6 is a saturated and linear alkyl group containing from 3 to 23 carbon atoms, preferably 13 to 20 carbon atoms, preferably 14 to 17, more preferably 14 to 16, and even more preferably 14 carbon atoms.

Other particular compounds of the invention are those in which at least two of the groups R1, R2 and R3 are CO—$(CH_2)_{2n+1}$—X—R6 groups, which are the same or different, in which X represents a sulfur or selenium atom and preferably a sulfur atom.

Particular compounds according to the invention are those in which G2 represents an oxygen or sulfur atom, and preferably an oxygen atom. In said compounds, R2 advantageously represents a group corresponding to the formula CO—$(CH_2)_{2n+1}$—X—R6 such as defined hereinabove.

Particularly preferred compounds are compounds represented by general formula (I) hereinabove in which:
G3 is a N—R4 group in which R4 is a hydrogen atom or a methyl group, and G2 is an oxygen atom; and/or
R2 represents a CO—$(CH_2)_{2n+1}$—X—R6 group such as defined hereinabove.

Other preferred compounds are compounds represented by general formula (I) hereinabove in which R1, R2 and R3, which are the same or different, preferably the same, represent a CO—$(CH_2)_{2n+1}$—X—R6 group such as defined hereinabove, in which X represents a sulfur or selenium atom and preferably a sulfur atom and/or R6 represents a saturated and linear alkyl group containing from 13 to 17 carbon atoms, preferably 14 to 17, even more preferably 14 carbon atoms, in which n is preferably comprised between 0 and 3, and in particular is equal to 0. More specifically, preferred compounds are compounds represented by general formula (I) in which R1, R2 and R3 represent CO—$CH_2$—S—$C_{14}H_{29}$ groups.

Examples of preferred inventive compounds are given in FIG. 1.

Thus, the invention more particularly has as object the compounds represented by formula (I) selected from among:
1-tetradecylthioacetylamino-2,3-(dipalmitoyloxy)propane;
3-tetradecylthioacetylamino-1,2-(ditetradecylthioacetyloxy)propane;
3-palmitoylamino-1,2-(ditetradecylthioacetyloxy)propane;
1,3-di(tetradecylthioacetylamino)propan-2-ol;
1,3-diamino-2-(tetradecylthioacetyloxy)propane;
1,3-ditetradecylthioacetylamino-2-(tetradecylthioacetyloxy)propane;
1,3-dioleylamino-2-(tetradecylthioacetyloxy)propane;
1,3-ditetradecylthioacetylamino-2-(tetradecylthioacetylthio)propane; and
1-tetradecylthioacetylamino-2,3-di(tetradecylthioacetylthio)propane.

The invention also has as object a pharmaceutical composition comprising, in a pharmaceutically acceptable support, at least one compound represented by general formula (I) such as described hereinabove, including compounds having formula (I) in which the groups G2R2 and G3R3 simultaneously represent hydroxyl groups, possibly in association with another therapeutic agent. Said composition is intended in particular to treat a cerebrovascular disease, such as cerebral ischemia or hemorrhagic stroke.

Another object of the invention thus concerns any pharmaceutical composition comprising in a pharmaceutically acceptable support at least one compound represented by formula (I) such as described hereinabove, including compounds having formula (1) in which the groups G2R2 and G3R3 simultaneously represent hydroxyl groups.

Advantageously it is a pharmaceutical composition for the treatment or prophylaxis of cerebrovascular pathologies and more particularly cerebral ischemia or cerebrovascular accidents. In fact, it was found in a surprising manner that compounds represented by formula (I), including compounds having formula (I) in which the groups G2R2 and G3R3 simultaneously represent hydroxyl groups, concurrently display PPAR activator, antioxidant and anti-inflammatory properties and exhibit prophylactic and curative neuroprotective activity in cerebral ischemia.

The invention also concerns the use of a compound such as defined hereinabove for preparing a pharmaceutical composition intended for implementing a method of treatment or prophylaxis in humans or animals.

The invention further concerns a method for treating cerebrovascular pathologies and more particularly cerebral ischemia, comprising administering to a subject, in particular human, an effective dose of a compound represented by formula (I) or of a pharmaceutical composition such as defined hereinabove, including compounds having general formula (I) in which the groups G2R2 and G3R3 simultaneously represent hydroxyl groups.

Avantageously, the compounds represented by formula (I) which are used are such as defined hereinabove and also comprise 3-(tetradecylthioacetylamino)propane-1,2-diol.

The pharmaceutical compositions according to the invention advantageously comprise one or more pharmaceutically acceptable excipients or vehicles. Examples include pharmaceutically compatible saline, physiologic, isotonic, buffered solutions and the like, known to those skilled in the art. The compositions may contain one or more agents or vehicles selected from among dispersives, solubilizers, stabilizers, surfactants, preservatives, and the like. Agents or vehicles that may be used in the formulations (liquid and/or injectable and/or solid) comprise in particular methylcellulose, hydroxymethylcellulose, carboxymethylcellulose, polysorbate 80, mannitol, gelatin, lactose, vegetable oils, acacia and the like. The compositions may be formulated as injectable suspensions, gels, oils, tablets, suppositories, powders, gelatin capsules, capsules, and the like, possibly by means of pharmaceutical forms or devices allowing sustained and/or delayed release. For this type of formulation, an agent such as cellulose, carbonates or starches is advantageously used.

The compounds or compositions of the invention may be administered in different ways and in different forms. For instance, they may be administered systemically, by the oral route, parentally, by inhalation or by injection, such as for example by the intravenous, intramuscular, subcutaneous, transdermal, intra-arterial route, etc. For injections, the compounds are generally prepared in the form of liquid suspensions, which may be injected through syringes or by infusion, for instance. In this respect, the compounds are generally dissolved in pharmaceutically compatible saline, physiologic, isotonic, buffered solutions and the like, known to those skilled in the art. For instance, the compositions may contain one or more agents or vehicles selected from among dispersives, solubilizers, emulsifiers, stabilizers, surfactants, preservatives, buffers, and the like. Agents or vehicles that may be used in the liquid and/or injectable formulations comprise in particular methylcellulose, hydroxymethylcellulose, carboxymethylcellulose, polysorbate 80, mannitol, gelatin, lactose, vegetable oils, acacia, liposomes, and the like.

The compositions may thus be administered in the form of gels, oils, tablets, suppositories, powders, gelatin capsules, capsules, aerosols, and the like, possibly by means of pharmaceutical forms or devices allowing sustained and/or delayed release. For this type of formulation, an agent such as cellulose, carbonates or starches is advantageously used.

The compounds may be administered orally in which case the agents or vehicles used are preferably selected in the group consisting of water, gelatin, gums, lactose, starch, magnesium stearate, talc, an oil, polyalkylene glycol, and the like.

For parenteral administration, the compounds are preferably administered in the form of solutions, suspensions or emulsions in particular with water, oil or polyalkylene glycols to which, in addition to preservatives, stabilizers, emulsifiers, etc., it is also possible to add salts to adjust osmotic pressure, buffers, and the like.

It is understood that the injection rate and/or injected dose may be adapted by those skilled in the art according to the patient, the pathology, the mode of administration, etc. Typically, the compounds are administered at doses ranging from 1 μg to 2 g per dose, preferably from 0.1 mg to 1 g per dose. The doses may be administered once a day or several times a day, as the case may be. Moreover, the compositions of the invention may also comprise other active substances or agents.

The invention also concerns methods for preparing the hereinabove compounds. The compounds of the invention can be prepared from commercially available products, by employing a combination of chemical reactions known to those skilled in the art.

According to one method of the invention, compounds represented by formula (I) in which (i) G2 and G3 are oxygen or sulfur atoms or a N—R4 group, (ii) R and, as the case may be, R4, represent an identical linear or branched alkyl group, saturated or not, optionally substituted, containing from 1 to 5 carbon atoms and (iii) R1, R2 and R3, which are the same or different, represent a CO—R5 group or a CO—$(CH_2)_{2n+1}$—X—R6 group, are obtained from a compound represented by formula (I) in which (i) G2 or G3 are oxygen or sulfur atoms or a NH group, (ii) R is a hydrogen atom and (iii) R1, R2 and R3, which are the same or different, represent a CO—R5 or CO—$(CH_2)_{2n+1}$—X—R6 group, an a compound corresponding to the formula A1-LG in which A1 represents the group R or, as the case may be, R4 and LG is a reactive group selected for example in the group consisting of Cl, Br, mesyl, tosyl, etc., possibly in the presence of coupling agents or activators known to those skilled in the art.

In a first embodiment, compounds represented by formula (I) in which (i) G2 and G3 are oxygen or sulfur atoms or a NH group, (ii) R is a hydrogen atom and (iii) R1, R2 and R3, which are the same, represent a CO—$(CH_2)_{2n+1}$—X—R6 group, are obtained from a compound represented by formula (I) in which (i) G2 or G3 are oxygen or sulfur atoms or a NH group, (ii) R is a hydrogen atom and (iii) R1, R2 and R3 are hydrogen atoms and a compound corresponding to the formula A°-CO-A in which A is a reactive group selected for example in the group consisting of OH, Cl, O—CO-A° and O—R7, R7 being an alkyl group, and A° is the $(CH_2)_{2n+1}$—X—R6 group, possibly in the presence of coupling agents or activators known to those skilled in the art.

Compounds represented by formula (I) according to the invention in which (i) G2 and G3 are oxygen atoms or a NH group, (ii) R is a hydrogen atom and (iii) R1, R2 and R3 are hydrogen atoms or represent a CO—R5 or CO—$(CH_2)_{2n+1}$—X—R6 group can be obtained by different methods which enable the synthesis of compounds in which the groups carried on a same heteroatom (nitrogen or oxygen) have the same meaning.

According to a first embodiment, a molecule of 1-aminoglycerol, 1,3-diaminoglycerol or 1,2-diaminoglycerol (obtained by adapting the protocol described by (Morris, Atassi et al. 1997)) is reacted with a compound corresponding to the formula A°-CO-A1 in which A1 is a reactive group selected for example in the group consisting of OH, Cl and OR7, R7 being an alkyl group, and A° is the R5 group or the $(CH_2)_{2n+1}$—X—R6, group possibly in the presence of coupling agents or activators known to those skilled in the art. Said reaction respectively yields particular forms of compounds represented by formula (I), named compounds (IIa-c), and can be carried out by adapting the protocols described by (Urakami and Kakeda 1953), (Shealy, Frye et al. 1984), (Marx, Piantadosi et al. 1988) and (Rahman, Ziering et al. 1988) or (Nazih, Cordier et al. 1999). In compounds (IIb-c), the groups carried on a same heteroatom, respectively, (R1 and R3) and (R1 and R2) have the same meaning.

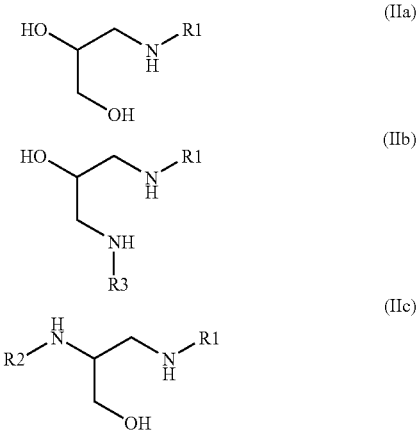

Compounds represented by formula (I) according to the invention in which (i) G2 and G3 are oxygen atoms or a NH group, (ii) R is a hydrogen atom and (iii) R1, R2 and R3, which are the same or different, represent a CO—R5 or CO—(CH$_2$)$_{2n+1}$—X—R6 group, can be obtained from a compound having formula (IIa-c) and a compound corresponding to the formula A°-CO-A2 in which A2 is a reactive group selected for example in the group consisting of OH and Cl, and A° is the R5 group or the (CH$_2$)$_{2n+1}$—X—R6 group, possibly in the presence of coupling agents or activators known to those skilled in the art. Said reaction enables the synthesis of compounds in which the groups carried on a same heteroatom (nitrogen or oxygen), respectively (R1 and R2), (R1 and R3) or (R2 and R3) have the same meaning. Advantageously, said reaction is carried out according to the protocol described for example in (Urakami and Kakeda 1953) and (Nazih, Cordier et al. 1999).

According to another particular method of the invention (diagram 1), compounds represented by formula (I) in which (i) G2 and G3 are oxygen atoms or a NH group (ii) R is a hydrogen atom and (iii) R1, R2 and R3, which are the same or different, represent a CO—R5 or CO—(CH$_2$)$_{2n+1}$—X—R5 group, can be obtained according to the following steps:

a) reacting 1-aminoglycerol, 1,3-diaminoglycerol or 1,2-diaminoglycerol with a compound (PG)$_2$O in which PG is a protective group to give a compound having general formula (IIIa-c). Advantageously, the reaction can be carried out by adapting the protocols described by (Nazih, Cordier et al. 2000) and (Kotsovolou, Chiou et al. 2001) in which (PG)$_2$O represents di-tert-butyl dicarbonate;

b) reacting the compound having formula (IIIa-c) with a compound corresponding to the formula A°-CO-A2 in which A2 is a reactive group selected for example in the group consisting of OH and Cl, and A° is the R5 group or the (CH$_2$)$_{2n+1}$—X—R6 group, possibly in the presence of coupling agents or activators known to those skilled in the art to give a compound represented by general formula (IVa-c), in which R2 and R3 represent a CO—R5 or CO—(CH$_2$)$_{2n+1}$—X—R6 group and PG is a protective group;

c) deprotecting the compound (IVa-c), according to conventional conditions known to those skilled in the art, to give a compound represented by general formula (I) in which (i) G2 and G3 represent an oxygen atom or a NH group, (ii) R and R1 are hydrogen atoms and (iii) R2 and R3 represent a CO—R5 or CO—(CH$_2$)$_{2n+1}$—X—R6 group;

d) reacting a compound represented by general formula (I) in which (i) G2 and G3 represent an oxygen atom or a NH group, (ii) R and R1 are hydrogen atoms and (iii) R2 and R3 represent a CO—R5 or CO—(CH$_2$)$_{2n+1}$—X—R6 group with a compound corresponding to the formula A°-CO-A2 in which A2 is a reactive group selected for example in the group consisting of OH and Cl, and A° is the R5 group or the (CH$_2$)$_{2n+1}$—X—R6 group, possibly in the presence of coupling agents or activators known to those skilled in the art.

Diagram 1

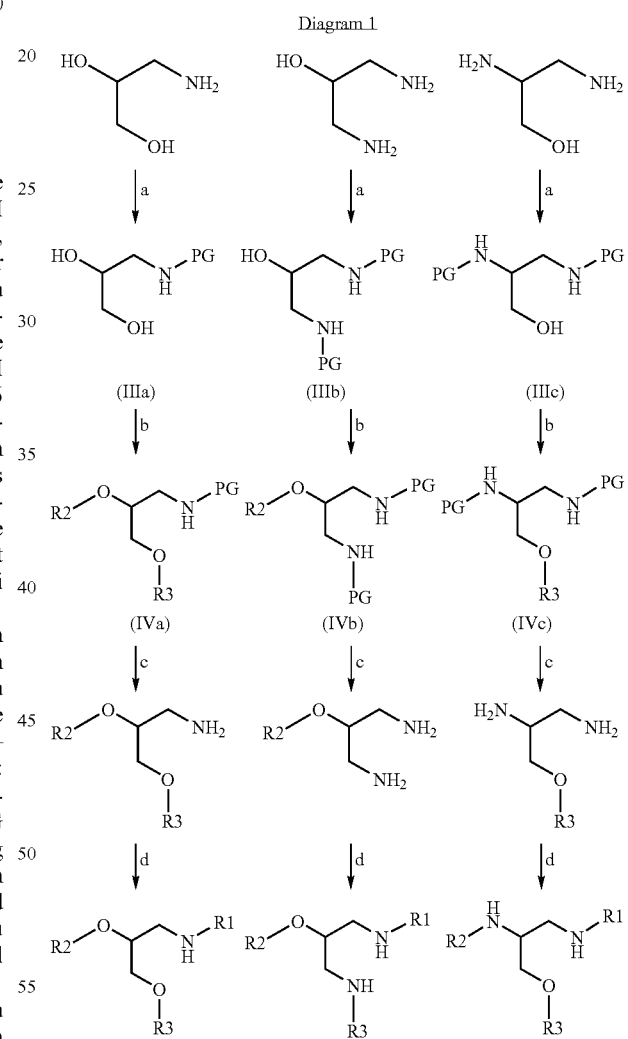

a. protection;
b. acylation;
c. deprotection;
d. amidification

Compounds represented by formula (I) according to the invention in which (i) G2 and G3 are oxygen atoms, (ii) R is a hydrogen atom and (iii) R1, R2 and R3, which are the same or different, represent a CO—R5 or CO—(CH$_2$)$_{2n+1}$—X—R6 group, can be obtained in different ways.

According to a first method, a compound represented by formula (I) according to the invention, in which (i) G2 and G3 are oxygen atoms, (ii) R and R2 are hydrogen atoms and (iii) R1, R3, which are the same or different, represent a CO—R5 or CO—$(CH_2)_{2n+1}$—X—R6 group, is reacted with a compound corresponding to the formula A°-CO-A2 in which A2 a reactive group selected for example in the group consisting of OH and Cl, and A° is the R5 group or the $(CH_2)_{2n+1}$—X—R6 group, possibly in the presence of coupling agents or activators known to those skilled in the art.

According to this method of preparation, compounds represented by formula (I) in which (i) G2 and G3 are oxygen atoms, (ii) R and R2 are hydrogen atoms and (iii) R1 and R3, which are the same or different, represent a CO—R5 or CO—$(CH_2)_{2n+1}$—X—R6 group, can be obtained from a compound represented by formula (IIa) such as defined hereinabove and a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

According to another particular inventive method, compounds represented by formula (I) in which (i) G2 and G3 are oxygen atoms, (ii) R is a hydrogen atom and (iii) R1, R2 and R3, which are the same or different, represent a CO—R5 or CO—$(CH_2)_{2n+1}$—X—R6 group, can be obtained from a compound represented by formula (I) according to the invention in which (i) G2 and G3 are oxygen atoms, (ii) R, $R_2$ and R3 represent a hydrogen atom and (iii) R1 is a CO—R5 or CO—$(CH_2)_{2n+1}$—X—R6 group (compound of formula (IIa)) according to the following steps (diagram 2):

a) reacting a compound represented by formula (IIa) with a compound PG-E in which PG is a protective group and E is a reactive group selected for example in the group consisting of OH and a halogen, to give a compound represented by general formula (V) in which R1 is a CO—R5 or CO—$(CH_2)_{2n+1}$—X—R6 group. Advantageously, the reaction can be carried out by adapting the protocols described by (Marx, Piantadosi et al. 1988) and (Gaffney and Reese 1997) in which PG-E can represent triphenylmethyl chloride or 9-phenylxanthene-9-ol or else 9-chloro-9-phenylxanthene;

b) reacting a compound represented by formula (V) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (VI), in which R1 and R2, which are the same or different, represent a CO—R5 or CO—$(CH_2)_{2n+1}$—X—R6 group and PG is a protective group;

c) deprotecting the compound (VI), in conditions known to those skilled in the art, to give a compound represented by general formula (I) in which (i) G2 and G3 are oxygen atoms, (ii) R and R3 are hydrogen atoms and (iii) R1 and R2, which are the same or different, represent a CO—R5 or CO—$(CH_2)_{2n+1}$—X—R6 group;

d) reacting a compound represented by general formula (I) in which (i) G2 and G3 are oxygen atoms, (ii) R and R3 are hydrogen atoms and (iii) R1 and R2, which are the same or different, represent a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

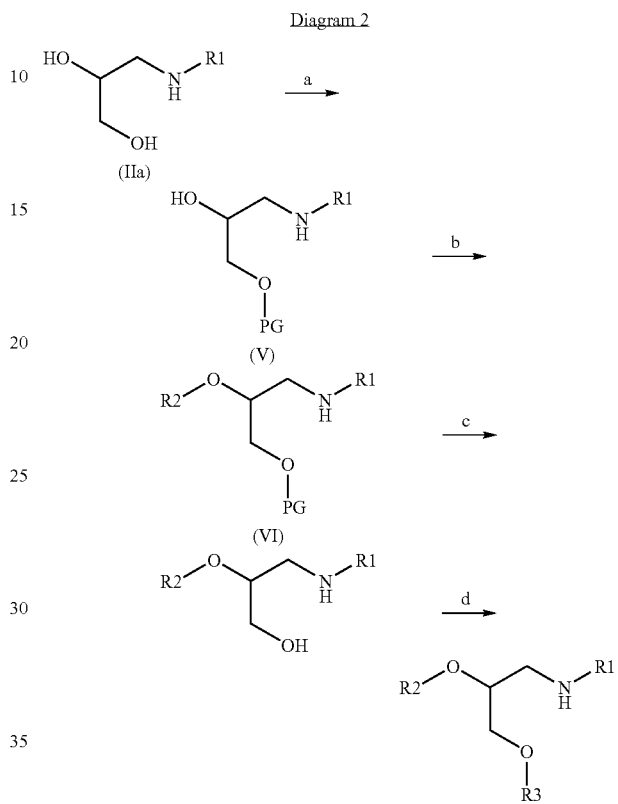

Diagram 2 a: protection;
b: esterification;
c: deprotection;
d: esterification

In an advantageous manner, the hereinabove steps are carried out according to the protocols described by (Marx, Piantadosi et al. 1988).

According to another method of the invention, compounds represented by formula (I) in which (i) G2 or G3 represent an oxygen atom or a N—R4 group, (ii) at least one of the groups G2 or G3 represents a N—R4 group, (iii) R and R4 independently represent linear or branched alkyl groups, saturated or not, optionally substituted, containing from 1 to 5 carbon atoms and (iv) R1, R2 and R3, which are the same or different, represent a CO—R5 group or a CO—$(CH_2)_{2n+1}$—X—R6 group, are obtained by reacting a compound represented by formula (I) in which (i) one of the groups G2R2 or G3R3 represents a hydroxyl group and the other group G2R2 or G3R3 represents a NR4R2 or NR4R3 group, respectively, with R2 or R3 representing a CO—R5 group or a CO—$(CH_2)_{2n+1}$—X—R6 group, (ii) R and R4 independently represent a linear or branched alkyl group, saturated or not, optionally substituted, containing from 1 to 5 carbon atoms and (iii) R1 represents a CO—R5 group or a CO—$(CH2)_{2n+1}$—X—R6 group, with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

Compounds represented by formula (I) according to the invention in which (i) one of the groups G2R2 or G3R3 represents a hydroxyl group and the other group G2R2 or G3R3 represents a NR4R2 or NR4R3 group, respectively, with R2 or R3 representing a CO—R5 group or a CO—$(CH_2)_{2n+1}$—X—R6 group, (ii) R and R4 independently represent linear or branched alkyl groups, saturated or not, optionally substituted, containing from 1 to 5 carbon atoms and (iii) R1 represents a CO—R5 group or a CO—$(CH_2)_{2n+1}$—X—R6 group, are obtained from compounds represented by formula (I) according to the invention in which one of the groups G2R2 or G3R3 represents a hydroxyl group and the other group G2R2 or G3R3 represents a NR4R2 or NR4R3 group, respectively, with R2 or R3 representing a CO—R5 group or a CO—$(CH_2)_{2n+1}$—X—R6 group, (ii) R and R4 independently represent a group such as defined hereinabove and (iii) R1 is a hydrogen atom and a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

In a first embodiment, compounds represented by formula (I) according to the invention in which (i) G2 is an oxygen atom, (ii) G3 represents a N—R4 group, (iii) R and R4 independently represent linear or branched alkyl groups, saturated or not, optionally substituted, containing from 1 to 5 carbon atoms, (iv) R1 and R2 are hydrogen atoms and (v) R3 represents a CO—R5 group or a CO—$(CH_2)_{2n+1}$—X—R6 group are obtained in the following manner (diagram 3):

a) reacting 1-aminoglycerol with a compound corresponding to the formula R—CHO in which R represents a linear or branched alkyl group, saturated or not, optionally substituted, containing from 1 to 5 carbon atoms and CHO is the aldehyde function in the presence of reducing agents known to those skilled in the art to give a compound represented by formula (VII) in which R is a group such as defined hereinabove. Advantageously, said reaction can be carried out by adapting the protocols described by (Antoniadou-Vyzas, Foscolos et al. 1986);

b) reacting a compound represented by formula (VII) with a compound (PG)$_2$O in which PG is a protective group to give a compound represented by general formula (VIII). Advantageously, the reaction can be carried out by adapting the protocols described by (Nazih, Cordier et al. 2000) and (Kotsovolou, Chiou et al. 2001) in which (PG)$_2$O represents di-tert-butyl dicarbonate;

c) reacting a compound represented by formula (VIII) with a compound corresponding to the formula LG-E in which E represents a halogen and LG is a reactive group selected for example in the group consisting of mesyl, tosyl, etc., to give a compound represented by general formula (IX) by adapting the method described by [Kitchin, Bethell et al. 1994];

d) reacting a compound represented by formula (IX) with a compound corresponding to the formula R4-NH$_2$ in which R4 represents a linear or branched alkyl group, saturated or not, optionally substituted, containing from 1 to 5 carbon atoms and NH$_2$ represents the amine function, according to the method described by (Ramalingan, Raju et al. 1995), to give a compound corresponding to formula (X) in which R and R4, optionally different, are such as defined hereinabove;

e) reacting a compound represented by formula (X) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by formula (XI) in which R and R4 represent linear or branched alkyl groups, saturated or not, optionally substituted, containing from 1 to 5 carbon atoms, R3 represents the R5 group or the $(CH_2)_{2n+1}$—X—R6 group and PG is a protective group;

f) deprotecting the compound (XI) in conditions known to those skilled in the art.

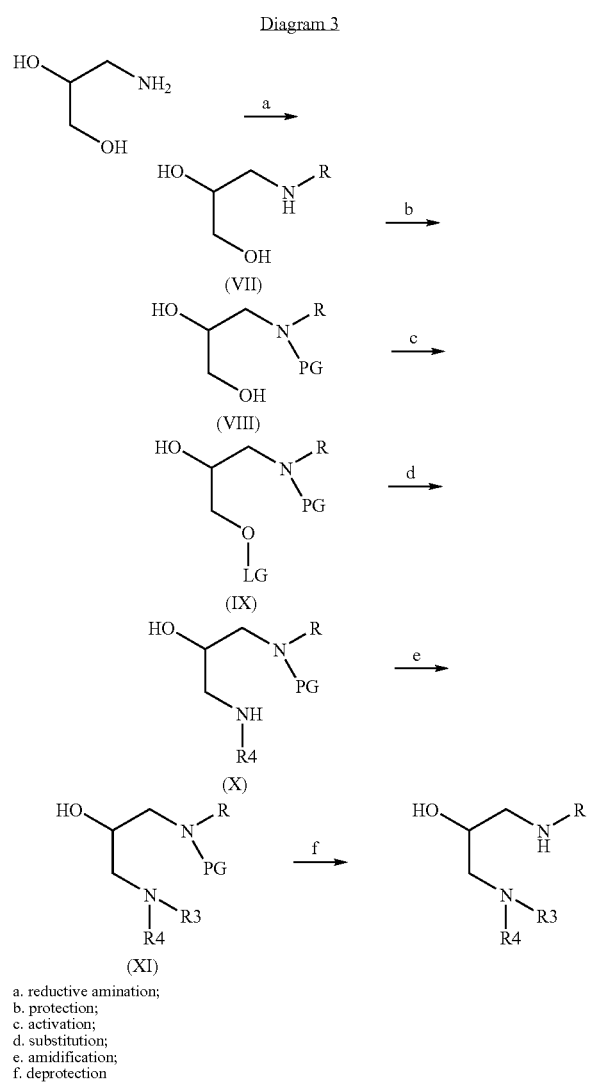

Diagram 3 a. reductive amination;
b. protection;
c. activation;
d. substitution;
e. amidification;
f. deprotection According to a second embodiment, compounds represented by formula (I) according to the invention in which (i) G3 is an oxygen atom, (ii) G2 represents a N—R4 group, (iii) R and R4 represent linear or branched alkyl groups, saturated or not, optionally substituted, containing from 1 to 5 carbon atoms, (iv) R1 and R3 are hydrogen atoms and (v) R2 represents a CO—R5 group or a CO—$(CH_2)_{2n+1}$—X—R6 group are obtained in the following manner (diagram 4):

a) reacting a compound represented by formula (VIII) with a compound PG'-E in which PG' is a protective group and E is a reactive group selected for example in the group consisting of OH or a halogen, to give a compound represented by general formula (XII) in which R represents a linear or branched alkyl group, saturated or not, optionally substituted, containing from 1 to 5 carbon atoms and PG is another protective group such as defined hereinabove. Advantageously, the reaction can be carried out by adapting the protocols described by (Marx, Piantadosi et al. 1988) and (Gaffney and Reese 1997) in which PG'-E can represent triphenylmethyl chloride or 9-phenylxanthene-9-ol or else 9-chloro-9-phenylxanthene;

b) reacting a compound represented by formula (XII) such as defined hereinabove with a compound corresponding to the formula LG-E in which E represents a halogen and LG is a reactive group selected for example in the group consisting of mesyl, tosyl, etc., to give a compound represented by general formula (XIII) in which R represents a linear or branched alkyl group, saturated or not, optionally substituted, containing from 1 to 5 carbon atoms and PG and PG' are protective groups, by adapting the method described by (Kitchin, Bethell et al. 1994);

c) reacting a compound represented by formula (XIII) such as defined hereinabove with a compound corresponding to the formula R4-NH$_2$ in which R4 represents a linear or branched alkyl group, saturated or not, optionally substituted, containing from 1 to 5 carbon atoms and NH$_2$ represents the amine function, according to the method described by (Ramalingan, Raju et al. 1995), to obtain a compound represented by formula (XIV) in which R and R4 are independently such as defined hereinabove;

d) reacting a compound represented by formula (XIV) with a compound corresponding to the formula A°-CO-A2 in which A2 is a reactive group selected for example in the group consisting of OH and Cl, and A° is the R5 group or the (CH$_2$)$_{2n+1}$—X—R6 group, possibly in the presence of coupling agents or activators known to those skilled in the art to give a compound represented by formula (XV) in which R and R4 independently represent linear or branched alkyl groups, saturated or not, optionally substituted, containing from 1 to 5 carbon atoms, R2 represents a CO—R5 group or a CO—(CH$_2$)$_{2n+1}$—X—R6 group, PG and PG' are protective groups;

e) deprotecting a compound represented by formula (XV) in conventional conditions known to those skilled in the art to obtain a compound represented by general formula (I) according to the invention in which (i) R and R4 independently represent linear or branched alkyl groups, saturated or not, optionally substituted, containing from 1 to 5 carbon atoms, (ii) R1 and R3 are hydrogen atoms and (iii) R2 represents a CO—R5 group or a CO—(CH$_2$)$_{2n+1}$—X—R6 group.

Diagram 4

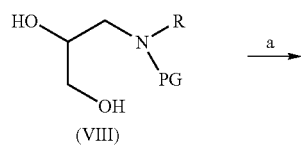

(VIII)

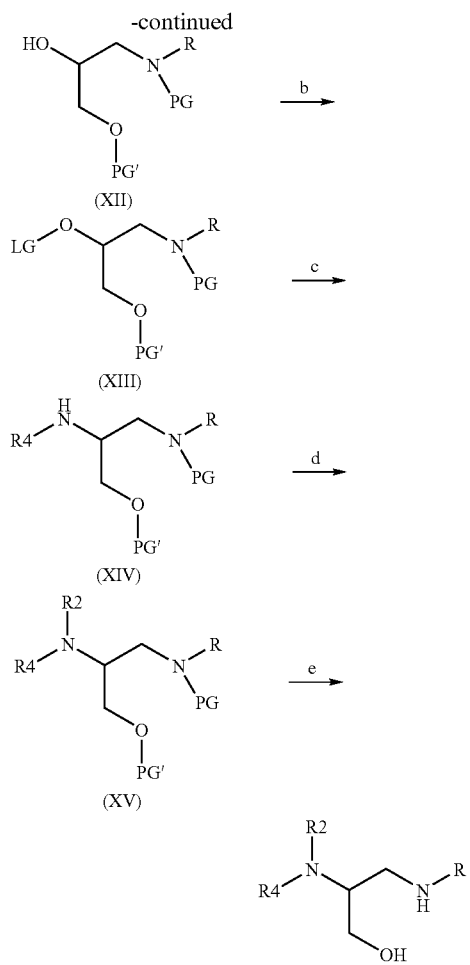

a. protection;
b. activation;
c. substitution;
d. amidification;
e. deprotection Compounds represented by formula (I) according to the invention in which (i) G2 and G3 are sulfur atoms or a NH group, (ii) R is a hydrogen atom and (iii) R1, R2 and R3 are hydrogen atoms or represent a CO—R5 or CO—(CH$_2$)$_{2n+1}$—X—R6 group can be obtained by different methods.

According to a first embodiment, compounds represented by formula (I) according to the invention in which (i) G2 and G3 are sulfur atoms or a NH group, (ii) R is a hydrogen atom and (iii) R1, R2 and R3 are hydrogen atoms or represent a CO—R5 or CO—(CH$_2$)$_{2n+1}$—X—R6 group, R1, R2 and/or R3 having the same meaning when they are carried on a same heteroatom (sulfur or nitrogen), can be obtained in the following manner (diagram 5A):

a) reacting a compound represented by formula (IIa-c) with a compound corresponding to the formula LG-E in which E represents a halogen and LG is a reactive group selected for example in the group consisting of mesyl, tosyl, etc., to give a compound represented by general formula (XVIa-c);

b) reacting a compound represented by formula (XVIa-c) with a compound corresponding to the formula Ac—S$^-$ B$^+$ in which Ac represents a short acyl group, preferably the acetyl group, and B is a counter-ion selected for example in the group consisting of sodium and potassium, preferably potassium to give the compound represented by general formula (XVIIa-c). Advantageously, said reaction can be carried out by adapting the protocol described by (Gronowitz, Herslöf et al. 1978);

c) deprotecting a compound represented by formula (XVIIa-c), in conventional conditions known to those skilled in the art, and for example in basic medium, to give a compound represented by general formula (I) in which (i) G2 and G3 represent a sulfur atom or a NH group and (ii) R1, R2 and R3, which are the same or different, represent a hydrogen atom or a CO—R5 or CO—(CH$_2$)$_{2n+1}$—X—R6 group;

d) reacting a compound represented by general formula (I) in which (i) G2 and G3 represent a sulfur atom or a NH group and (ii) R1, R2 and R3, which are the same or different, represent a hydrogen atom or a CO—R5 or CO—(CH$_2$)$_{2n+1}$—X—R6 group, with a compound corresponding to the formula A°-CO-A2 in which A2 is a reactive group selected for example in the group consisting of OH and Cl, and A° is the R5 group or the (CH$_2$)$_{2n+1}$—X—R6 group, possibly in the presence of coupling agents or activators known to those skilled in the art.

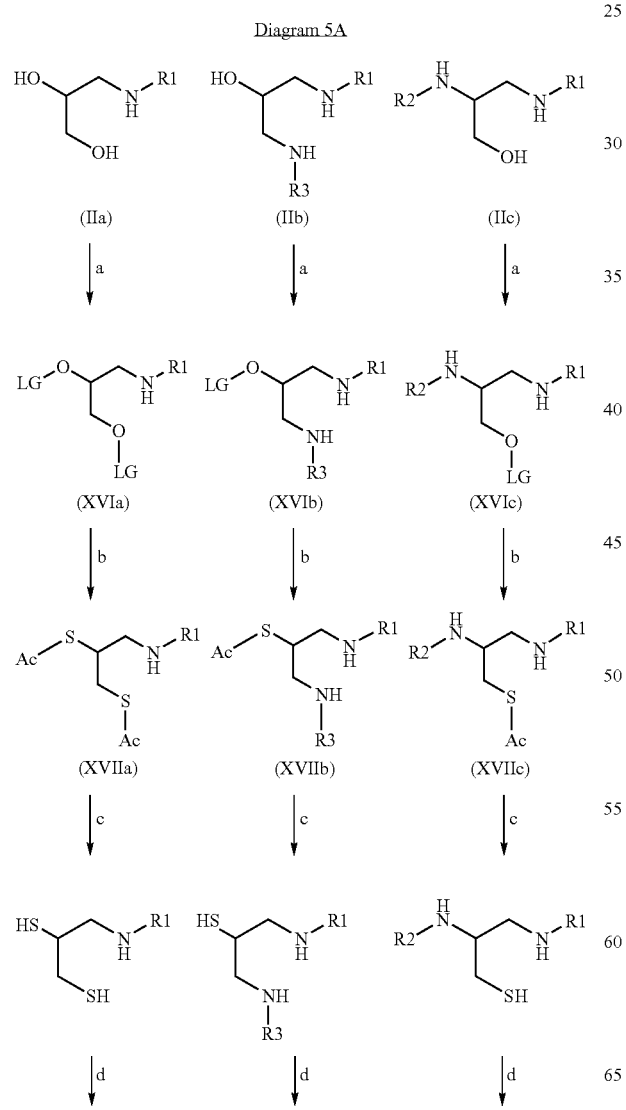

Diagram 5A

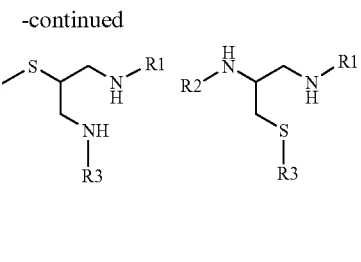

-continued a. activation;
b. substitution;
c. deprotection;
d. acylation

According to similar synthetic method, compounds having formula (I) according to the invention in which (i) G2 and G3 are sulfur atoms or a NH group, (ii) R is a hydrogen atom and (iii) R1, R2 and R3 are hydrogen atoms or represent a CO—R5 or CO—(CH$_2$)$_{2n+1}$—X—R6 group, R1, R2 and/or R3 having the same meaning when they are carried on a same heteroatom (sulfur or nitrogen), can be prepared in the following manner (diagram 5B):

a) reacting a compound represented by formula (IIa-c) with a compound corresponding to the formula (LG)2 in which LG is a reactive group selected for example in the group consisting of iodine, bromine, etc., possibly in the presence of activators known to those skilled in the art to give a compound represented by general formula (XVId-f);

b) reacting a compound represented by formula (XVId-f) with a compound corresponding to the formula HS$^-$B$^+$ in which B is a counter-ion selected for example in the group consisting of sodium or potassium, preferably sodium to give a compound represented by general formula (I) in which (i) G2 and G3 represent a sulfur atom or a NH group and (ii) R1, R2 and R3, which are the same or different, represent a hydrogen atom or a CO—R5 or CO—(CH$_2$)$_{2n+1}$—X—R6 group;

c) reacting a compound represented by general formula (I) in which (i) G2 and G3 represent a sulfur atom or a NH group and (ii) R1, R2 and R3, which are the same or different, represent a hydrogen atom or a CO—R5 or CO—(CH$_2$)$_{2n+1}$—X—R6 group, with a compound corresponding to the formula A°-CO-A2 in which A2 is a reactive group selected for example in the group consisting of OH and Cl, and A° is the R5 group or the (CH$_2$)$_{2n+1}$—X—R6 group, possibly in the presence of coupling agents or activators known to those skilled in the art.

Diagram 5B

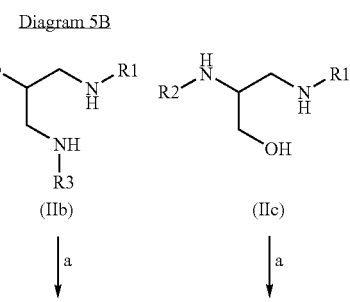

-continued

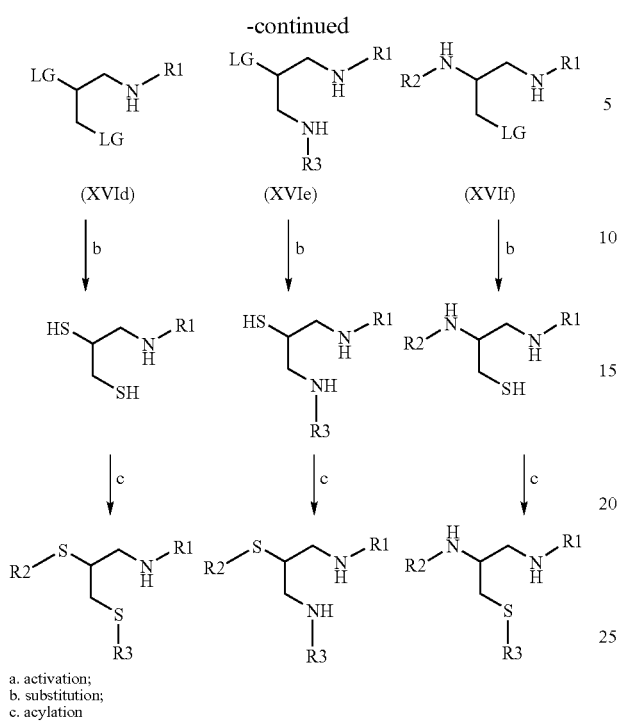

a. activation;
b. substitution;
c. acylation

Said reaction enables the synthesis of compounds represented by general formula (I) in which the groups carried on a same heteroatom (nitrogen or sulfur) respectively (R2 and R3), (R1 and R3) and (R1 and R2) have the same meaning.

The above steps can be carried out in an advantageous manner according to the protocols described by (Adams, Doyle et al. 1960) and (Gronowitz, Herslöf et al. 1978).

According to another method of the invention (diagram 6), compounds represented by formula (I) according to the invention in which (i) G2 and G3 are sulfur atoms or a NH group, (ii) R is a hydrogen atom and (iii) R1, R2 and R3 are hydrogen atoms or represent a CO—R5 or CO—$(CH_2)_{2n+1}$—X—R6 group can be prepared from compounds represented by formula (IIIa-c) by a method comprising:

a) reacting a compound represented by formula (IIIa-c) with a compound corresponding to the formula LG-E in which E represents a halogen and LG is a reactive group selected for example in the group consisting of mesyl, tosyl, etc., to give a compound represented by general formula (XVIIIa-c) in which PG represents a protective group;

b) reacting a compound represented by formula (XVIIIa-c) with a compound corresponding to the formula Ac—S⁻B⁺ in which Ac represents a short acyl group, preferably the acetyl group, and B is a counter-ion selected for example in the group consisting of sodium and potassium, preferably potassium to give a compound represented by general formula (XIXa-c). Advantageously, said reaction can be carried out by adapting the protocol described by (Gronowitz, Herslöf et al. 1978);

c) deprotecting the sulfur atom of a compound (XIXa-c) in conditions known to those skilled in the art, to give a compound represented by general formula (XXa-c);

d) reacting a compound represented by general formula (XXa-c) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XXIa-c) in which R2 and R3 represent a CO—R5 or CO—$(CH_2)_{2n+1}$—X—R6 group;

e) deprotecting a compound represented by formula (XXIa-c) in conventional conditions known to those skilled in the art, to give a compound represented by formula (I) according to the invention in which (i) G2 and G3 are sulfur atoms or a NH group, (ii) R and R1 are hydrogen atoms and (iii) R2 and R3 represent a hydrogen atom, a CO—R5 or CO—$(CH_2)_{2n+1}$—X—R6 group.

f) reacting a compound represented by formula (I) according to the invention in which (i) G2 and G3 are sulfur atoms or a NH group, (ii) R and R1 are hydrogen atoms and (iii) R2 and R3 represent a hydrogen atom, a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

Said reaction enables the synthesis of compounds represented by general formula (I) in which the groups carried on a same heteroatom (nitrogen or sulfur) respectively (R2 and R3), (R1 and R3) and (R1 and R2) have the same meaning.

In an advantageous manner, the above steps are carried out according to the protocols described by (Adams, Doyle et al. 1960), (Gronowitz, Herslöf et al. 1978), (Bhatia and Hajdu 1987) and (Murata, Ikoma et al. 1991).

Diagram 6

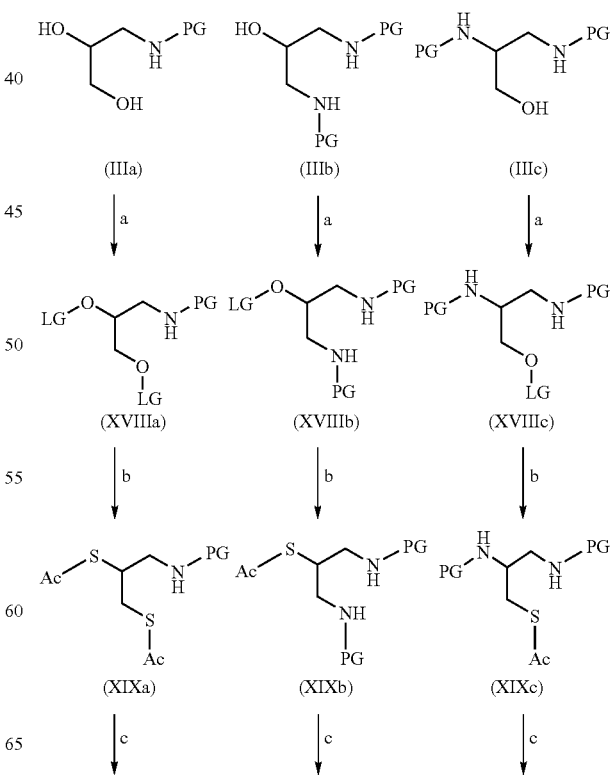

-continued

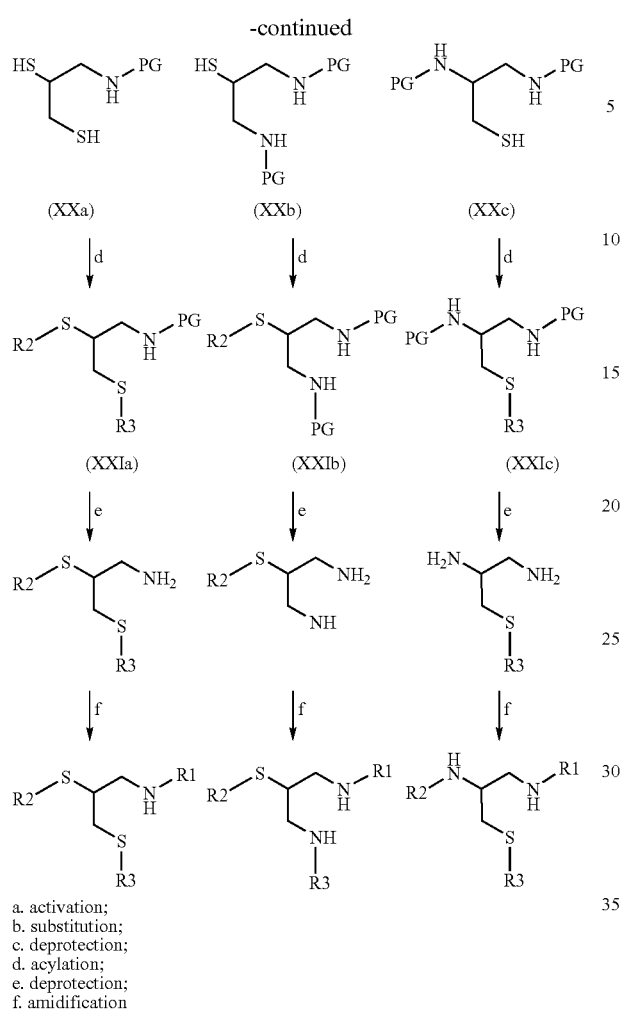

a. activation;
b. substitution;
c. deprotection;
d. acylation;
e. deprotection;
f. amidification Compounds represented by general formula (I) in which (i) G2 and G3 represent sulfur atoms or a N—R4 group, (ii) R and R4 independently represent a linear or branched alkyl group, saturated or not, optionally substituted, containing from 1 to 5 carbon atoms, (iii) R1, R2 and R3, which are the same or different, represent a CO—R5 group or a CO—$(CH_2)_{2n+1}$—X—R6 group, are obtained by reacting a compound represented by general formula (I) in which (i) G2 or G3 represent a sulfur atom or a N—R4 group, (ii) R and R4 independently represent groups such as defined hereinabove, (iii) R1 is a hydrogen atom and (iv) R2 and R3, which are the same or different, represent a CO—R5 group or a CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

Compounds represented by general formula (I) in which (i) the group G2 and G3 represent sulfur atoms or a N—R4 group, (ii) R and R4 independently represent groups such as defined hereinabove, (iii) R1 is a hydrogen atom and (iv) R2 and R3, which are the same or different, represent a CO—R5 group or a CO—$(CH_2)_{2n+1}$—X—R6 group, can be obtained by the following methods:

In a first embodiment, compounds represented by formula (I) according to the invention in which (i) the group G2 is a sulfur atom, (ii) G3 represents a N—R4 group, (iii) R and R4 independently represent different linear or branched alkyl group, saturated or not, optionally substituted, containing from 1 to 5 carbon atoms, (iv) R1 is a hydrogen atom and (v) R2 and R3, which are the same or different, represent a CO—R5 group or a CO—$(CH_2)_{2n+1}$—X—R6 group are obtained in the following manner (diagram 7):

a) reacting a compound represented by formula (XI) with a compound corresponding to the formula LG-E in which E represents a halogen and LG is a reactive group selected for example in the group consisting of mesyl, tosyl, etc., to give a compound represented by general formula (XXII) in which PG represents a protective group;

b) reacting a compound represented by formula (XXII) with a compound corresponding to the formula Ac—S⁻ B⁺ in which Ac represents a short acyl group, preferably the acetyl group, and B is a counter-ion selected for example in the group consisting of sodium and potassium, preferably potassium to give the compound represented by general formula (XXIII). Advantageously, said reaction is carried out by adapting the protocol described by (Gronowitz, Herslöf et al. 1978);

c) deprotecting the sulfur atom of a compound represented by formula (XXIII) in conventional conditions known to those skilled in the art to give a compound represented by general formula (XXIV);

d) reacting a compound represented by general formula (XXIV) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XXV) in which R2 and R3, which are the same or different, represent a CO—R5 or CO—$(CH_2)_{2n+1}$—X—R6 group;

e) deprotectig the compound of formula (XXV) in conditions known to those skilled in the art.

Diagram 7

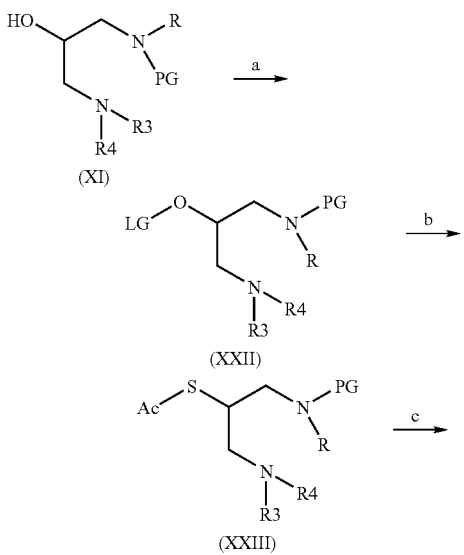

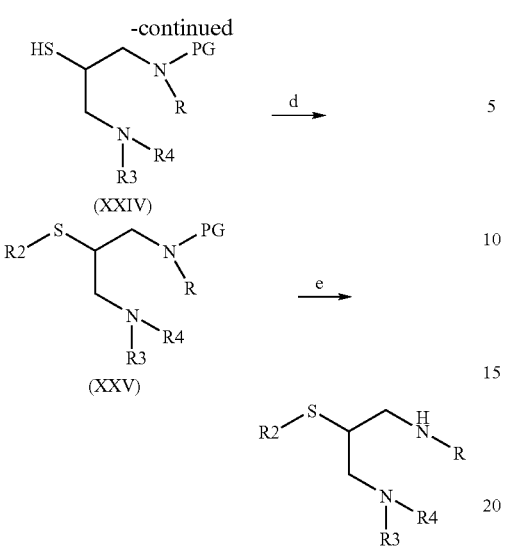

a. activation;
b. substitution;
c. deprotection;
d. acylation;
e. deprotection

According to another method (diagram 8), compounds represented by formula (I) according to the invention in which (i) G2 represents a N—R4 group, (ii) G3 is a sulfur atom, (iii) R and R4 independently represent different linear or branched alkyl groups, saturated or not, optionally substituted, containing from 1 to 5 carbon atoms, (iv) R1 is a hydrogen atom and (v) R2 and R3, which are the same or different, represent a CO—R5 group or a CO—$(CH_2)_{2n+1}$—X—R6 group are obtained in the following manner:

a) reacting the compound represented by formula (IX) with a compound corresponding to the formula Ac—S⁻ B⁺ in which Ac represents a short acyl group, preferably the acetyl group, and B is a counter-ion selected for example in the group consisting of sodium and potassium, preferably potassium to give the compound represented by general formula (XXVI). Advantageously, said reaction can be carried out by adapting the protocol described by (Gronowitz, Herslöf et al. 1978);

b) reacting a compound represented by formula (XXVI) with a compound corresponding to the formula LG-E in which E represents a halogen and LG is a reactive group selected for example in the group consisting of mesyl, tosyl, etc., to give a compound represented by general formula (XXVII) in which PG represents a protective group;

c) reacting the compound (XXVII) with a compound represented by formula R4-NH₂ in which R4 represents a linear or branched alkyl group, saturated or not, optionally substituted, containing from 1 to 5 carbon atoms and NH₂ represents the amine function, according to the method described by (Ramalingan, Raju et al. 1995), to give a compound represented by formula (XXVIII) in which R and R4 independently represent different linear or branched alkyl groups, saturated or not, optionally substituted, containing from 1 to 5 carbon atoms;

d) reacting a compound represented by general formula (XXVIII) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XXIX);

e) deprotecting the sulfur atom of a compound represented by formula (XXIX) in conventional conditions known to those skilled in the art to give a compound represented by general formula (XXX);

f) reacting a compound represented by general formula (XXX) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XXXI) in which R2 and R3, which are the same or different, represent a CO—R5 or CO—$(CH_2)_{2n+1}$—X—R6 group;

g) deprotecting a compound represented by formula (XXXI) in conventional conditions known to those skilled in the art.

Diagram 8

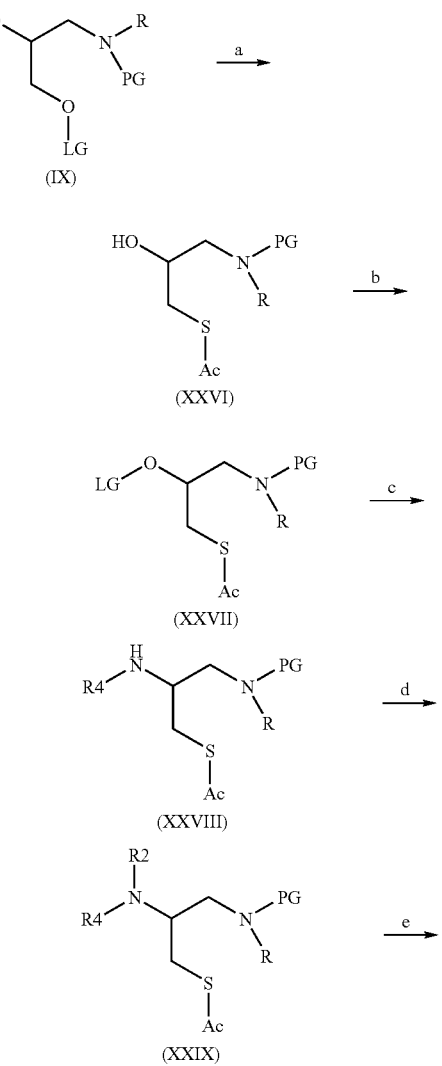

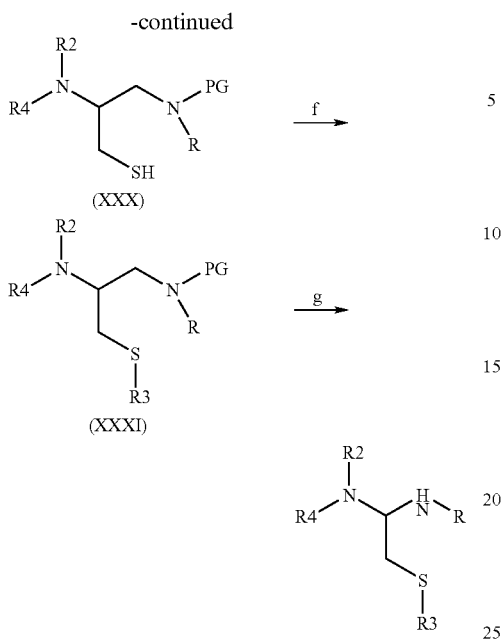

(XXX)

(XXXI)

a. substitution;
b. activation;
c. substitution;
d. amidification;
e. deprotection;
f. acylation;
g. deprtection Compounds represented by formula (I) according to the invention in which (i) G2 is a sulfur atom, (ii) G3 is an oxygen atom, (iii) R is a hydrogen atom, (iv) R1 and R2 represent a CO—R5 or CO—$(CH_2)_{2n+1}$—X—R6 group and (v) R3 is a hydrogen atom or represents a CO—R5 or CO—$(CH_2)_{2n+1}$—X—R6 group, can be prepared from compounds having formula (V) according to the following method (diagram 9A):

a) reacting the compound (V) with a compound corresponding to the formula LG-E in which E represents a halogen and LG is a reactive group selected for example in the group consisting of mesyl, tosyl, etc., to give a compound represented by general formula (XXXII) in which PG represents a protective group;

b) reacting a compound represented by formula (XXXII) with a compound corresponding to the formula Ac—S⁻ B⁺ in which Ac represents a short acyl group, preferably the acetyl group, and B is a counter-ion selected for example in the group consisting of sodium and potassium, preferably potassium to give the compound represented by general formula (XXXIII). Advantageously, said reaction can be carried out by adapting the protocol described by (Gronowitz, Herslöf et al. 1978);

c) deprotecting the sulfur atom of a compound (XXXIII), in conventional conditions known to those skilled in the art, to give a compound represented by general formula (XXXIV);

d) reacting a compound represented by general formula (XXXIV) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XXXV) in which R1 and R2, which are the same or different, represent a CO—R5 or CO—$(CH_2)_{2n+1}$—X—R6 group;

e) deprotecting a compound (XXXV) in conventional conditions known to those skilled in the art to give a compound represented by general formula (I) in which G2 is a sulfur atom, G3 is an oxygen atom, R and R3 are hydrogen atoms and R1 and R2, which are the same or different, represent a CO—R5 or CO—$(CH_2)_{2n+1}$—X—R6 group;

f) reacting a compound represented by general formula (I) in which (i) G2 is a sulfur atom, (ii) G3 is an oxygen atom, (iii) R and R3 are hydrogen atoms and (iv) R1 and R2, which are the same or different, represent a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

Diagram 9A

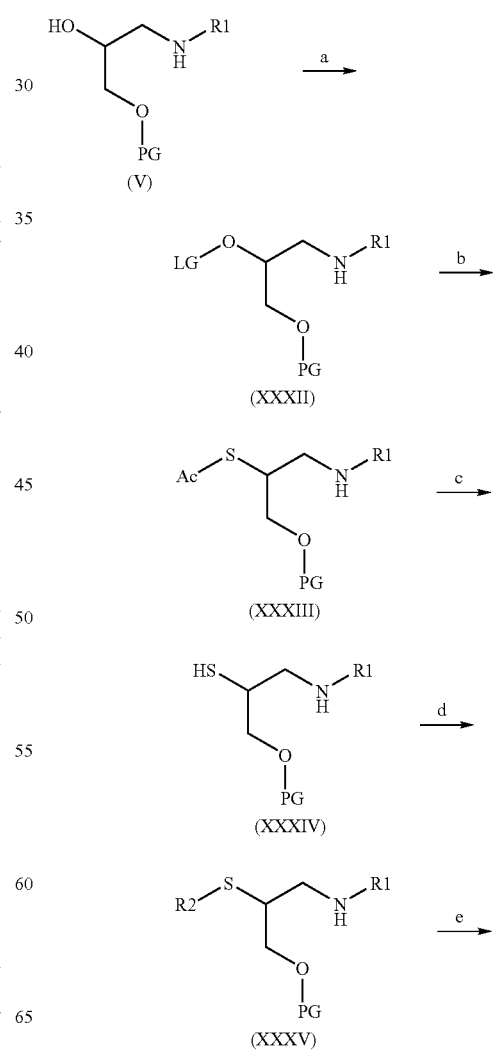

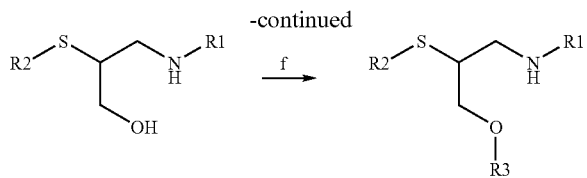

a. activation;
b. substitution;
c. deprotection;
d. acylation;
e. deprotection;
f. acylation According to a similar method of synthesis, compounds represented by formula (I) according to the invention in which (i) G2 is a sulfur atom, (ii) G3 is an oxygen atom, (iii) R is a hydrogen atom, (iv) R1 and R2 represent a CO—R5 or CO—$(CH_2)_{2n+1}$—X—R6 group and (v) R3 is a hydrogen atom or represents a CO—R5 or CO—$(CH_2)_{2n+1}$—X—R6 group, can be prepared from compounds of formula (V) by the following method (diagram 9B):

a) reacting the compound (V) with a compound corresponding to the formula $(LG)_2$ in which LG is a reactive group selected for example in the group consisting of iodine, bromine, etc., to give a compound represented by general formula (XXXIIa) in which PG represents a protective group;

b) reacting a compound represented by formula (XXXIIa) with a compound corresponding to the formula HS⁻B⁺ in which B is a counter-ion selected for example in the group consisting of sodium and potassium, preferably sodium to give a compound represented by general formula (XXXIV);

c) reacting a compound represented by general formula (XXXIV) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XXXV) in which R1 and R2, which are the same or different, represent a CO—R5 or CO—$(CH_2)_{2n+1}$—X—R6 group;

d) deprotecting the compound (XXXV) in conventional conditions known to those skilled in the art to give a compound represented by general formula (I) in which G2 is a sulfur atom, G3 is an oxygen atom, R and R3 are hydrogen atoms and R1 and R2, which are the same or different, represent a CO—R5 or CO—$(CH_2)_{2n+1}$—X—R6 group;

e) reacting a compound represented by general formula (I) in which (i) G2 is a sulfur atom, (ii) G3 is an oxygen atom, (iii) R and R3 are hydrogen atoms and (iv) R1 and R2, which are the same or different, represent a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

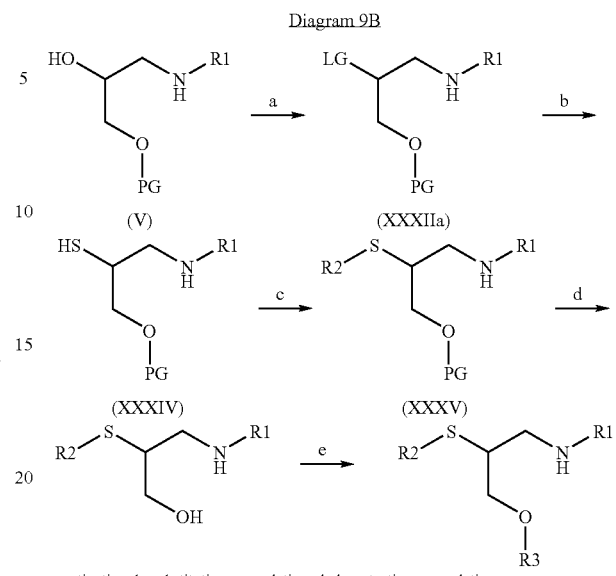

Diagram 9B a. activation; b. substitution; c. acylation; d. deprotection; e. acylation Compounds represented by formula (I) according to the invention in which (i) G2 is a sulfur atom, (ii) G3 is an oxygen atom, (iii) R is a hydrogen atom, (iv) R1 and R3 represent a hydrogen atom or a CO—R5 or CO—$(CH_2)_{2n+1}$—X—R6 group, which are the same or different, and (v) R2 represents a CO—R5 or CO—$(CH_2)_{2n+1}$—X—R6 group, can be prepared from compounds having formula (IIIa) by the following method (diagram 10):

a) reacting a compound represented by formula (IIIa) with a compound PG'-E in which PG' is a protective group and E is a reactive group selected for example in the group consisting of OH or a halogen, to give a compound represented by general formula (XXXVI) in which PG is another protective group such as defined earlier. In an advantageous manner, the reaction can be carried out by adapting the protocols described by (Marx, Piantadosi et al. 1988) and (Gaffney and Reese 1997) in which PG-E can represent triphenylmethyl chloride or 9-phenylxanthene-9-ol or else 9-chloro-9-phenylxanthene;

b) reacting the compound (XXXVI) with a compound corresponding to the formula LG-E in which E represents a halogen and LG is a reactive group selected for example in the group consisting of mesyl, tosyl, etc., to give a compound represented by general formula (XXXVII) in which PG and PG' represent judiciously selected protective groups such as defined hereinabove;

c) reacting a compound represented by formula (XXXVII) with a compound corresponding to the formula Ac—S⁻B⁺ in which Ac represents a short acyl group, preferably the acetyl group, and B is a counter-ion selected for example in the group consisting of sodium and potassium, preferably potassium to give the compound represented by general formula (XXXVIII). Advantageously, said reaction can be carried out by adapting the protocol described by (Gronowitz, Herslöf et al. 1978);

d) deprotecting the sulfur atom of a compound (XXXVIII), in conventional conditions known to those skilled in the art, to give a compound represented by general formula (XXXIX);

e) reacting a compound represented by general formula (XXXIX) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XL) in which R2 represents a CO—R5 or CO—$(CH_2)_{2n+1}$—X—R6 group;

f) deprotecting a compound (XL) in conventional conditions known to those skilled in the art to give a compound represented by general formula (I) in which G2 is a sulfur atom, G3 is an oxygen atom, R, R1 and R3 are hydrogen atoms and R2 represents a CO—R5 or CO—$(CH_2)_{2n+1}$—X—R6 group (compound XLI);

g) reacting a compound represented by formula (XLI) with a compound $(PG)_2O$ in which PG is a protective group to give a compound represented by general formula (XLII). Advantageously, the reaction can be carried out by adapting the protocols described by (Nazih, Cordier et al. 2000) and (Kotsovolou, Chiou et al. 2001) in which $(PG)_2O$ represents di-tert-butyl dicarbonate;

h) reacting a compound represented by general formula (XLII) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by formula (XLIII);

i) deprotecting a compound (XLIII) in conventional conditions known to those skilled in the art to give a compound represented by general formula (I) in which G2 is a sulfur atom, G3 is an oxygen atom, R and R1 are hydrogen atoms and R2 and R3, which are the same or different, represent a CO—R5 or CO—$(CH_2)_{2n+1}$—X—R6 group;

j) reacting a compound represented by general formula (I) in which G2 is a sulfur atom, G3 is an oxygen atom, R and R1 are hydrogen atoms and R2 and R3, which are the same or different, represent a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

Diagram 10

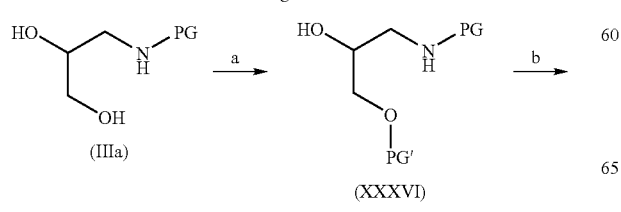

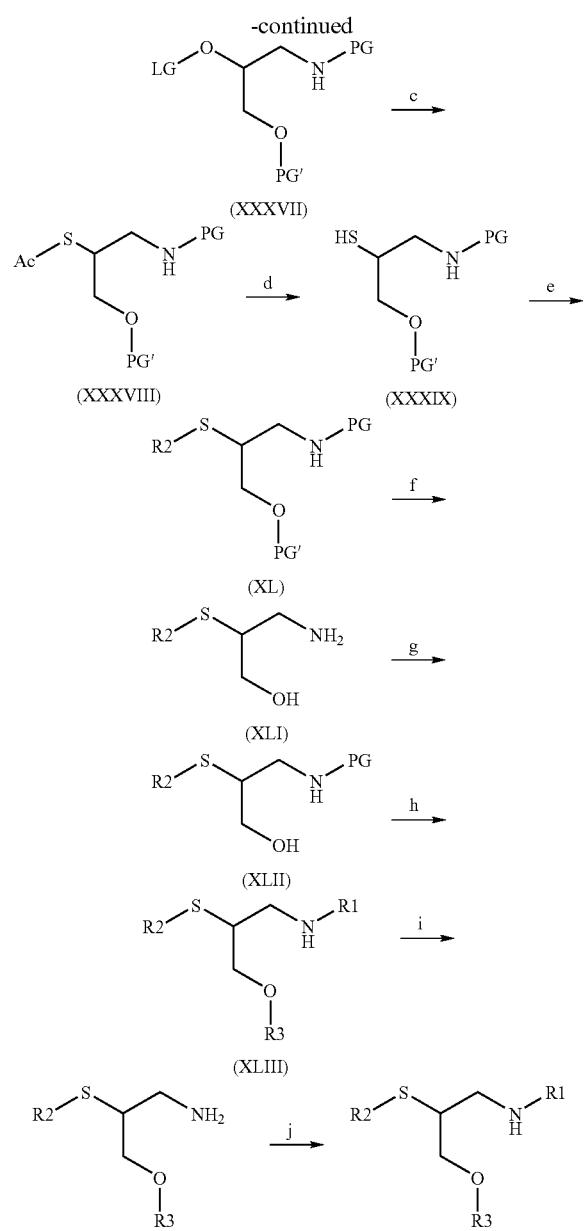

a. activation; b. substitution; c. acylation; d. deprotection; e. acylation; f. deprotection
g: protection; h: acylation; i: deprotection; j: amidification Compounds represented by formula (I) according to the invention in which (i) G2 is an oxygen atom, (ii) G3 is a sulfur atom, (iii) R is a hydrogen atom, (iv) R1 and R3 are hydrogen atoms or represent a CO—R5 or CO—$(CH_2)_{2n+1}$—X—R6 group and (v) R2 represents a hydrogen atom or a CO—R5 or CO—$(CH_2)_{2n+1}$—X—R6 group, can be prepared from compounds having formula (IIa) according to the following method (diagram 11):

a) reacting a compound represented by formula (IIa) such as defined hereinabove, with a compound corresponding to the formula LG-E (in stoichiometric amounts) in which E represents a halogen and LG is a reactive group selected for example in the group consisting of mesyl, tosyl, etc., to give a compound represented by general formula (XLIV);

b) reacting a compound represented by formula (XLIV) with a compound corresponding to the formula Ac—S⁻

B+ in which Ac represents a short acyl group, preferably the acetyl group, and B is a counter-ion selected for example in the group consisting of sodium and potassium, preferably potassium to give the compound represented by general formula (XLV). Advantageously, said reaction can be carried out by adapting the protocol described by (Gronowitz, Herslöf et al. 1978);

c) reacting a compound represented by formula (XLV) with a compound PG-E in which PG is a protective group and E is a reactive group selected for example in the group consisting of OH and a halogen, to give a compound represented by general formula (XLVI). Advantageously, the reaction can be carried out by adapting the protocols described by (Marx, Piantadosi et al. 1988) and (Gaffney and Reese 1997), in which PG-E can represent triphenylmethyl chloride or 9-phenylxanthene-9-ol or else 9-chloro-9-phenylxanthene;

d) deprotecting the sulfur atom of a compound (XLVI), in conditions known to those skilled in the art, to give a compound represented by general formula (XLVII);

e) reacting a compound represented by general formula (XLVII) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (XLVIII) in which R1 and R3, which are the same or different, represent a CO—R5 or CO—$(CH_2)_{2n+1}$—X—R6 group;

f) deprotecting a compound represented by formula (XLVIII), in conventional conditions known to those skilled in the art, to give a compound represented by general formula (I) in which G2 is an oxygen atom, G3 is a sulfur atom, R and R2 are hydrogen atoms and R1 and R3, which are the same or different, represent a CO—R5 or CO—$(CH_2)_{2n+1}$—X—R6 group;

g) reacting a compound represented by general formula (I) in which G2 is an oxygen atom, G3 is a sulfur atom, R and R2 are hydrogen atoms and R1 and R3, which are the same or different, represent a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

Diagram 11

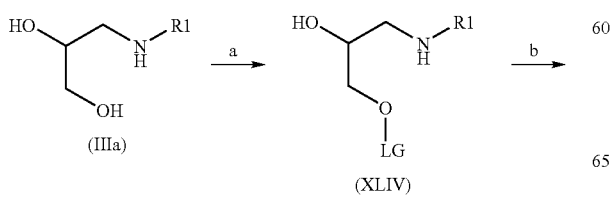

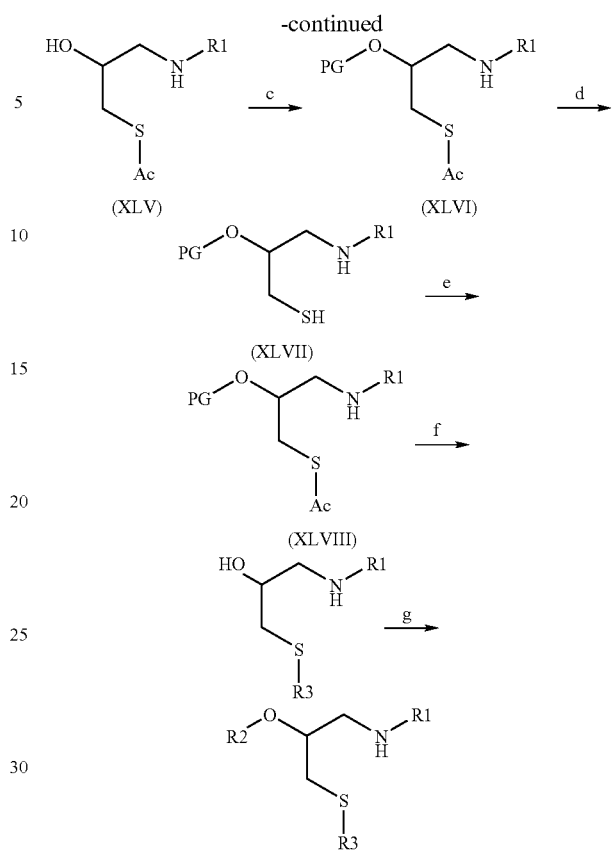

a. activation; b. substitution; c. protection; d. selective deprotection; e. acylation; f. deprotection; g. acylation Compounds represented by formula (I) according to the invention in which (i) G2 is an oxygen atom, (ii) G3 is a sulfur atom, (iii) R is a hydrogen atom, (iv) R1 and R3 are hydrogen atoms or represent a CO—R5 or CO—$(CH_2)_{2n+1}$—X—R6 group, which are the same or different, and (v) R3 represents a CO—R5 or CO—$(CH_2)_{2n+1}$—X—R6 group, can be rpepared from compounds having formula (IIIa) according to the following method (diagram 12):

a) reacting a compound represented by formula (IIIa) such as defined hereinabove, with a compound corresponding to the formula LG-E (in stoichiometric amounts) in which E represents a halogen and LG is a reactive group selected for example in the group consisting of mesyl, tosyl, etc., to give a compound represented by general formula (XLIX);

b) reacting a compound represented by formula (XLIX) with a compound corresponding to the formula Ac—S− B+ in which Ac represents a short acyl group, preferably the acetyl group, and B is a counter-ion selected for example in the group consisting of sodium and potassium, preferably potassium to give the compound represented by general formula (L). Advantageously, said reactino can be carried out by adapting the protocol described by (Gronowitz, Herslöf et al. 1978);

c) reacting a compound represented by formula (L) with a compound PG'-E in which PG' is a protective group and E is a reactive group selected for example in the group consisting of OH and a halogen, to give a compound represented by general formula (LI). Advantageously, the reaction can be carried out by adapting the protocols described by (Marx, Piantadosi et al. 1988) and (Gaffney and Reese 1997) in which PG'-E can represent triphenylmethyl chloride or 9-phenylxanthene-9-ol or else 9-chloro-9-phenylxanthene;

d) deprotecting the sulfur atom of a compound (LI), in conditions known to those skilled in the art, to give a compound represented by general formula (LII);

e) reacting a compound represented by general formula (LII) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (LIII) in which R3 represents a CO—R5 or CO—$(CH_2)_{2n+1}$—X—R6 group;

f) deprotecting a compound represented by formula (LIII), in conventional conditions known to those skilled in the art, to give a compound represented by general formula (I) in which G2 is an oxygen atom, G3 is a sulfur atom, R and R2 are hydrogen atoms and R3 represents a CO—R5 or CO—$(CH_2)_{2n+1}$—X—R6 group (compound LIV);

g) reacting a compound represented by formula (LIV) with a compound (PG)$_2$O in which PG is a protective group to give a compound represented by general formula (LV). Advantageously, the reaction can be carried out by adapting the protocols described by (Nazih, Cordier et al. 2000) and (Kotsovolou, Chiou et al. 2001) in which (PG)$_2$O represents di-tert-butyl dicarbonate;

h) reacting a compound represented by general formula (LV) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by formula (LVI);

i) deprotecting a compound (LVI) in conventional conditions known to those skilled in the art to give a compound represented by general formula (I) in which G3 is a sulfur atom, G2 is an oxygen atom, R and R1 are hydrogen atoms and R2 and R3, which are the same or different, represent a CO—R5 or CO—$(CH_2)_{2n+1}$—X—R6 group;

j) reacting a compound represented by general formula (I) in which G3 is a sulfur atom, G2 is an oxygen atom, R and R1 are hydrogen atoms and R2 and R3, which are the same or different, represent a CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

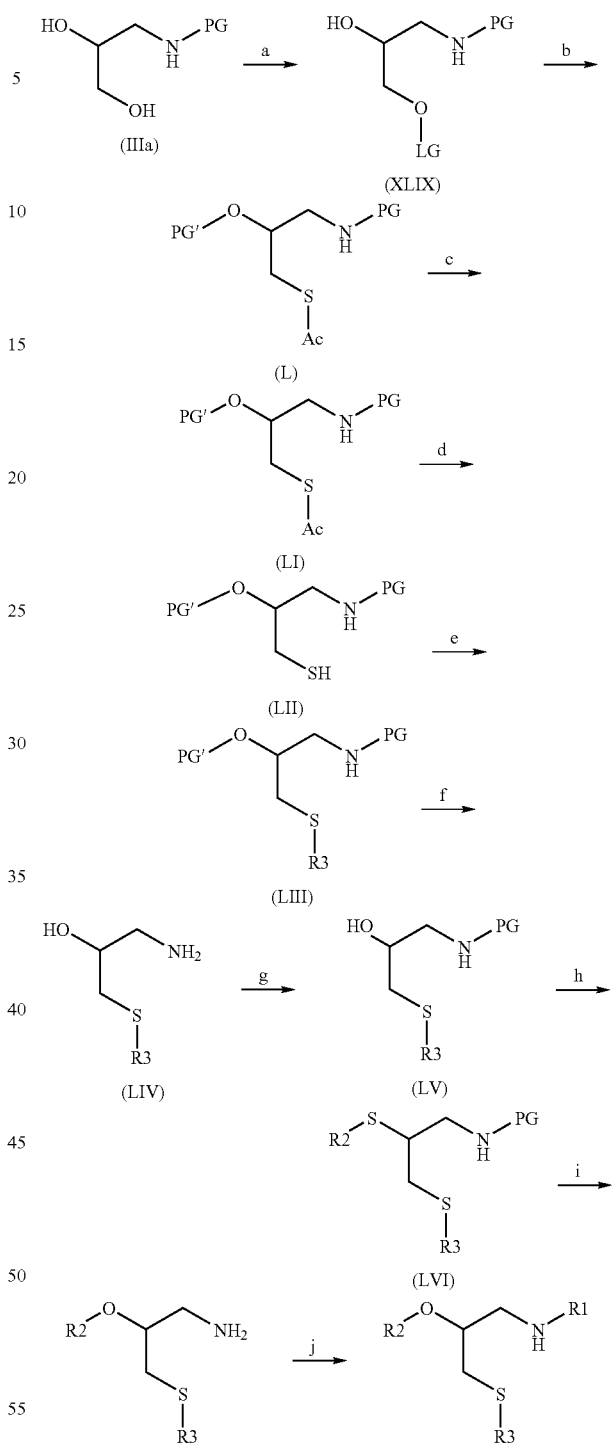

a. activation; b. substitution; c. acylation; d. deprotection; e. acylation; f. deprotection
g: protection; h: acylation; i: deprotection; j: amidification Compounds represented by formula (I) according to the invention in which (i) G2 is an oxygen atom, (ii) G3 is a sulfur atom, (iii) R is a hydrogen atom, (iv) R2 and R3, which are the same, are hydrogen atoms or represent a CO—R5 or CO—$(CH_2)_{2n+1}$—X—R6 group and (v) R1 represents a CO—R5 or CO—$(CH_2)_{2n+1}$—X—R6 group, can be prepared from compounds having formula (IIIa) according to the following method (diagram 13):

a) reacting a compound represented by formula (IIIa) such as defined hereinabove, with a compound corresponding to the formula (LG)2 (in stoichiometric amounts) in which LG is a reactive group selected for example in the group consisting of iodine, bromine, etc., to give a compound represented by general formula (XLIXa);

b) reacting a compound represented by formula (XLIXa) with a compound corresponding to the formula Ac—S⁻ B⁺ in which Ac represents a short acyl group, preferably the acetyl group, and B is a counter-ion selected for example in the group consisting of sodium and potassium, preferably potassium to give the compound represented by general formula (L);

c) deprotecting the sulfur atom of a compound (L), in conditions known to those skilled in the art, to give a compound represented by general formula (LVII);

d) reacting a compound represented by general formula (LVII) with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art to give a compound represented by general formula (LVI) in which R2 and R3 represent a same CO—R5 or CO—$(CH_2)_{2n+1}$—X—R6 group;

e) deprotecting a compound represented by formula (LVI), in conventional conditions known to those skilled in the art, to give a compound represented by general formula (I) in which G2 is an oxygen atom, G3 is a sulfur atom, R and R2 are hydrogen atoms and R2 and R3 represent a same CO—R5 or CO—$(CH_2)_{2n+1}$—X—R6 group;

f) reacting a compound represented by general formula (I) in which G2 is an oxygen atom, G3 is a sulfur atom, R and R2 are hydrogen atoms and R2 and R3 represent a same CO—R5 or CO—$(CH_2)_{2n+1}$—X—R6 group with a compound corresponding to the formula A°-CO-A2 in which A2 is a reactive group selected for example in the group consisting of OH and Cl, and A° is the R5 group or the $(CH_2)_{2n+1}$—X—R6 group, possibly in the presence of coupling agents or activators known to those skilled in the art.

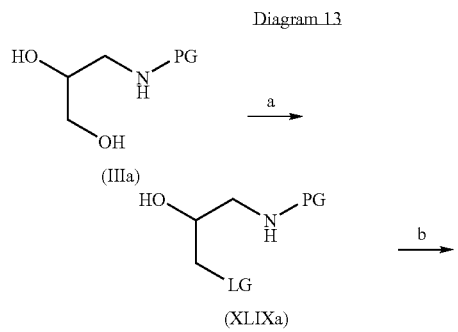

Diagram 13

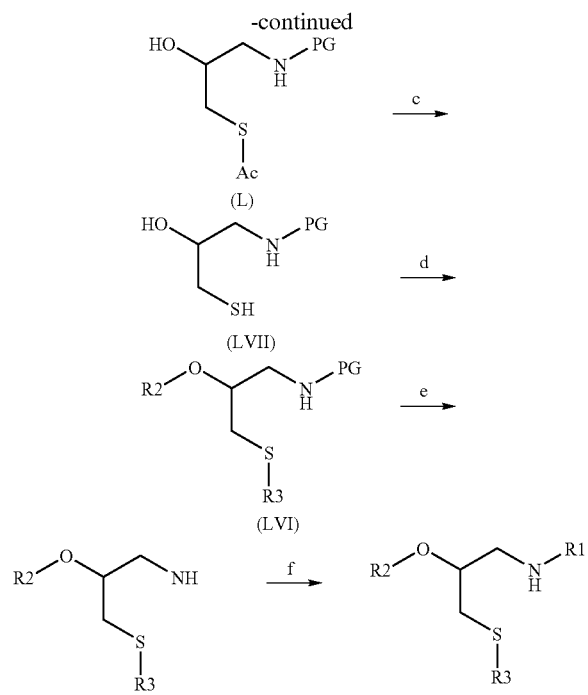

a. activation; B. substitution; c. deprotection; d. acylation; e. deprotection; f. amidification The feasibility, realization and other advantages of the invention are further detailed in the following examples, which are given for purposes of illustration and not by way of limitation.

Legends of Figures:

FIG. 1: Structure of particular inventive compounds the preparation of which is described in examples 2, 4, 5, 6, 8, 10 to 14, 16, 18, 19, 21 and 23 and respectively noted on the figure as 1A.2, 1A.4, 1A.5, 1A.6, 1A.8, 1A.10, 1A.11, 1A.12, 1A.13, 1A.14, 1A.16, 1A.18, 1A.19, 1A.21 and 1A.23.

FIG. 2: Evaluation of the antioxidant properties of the inventive compounds on LDL oxidation by copper (Cu).

FIG. 2a: conjugated diene formation over time or lag phase.

FIG. 2b: rate of diene formation.

FIG. 2c: maximum amount of conjugated dienes formed.

FIG. 3: Evaluation of the PPAR□ agonist properties of the inventive compounds with the Gal4/PPAR□ transactivation system.

EXAMPLES

For easier comprehension of the text, the inventive compounds used in the examples concerning the measurement and evaluation of activity are abbreviated as follows: "Ex 2", for instance, indicates the compound of the invention which preparation is described in example 2.

Thin-layer chromatography (TLC) was carried out on plates coated with MERCK silica gel $60F_{254}$ 0.2 mm thick. Retention factor is abbreviated Rf.

Column chromatography was carried out on silica gel 60 with a particle size of 40-63 µm (Merck reference 9385-5000).

Example 1

Preparation of tetradecylthioacetic acid

Potassium hydroxide (34.30 g, 0.611 mol), mercaptoacetic acid (20.9 ml, 0.294 mol) and 1-bromotetradecane (50 ml, 0.184 mol) were added in that order to methanol (400 ml). The mixture was stirred overnight at room temperature. A concentrated hydrochloric acid solution (60 ml) dissolved in water (800 ml) was then added. The tetradecylthioacetic acid precipitated. The mixture was stirred overnight at room temperature. The precipitate was then filtered, washed five times with water and dried in a dessicator. The product was recrystallized in methanol.

Yield: 94% Rf (dichloromethane/methanol 9:1): 0.60 MP: 67-68° C. IR: $\nu$CO acid 1726 and 1684 cm$^{-1}$ NMR ($^1$H, CDCl$_3$): 0.84-0.95 (t, 3H, —CH$_3$, J=6.5 Hz); 1.20-1.45 (multiplet, 22H, —CH$_2$—); 1.55-1.69 (quint, 2H, —CH$_2$—CH$_2$—S—, J=7 Hz); 2.63-2.72 (t, 2H, CH$_2$—CH$_2$—S—, J=7 Hz); 3.27 (s, 2H, S—CH$_2$—COOH) MS (ESI-MS): M−1=287.

Example 2

Preparation of 3-(tetradecylthioacetylamino)propane-1,2-diol

Tetradecylthioacetic acid (example 1) (14.393 g, 50 mmol) and 3-amino-propane-1,2-diol (5 g, 55 mmol) were placed in a flask and heated at 190° C. for 1 hour. The reaction mixture was cooled to room temperature, taken up in chloroform and washed once with water. The organic phase was dried on magnesium sulfuate, filtered and dried. The residue was stirred in ether and the product was isolated by filtration.

Yield: 22% Rf (dichloromethane/methanol 9:1): 0.60 MP: 89-92° C. IR: $\nu$NH and OH 3282 cm$^{-1}$; $\nu$CO amide 1640 cm$^{-1}$ NMR ($^1$H, CDCl$_3$): 0.89 (t, 3H, —CH$_3$, J=6.5 Hz); 1.26 (multiplet, 22H, —CH$_2$—); 1.57 (m, 2H, —CH$_2$—CH$_2$—S—); 2.54 (t, 2H, —CH$_2$—CH$_2$—S—, J=7.6 Hz); 3.27 (s, 2H, S—CH$_2$—CONH—); 3.47 (m, 2H, —CONH—CH$_2$—CHOH—CH$_2$OH); 3.58 (m, 1H, —CONH—CH$_2$—CHOH—CH$_2$OH); 3.81 (m, 2H, —CONH—CH$_2$—CHOH—CH$_2$OH); 7.33 (sl, 1H, —CONH). MS (MALDI-TOF): M+1=362 (M+H); M+23=385 (M+Na$^+$); M+39=400 (M+K$^+$)

Example 3

3-(palmitoylamino)propane-1,2-diol

This compound was synthesized according to the method described hereinabove (example 2) from 3-amino-propane-1,2-diol and palmitic acid.

Yield: 86% Rf (dichloromethane/methanol 9:1): 0.50 IR: $\nu$NH and OH 3312 cm$^{-1}$; $\nu$CO amide 1633 cm$^{-1}$ MP: 104-108° C. NMR ($^1$H, CDCl$_3$): 0.89 (t, 3H, —CH$_3$, J=6.5 Hz); 1.28 (multiplet, 24H, —CH$_2$—); 1.64 (m, 2H, —CH$_2$—CH$_2$—CO—); 2.24 (m, 2H, —CH$_2$—CH$_2$—CO—); 3.43 (m, 2H, —CONH—CH$_2$—CHOH—CH$_2$OH); 3.55 (m, 2H, —CONH—CH$_2$—CHOH—CH$_2$OH); 3.78 (m, 1H, —CONH—CH$_2$—CHOH—CH$_2$OH); 5.82 (sl, 1H, —CONH—). MS (MALDI-TOF): M+1=330 (M+H)

Example 4

Preparation of 1,2-(dipalmitoyloxy)-3-tetradecylthioacetylaminopropane 3-(tetradecylthioacetylamino)propane-1,2-diol (example 2) (1 g, 2.77 mmol) was dissolved in dichloromethane (200 ml). Dicyclohexylcarbodiimide (1.426 g, 6.91 mmol), dimethylaminopyridine (0.845 g, 6.91 mmol) and palmitic acid (1.773 g, 6.91 mmol) were then added and the mixture was stirred at room temperature for 48 hours. The dicyclohexylurea which precipitated was filtered and washed with dichloromethane. The filtrate was vacuum evaporated. The residue was purified by chromatography on silica gel (eluent: dichloromethane/cyclohexane 6:4) (yield: 28%).

Rf (dichloromethane/cyclohexane 7:3): 0.28 MP: 73-75° C. IR: $\nu$NH 3295 cm$^{-1}$; $\nu$CO ester 1730 cm$^{-1}$; $\nu$CO amide 1663 cm$^{-1}$ NMR ($^1$H, CDC$_3$): 0.89 (t, 9H, —CH$_3$, J=6.5 Hz); 1.26 (multiplet, 70H, —CH$_2$—); 1.57 (multiplet, 6H, —CH$_2$—CH$_2$—S— and OCOCH$_2$—CH$_2$); 2.33 (t, 4H, OCOCH$_2$—CH$_2$—, J=7.3 Hz); 2.51 (t, 2H, CH$_2$—CH$_2$—S—, J=7.3 Hz); 3.22 (s, 2H, S—CH$_2$—CONH—); 3.47 (m, 1H, —CONH—CHaHb-CH—CHcHd-); 3.62 (m, 1H, —CONH—CHaHb-CH—CHcHd); 4.12 (dd, 1H, —CHaHb-CH—CHcHd-, J=12.1 Hz and J=5.7 Hz); 4.36 (dd, 1H, —CHaHb-CH—CHcHd-, J=12.1 Hz and J=4.4 Hz); 5.15 (m, 1H, —CHaHb-CH—CHaHb); 7.20 (m, 1H, —NHCO—). MS (MALDI-TOF): M+1=838 (M+H); M+23=860 (M+Na$^+$); M+39=876 (M+K$^+$)

Example 5

Preparation of 1,2-(ditetradecylthioacetyloxy)-3-tetradecylthioacetylaminopropane This compound was synthesized according to the method described hereinabove (example 4) from 3-(tetradecylthioacetylamino)propane-1,2-diol (example 2) and tetradecylthioacetic acid (example 1).

Yield: 41% Rf (dichloromethane): 0.23 IR: $\nu$NH 3308 cm$^{-1}$; $\nu$CO ester 1722 and 1730 cm$^{-1}$; $\nu$CO amide 1672 cm$^{-1}$ MP: 65-67° C. NMR ($^1$H, CDCl$_3$): 0.89 (t, 9H, —CH$_3$, J=6.4 Hz); 1.26 (multiplet, 66H, —CH$_2$—); 1.59 (multiplet, 6H, —CH$_2$—CH$_2$—S—); 2.53 (t, 2H, —CH$_2$—CH$_2$—S—CH$_2$—CONH—, J=7.3 Hz); 2.64 (t, 4H, CH$_2$—CH$_2$—S—CH$_2$—COO—, J=7.3 Hz); 3.23 (s, 4H, S—CH$_2$—COO—); 3.24 (s, 2H, S—CH$_2$—CONH—); 3.52 (m, 1H, —CONH—CHaHb-CH—CHcHd-); 3.67 (m, 1H, —CONH—CHaHb-CH—CHcHd-); 4.22 (dd, 1H, —CHaHb-CH—CHcHd-, J=12.2 Hz and J=5.4 Hz); 4.36 (dd, 1H, —CHaHb-CH—

---

Melting points (MP) were determined on a Buchi B 540 apparatus by the capillary method.

Infrared (IR) spectra were recorded on a Bruker Fourier transformation spectrometer (Vector 22).

Nuclear magnetic resonance (NMR) spectra were recorded on a Bruker AC 300 spectrometer (300 MHz). Each signal was identified by its chemical shift, intensity, multiplicity (noted s for singlet, sl for broad singlet, d for doublet, dd for split doublet, t for triplet, td for split triplet, quint for quintuplet and m for multiplet) and its coupling constant (J).

Mass spectra (MS) were determined on a Perkin Elmer Sciex API 1 (ESI-MS for ElectroSpray Ionization Mass Spectrometry) or on an Applied Biosystems Voyager DE-STR of the MALDI-TOF type (Matrix-Assisted Laser Desorption/Ionization—Time Of Flight).

CHcHd-, J=12.2 Hz and J=3.9 Hz); 5.19 (m, 1H, —CHaHb-CH—CHaHb-); 7.18 (m, 1H, —NHCO—). MS (MALDI-TOF): M+1=902 (M+H); M+23=924 (M+Na$^+$); M+39=940 (M+K$^+$)

Example 6

Preparation du 1,2-(ditetradecylthioacetyloxy)-3-palmitoylaminopropane

This compound was synthesized according to the method described hereinabove (example 4) from 3-(palmitoylamino)propane-1,2-diol (example 3) and tetradecylthioacetic acid (example 1).

Yield: 8% Rf (ethyl acetate/cyclohexane 2:8): 0.33 IR: νNH 3319 cm$^{-1}$; νCO ester 1735 cm$^{-1}$; νCO amide 1649 cm$^{-1}$ MP: 82-83° C. NMR ($^1$H, CDCl$_3$): 0.89 (t, 9H, —CH$_3$, J=6.4 Hz); 1.26 (multiplet, 68H, —CH$_2$—); 1.60 (multiplet, 6H, —CH$_2$—CH$_2$—S— and —CH$_2$—CH$_2$—CONH—); 2.18 (t, 2H, —CH$_2$—CH$_2$—CONH—, J=6.8 Hz); 2.64 (multiplet, 4H, CH$_2$—CH$_2$—S—CH$_2$—COO—); 3.22 (s, 2H, —S—CH$_2$—COO—); 3.24 (s, 2H, —S—CH$_2$—COO—); 3.47 (m, 1H, —CONH—CHaHb-CH—CHcHd-); 3.62 (m, 1H, —CONH—CHaHb-CH—CHcHd-); 4.23 (dd, 1H, —CHaHb-CH—CHcHd-, J=11.9 Hz and J=5.6 Hz); 4.36 (dd, 1H, —CHaHb-CH—CHcHd-, J=12.2 Hz and J=4 Hz); 5.15 (m, 1H, —CHaHb-CH—CHaHb-); 5.85 (m, 1H, —NHCO—). MS (MALDI-TOF): M+1=870 (M+H)

Example 7

Preparation of 1,3-di(oleylamino)propan-2-ol

Oleic acid (5.698 g, 0.020 mol) and 1,3-diaminopropan-2-ol (1 g, 0.011 mol) were placed in a flask and heated at 190° C. for 2 hours. The reaction mixture was cooled to room temperature, then taken up in chloroform and washed with water. The aqueous phase was extracted with chloroform and the organic phases were combined, dried on magnesium sulfate, filtered and evaporated to dryness to yield an oily black residue (6.64 g) which was purified by chromatography on silica gel (eluent: dichloromethane/methanol 99:1). The resulting product was then washed with ether and filtered.

Yield: 23% Rf (dichloromethane/methanol 95:5): 0.43 IR: νNH 3306 cm$^{-1}$; νCO amide 1646 and 1630 cm$^{-1}$ MP: 88-92° C. NMR ($^1$H, CDCl$_3$): 0.89 (t, 6H, —CH$_3$, J=6.2 Hz); 1.28 (multiplet, 68H, —CH$_2$—); 1.61-1.66 (multiplet, 4H, —CH$_2$—CH$_2$—CONH—); 1.98-2.02 (multiplet, 8H, —CH$_2$—CH=CH—CH$_2$—); 2.23 (t, 4H, —CH$_2$—CH$_2$—CONH—, J=7.0 Hz); 3.25-3.42 (multiplet, 4H, —CONH—CH$_2$—CH—CH$_2$—); 3.73-3.80 (m, 1H, —CONH—CH$_2$—CH—CH$_2$—); 5.30-5.41 (multiplet, 4H, —CH$_2$—CH=CH—CH$_2$—); 6.36 (multiplet, 2H, —NHCO—). MS (MALDI-TOF): M+1=619 (M+H$^+$); M+23=641 (M+Na$^+$); M+39=657 (M+K$^+$)

Example 8

Preparation of 1,3-di(tetradecylthioacetylamino)propan-2-ol

This compound was synthesized according to the method described hereinabove (example 7) from 1,3-diaminopropan-2-ol and tetradecylthioacetic acid (example 1).

Yield: 94% Rf (dichloromethane/methanol 95:5): 0.44 IR: νNH 3275 cm$^{-1}$; νCO amide 1660 and 1633 cm$^{-1}$ MP: 101-104° C. NMR ($^1$H, CDCl$_3$): 0.89 (t, 6H, —CH$_3$, J=6.3 Hz); 1.28 (multiplet, 44H, —CH$_2$—); 1.57-1.62 (multiplet, 4H, —CH$_2$—CH$_2$—S—CH$_2$—CONH—); 2.55 (t, 4H, —CH$_2$—CH$_2$—S—CH$_2$—CONH—, J=7.2 Hz); 3.26 (s, 4H, —S—CH$_2$—CONH—); 3.32-3.36 (multiplet, 2H, —CONH—CH$_a$H$_b$-CH—CH$_a$H$_b$—NHCO—); 3.43-3.49 (multiplet, 2H, —CONH—CH$_a$H$_b$—CH—CH$_a$H$_b$—NHCO—); 3.82-3.84 (m, 1H, —CONH—CH$_2$—CH—CH$_2$—NHCO—); 7.44 (sl, 2H, —NHCO). MS (MALDI-TOF): M+23=653 (M+Na$^+$); M+39=669 (M+K$^+$)

Example 9

Preparation of 1,3-di(stearoylamino)propan-2-ol

This compound was synthesized according to the method described hereinabove (example 7) from 1,3-diaminopropan-2-ol and stearic acid.

Yield: 73% Rf (dichloromethane/methanol 95:5): 0.28 IR: νNH 3306 cm$^{-1}$; νCO amide 1647 and 1630 cm$^{-1}$ MP: 123-130° C. MS (MALDI-TOF): M+23=645 (M+Na$^+$)

Example 10

Preparation of 1,3-diamino-2-(tetradecylthioacetyloxy)propane dihydrochloride

Preparation of 1,3-di(tert-butyloxycarbonylamino)propan-2-ol (example 10a)

1,3-diaminopropan-2-ol (3 g, 0.033 mol) was dissolved in methanol (300 ml) followed by the addition of triethylamine (33 ml dropwise) and di-tert-butyl dicarbonate [(BOC)$_2$O] (21.793 g, 0.100 mol). The reaction medium was heated at 40-50° C. for 20 min then stirred at room temperature for 1 hour. After evaporation of the solvent, the colorless oil residue was purified by chromatography on silica gel (eluent: dichloromethane/methanol 95:5). The reaction yielded a colorless oil which crystallized slowly.

Yield: quantitative Rf (dichloromethane/methanol 95:5): 0.70 IR: νNH 3368 cm$^{-1}$; νCO carbamate 1690 cm$^{-1}$ MP: 98-100° C. NMR ($^1$H, CDCl$_3$): 1.45 (multiplet, 18H, —CH$_3$— (BOC)); 3.02 (sl, 1H, OH); 3.15-3.29 (multiplet, 4H, BOCNH—CH$_2$—CH—CH$_2$—NHBOC); 3.75 (m, 1H, BOCNH—CH$_2$—CH—CH$_2$—NHBOC); 5.16 (multiplet, 2H, —NHBOC). MS (MALDI-TOF): M+1=291 (M+H$^+$); M+23=313 (M+Na$^+$); M+39=329 (M+K$^+$)

Preparation of 1,3-di(tert-butyloxycarbonylamino)-2-(tetradecylthioacetyloxy)-propane (example 10b)

1,3-(di-tert-butoxycarbonylamino)-propan-2-ol (example 10a) (1 g, 3.45 mmol), tetradecylthioacetic acid (example 1) (0.991 g, 3.45 mmol) and dimethylaminopyridine (0.042 g, 0.34 mmol) were dissolved in dichloromethane (40 ml) at 0° C. Dicyclohexylcarbodiimide (0.709 g, 3.45 mmol) diluted in dichloromethane was then added dropwise and the mixture was stirred at 0° C. for 30 min, then brought to room temperature. After 20 hours of reaction, the dicyclohexylurea precipitate was filtered and the filtrate was dried. The oily residue was purified by chromatography on silica gel (eluent dichloromethane/cyclohexane 5:5 followed by dichloromethane/ethyl acetate 98:2).

Yield: 52% Rf (dichloromethane/ethyl acetate 95:5): 0.43 IR: νNH 3369 cm$^{-1}$; νCO carbamate 1690 cm$^{-1}$; νCO ester 1719 cm$^{-1}$ NMR ($^1$H, CDCl$_3$): 0.89 (t, 3H, CH$_3$, J=6.3 Hz); 1.26 (multiplet, 22H, —CH$_2$—); 1.45 (multiplet, 18H, —CH$_3$— (BOC)); 1.56-1.66 (m, 2H, —CH$_2$—CH$_2$—S—CH$_2$—CO); 2.64 (t, 2H, —CH$_2$—CH$_2$—S—CH$_2$—CO, J=7.5 Hz); 3.20 (s, 2H, CH$_2$—S—CH$_2$—CO); 3.35 (multiplet, 4H, BOCNH—CH$_2$—CH—CH$_2$—NHBOC); 4.89 (m, 1H, BOCNH—CH$_2$—CH—CH$_2$—NHBOC); 5.04 (multiplet, 2H, —NHBOC). MS (MALDI-TOF): M+23=583 (M+Na$^+$); M+39=599 (M+K$^+$)

Preparation of 1,3-diamino-2-(tetradecylthioacetyloxy)propane dihydrochloride (example 10)

1,3-(ditert-butoxycarbonylamino)-2-tetradecylthioacetyloxypropane (example 10b) (0.800 g, 1.43 mmol) was dissolved in diethyl ether (50 ml) saturated with gaseous hydrochloric acid. The reaction medium was stirred at room temperature for 20 hours. The precipitate which formed was then filtered and washed with ether.

Yield: 88% Rf (dichloromethane/methanol 7:3): 0.37 IR: vNH$_2$ 3049 and 3099 cm$^{-1}$; vCO ester 1724 cm$^{-1}$ MP: 224° C. (decomposition) NMR ($^1$H, CDCl$_3$): 0.86 (t, 3H, CH$_3$, J=6.3 Hz); 1.24 (multiplet, 22H, —CH$_2$—); 1.48-1.55 (m, 2H, —CH$_2$—CH$_2$—S—CH$_2$—CO); 2.57 (t, 2H, —CH$_2$—CH$_2$—S—CH$_2$—CO, J=7.2 Hz); 3.16 (multiplet, 4H, BOCNH—CH$_2$—CH—CH$_2$—NH); 3.56 (s, 2H, CH$_2$—S—CH$_2$—CO); 5.16 (m, 1H, BOCNH—CH$_2$—CH—CH$_2$—NH); 8.43 (multiplet, 6H, —NH$_2$.HCl). MS (MALDI-TOF): M+1=361 (M+H$^+$); M+23=383 (M+Na$^+$); M+39=399 (M+K$^+$)

Example 11

Preparation of 1,3-ditetradecylthioacetylamino-2-(tetradecylthioacetyloxy)propane 1,3-diamino-2-tetradecylthioacetyloxypropane dihydrochloride (example 10) (0.400 g, 0.92 mmol) and tetradecylthioacetic acid (example 1) (0.532 g, 1.84 mmol) were dissolved in dichloromethane (50 ml) at 0° C. followed by the addition of triethylamine (0.3 ml, 2.1 mmol), dicyclohexylcarbodiimide (0.571 g, 2.77 mmol) and hydroxybenzotriazole (HOBt) (0.249 g, 1.84 mmol). The reaction medium was stirred at 0° C. for 1 hour then brought to room temperature for 48 hours. The dicyclohexylurea precipitate was filtered and washed with dichloromethane. The filtrate was vacuum evaporated. The residue obtained (1.40 g) was purified by chromatography on silica gel (eluent: dichloromethane followed by dichloromethane/ethyl acetate 9:1).

Yield: 74% Rf (dichloromrthane/ethyl acetate 8:2): 0.25 IR: vNH 3279, 3325 cm$^{-1}$; vCO ester 1731 cm$^{-1}$; vCO amide 1647, 1624 cm$^{-1}$ MP: 87-89° C. NMR ($^1$H, CDCl$_3$): 089 (t, 9H, CH$_3$, J=6.6 Hz); 1.26 (multiplet, 66H, —CH$_2$—); 1.55-1.60 (multiplet, 6H, —CH$_2$—CH$_2$—S—CH$_2$—CO); 2.55 (t, 4H, —CH$_2$—CH$_2$—S—CH$_2$—CONH—, J=7.2 Hz); 2.65 (t, 2H, —CH$_2$—CH$_2$—S—CH$_2$—COO—, J=7.2 Hz); 3.21 (s, 2H, —CH$_2$—S—CH$_2$—COO—); 3.25 (s, 4H, —CH$_2$—S—CH$_2$—CONH—); 3.40-3.49 (m, 2H, —CONH—CH$_a$H$_b$—CH—CH$_a$H$_b$—NHCO—); 3.52-3.61 (m, 2H, —CONH—CH$_a$H$_b$—CH—CH$_a$H$_b$—NHCO—); 4.96 (m, 1H, —CONH—CH$_2$—CH—CH$_2$—NHCO—); 7.42 (multiplet, 2H, —NHCO—). MS (MALDI-TOF): M+1=901 (M+H$^+$); M+23=923 (M+Na$^+$); M+39=939 (M+K$^+$)

Example 12

Preparation of 1,3-dioleylamino-2-(tetradecylthioacetyloxy)propane

This compound was synthesized according to the method described in example 11 from 1,3-diamino-2-tetradecylthioacetyloxypropane dihydrochloride (example 10) and oleic acid.

Yield: 15% Rf (dichloromethane/ethyl acetate 8:2): 0.38 IR: vNH 3325 cm$^{-1}$; vCO ester 1729 cm$^{-1}$; vCO amide 1640 and 1624 cm$^{-1}$ MP: 57-59° C. NMR ($^1$H, CDCl$_3$): 0.89 (t, 9H, CH$_3$, J=6.6 Hz); 1.26 (multiplet, 62H, —CH$_2$—); 1.59-1.74 (multiplet, 6H, —CH$_2$—CH$_2$—S—CH$_2$—CO); 1.92-2.03 (multiplet, 8H, —CH$_2$—CH=CH—CH$_2$—); 2.22 (t, 4H, —CH$_2$—CH$_2$—S—CH$_2$—CONH—, J=7.2 Hz); 2.65 (t, 2H, —CH$_2$—CH$_2$—S—CH$_2$—COO—, J=7.4 Hz); 3.19 (s, 2H, —CH$_2$—S—CH$_2$—COO—); 3.25-3.34 (m, 2H, —CONH—CH$_a$H$_b$—CH—CH$_a$H$_b$—NHCO—); 3.56-3.65 (m, 2H, —CONH—CH$_a$H$_b$—CH—CH$_a$H$_b$—NHCO—); 4.87 (m, 1H, —CONH—CH$_2$—CH—CH$_2$—NHCO—); 5.34 (multiplet, 4H, —CH$_2$—CH=CH—CH$_2$—); 6.27 (multiplet, 2H, —NHCO—). MS (MALDI-TOF): M+1=889 (M+H$^+$); M+23=912 (M+Na$^+$)

Example 13

Preparation of 2,3-ditetradecylthioacetylaminopropan-1-ol

Preparation of methyl 2,3-diaminopropanoate dihydrochloride (example 13a)

2,3-diaminopropionic acid hydrochloride (1 g, 7 mmol) was dissolved in methanol (40 ml). The medium was cooled in an ice bath, followed by the addition of thionyl chloride (2.08 ml, 28 mmol). The medium was brought to room temperature then refluxed for 20 hours. The solvent was evaporated and the residue was triturated in heptane. The resulting precipitate was filtered, washed and dried to give a yellowish-white solid.

Yield: 94% Rf: (dichloromethane/methanol 9:1): 0.03 IR: vNH$_2$ 2811 cm$^{-1}$; vCO ester 1756 cm$^{-1}$ MP: 170-180° C. (decomposition) NMR ($^1$H, CDCl$_3$): 3.78 (s, 3H, —CH$_3$); 4.33 (m, 3H, —CH$_2$— and —CH—); 8.77 (m, 3H, —NH$_2$.HCl); 9.12 (m, 3H, —NH$_2$.HCl)

Preparation of methyl 2,3-ditetradecylthioacetylaminopropanoate (example 13b)

Methyl 2,3-diaminopropanoate dihydrochloride (example 13a) (0.500 g, 2.62 mmol) and tetradecylthioacetic acid (example 1) (1.51 g, 5.23 mmol) were dissolved in dichloromethane (80 ml) at 0° C. followed by the addition of triethylamine (0.79 ml), dicyclohexylcarbodiimide (1.62 g, 7.85 mmol) and hydroxybenzotriazole (0.707 g, 5.23 mmol). The reaction medium was stirred at 0° C. for 1 hour then brought to room temperature for 48 hours. The dicyclohexylurea precipitate was filtered and washed with dichloromethane and the filtrate was evaporated. The residue obtained (3.68 g) was purified by chromatography on silica gel (eluent: dichloromethane/ethyl acetate 95:5) to give the desired compound in the form of a white powder.

Yield: 96% Rf: (dichloromethane/methanol 98:2): 0.63 IR: vNH amide 3276 cm$^{-1}$; vCO ester 1745 cm$^{-1}$; vCO amide 1649 cm$^{-1}$ MP: 81.5-82.5° C. NMR ($^1$H, CDCl$_3$):

0.89 (t, 6H, CH$_3$, J=6.6 Hz); 1.26-1.37 (multiplet, 44H, —CH$_2$—); 1.56-1.61 (m, 4H, —CH$_2$—CH$_2$—S—CH$_2$—CONH); 2.50-2.60 (m, 4H, —CH$_2$—CH$_2$—S—CH$_2$—CONH—); 3.22 (s, 2H, —CH$_2$—S—CH$_2$—CONH—); 3.25 (s, 2H, —CH$_2$—S—CH$_2$—CONH—); 3.74 (m, 2H, H$_3$CO (CO)—CH—CH$_2$—NHCO—); 3.79 (s, 3H, —COOCH$_3$); 4.64-4.70 (m, 1H, H$_3$CO(CO)—CH—CH$_2$—NHCO—); 7.79 (d, 2H, —NHCO—, J=7.3 Hz). MS (MALDI-TOF): M+1=659 (M+H$^+$); M+23=681 (M+Na$^+$); M+39=697 (M+K$^+$)

Preparation of 2,3-ditetradecylthioacetylaminopropan-1-ol (example 13)

Sodium borohydride (316 mg, 8.4 mmol) was dissolved in tetrahydrofuran (40 ml). The reaction mixture was cooled in an ice bath followed by the addition of methyl 2,3-ditetradecylthioacetylaminopropanoate (example 13b) (500 mg, 0.76 mmol) in small portions. The mixture was brought to room temperature and stirred. After 4 days of reaction, 20 ml of water were added. The product, which precipitated, was filtered, washed with water then dried in a dessicator to give a white powder.

Yield: 76% Rf: (dichloromethane/methanol 95:5): 0.53 IR: νOH alcohol 3436 cm$^{-1}$; νNH amide 3313 and 3273 cm$^{-1}$; νCO amide 1648 and 1622 cm$^{-1}$ MP: 100.2-102.2° C. NMR ($^1$H, CDCl$_3$): 0.89 (t, 6H, CH$_3$, J=6.2 Hz); 1.26 (multiplet, 44H, —CH$_2$—); 1.59 (m, 4H, —CH$_2$—CH$_2$—S—CH$_2$—CONH); 2.50-2.56 (m, 4H, —CH$_2$—CH$_2$—S—CH$_2$—CONH—); 3.23 (s, 2H, —CH$_2$—S—CH$_2$—CONH—); 3.27 (s, 2H, —CH$_2$—S—CH$_2$—CONH—); 3.50-3.91 (multiplet, 5H, —OCO—CH$_2$—CH—CH$_2$—NHCO—); 7.38 (d, 2H, —NHCO—, J=7.1 Hz). MS (MALDI-TOF): M+1=631 (M+H$^+$); M+23=653 (M+Na$^+$); M+39=669 (M+K$^+$)

Example 14

Preparation of 2,3-ditetradecylthioacetylamino-1-tetradecylthioacetyloxypropane 2,3-ditetradecylthioacetylaminopropan-1-ol (example 13) (0.200 g, 0.32 mmol) was dissolved in tetrahydrofuran (40 ml) followed by the addition of dicyclohexylcarbodiimide (65 mg, 0.32 mmol), dimethylaminopyridine (39 mg, 0.32 mmol) and tetradecylthioacetic acid (example 1) (91 mg, 0.32 mmol). The mixture was stirred at room temperature for 20 hours. The dicyclohexylurea precipitate was filtered, washed with tetrahydrofuran and the filtrate was evaporated. The residue obtained (1 g) was purified by flash chromatography (eluent:dichloromethane) to produce the desired compound in the form of a white powder.

Yield: 59% Rf: (dichloromethane/ethyl acetate 8:2): 0.49 IR: νNH amide 3281 cm$^{-1}$; νCO ester 1736 cm$^{-1}$; νCO amide 1641 cm$^{-1}$ MP: 95.4-97.3° C. NMR ($^1$H, CDCl$_3$): 0.89 (t, 9H, CH$_3$, J=6.4 Hz); 1.27-1.34 (multiplet, 66H, —CH$_2$—); 1.54-163 (m, 6H, —CH$_2$—CH$_2$—S—CH$_2$—CO—); 2.53 (t, 4H, —CH$_2$—CH$_2$—S—CH$_2$—CONH—, J=7.2 Hz); 2.65 (t, 2H, —CH$_2$—CH$_2$—S—CH$_2$—COO—, J=7.2 Hz); 3.21 (s, 2H, —CH$_2$—S—CH$_2$—CONH—); 3.23 (s, 2H, —CH$_2$—S—CH$_2$—CONH—); 3.25 (s, 2H, —CH$_2$—S—CH$_2$—COO—); 3.46-3.56 (m, 2H, —OCO—CH$_2$—CH—CH$_2$—NHCO—); 4.22-4.25 (m, 2H, —OCO—CH$_2$—CH—CH$_2$—NHCO—); 4.29-4.39 (m, 1H, —OCO—CH$_2$—CH—CH$_2$—NHCO—); 7.29 (t, 1H, —NHCO—); 7.38 (d, 1H, —NHCO—, J=7.6 Hz). MS (MALDI-TOF): M+1=901 (M+H$^+$)

Example 15

Preparation of 1,3-diamino-2-(tetradecylthioacetylthio)propane dihydrochloride

Preparation of 1,3-di(tert-butyloxycarbonylamino)-2-(p-toluenesulfonyloxy)propane (example 15a)

1,3-di(tert-butyloxycarbonylamino)propan-2-ol (example 10a) (2.89 g, 10 mmol) and triethylamine (2.22 ml, 16 mmol) were dissolved in anhydrous dichloromethane (100 ml). The reaction mixture was cooled in an ice bath followed by dropwise addition of tosyl chloride (2.272 g, 12 mmol) dissolved in dichloromethane (30 ml). The reaction mixture was then stirred at room temperature for 72 hours. One equivalent of chloride and 1.6 of triethylamine were added after 48 hours. Water was added to stop the reaction and the medium was allowed to settle. The organic phase was washed several times with water. The aqueous phases were combined and extracted again with dichloromethane. The organic phase was dried on magnesium sulfate, filtered and the solvent was evaporated. The residue obtained (6.44 g) was purified by chromatography on silica gel (eluent:dichloromethane followed by dichloromethane/methanol 99:1) to yield the desired compound as a white solid.

Yield: 48% Rf (dichloromethane/methanol 98:2): 0.70 IR: νNH 3400 cm$^{-1}$; νCO ester 1716 cm$^{-1}$; νCO carbamate 1689 cm$^{-1}$ MP: 104-111° C. NMR ($^1$H, CDCl$_3$): 1.42 (s, 18H, CH$_3$ (BOC)); 2.46 (s, 3H, CH$_3$); 3.22 and 3.41 (multiplet, 4H, BOCNH—CH$_2$—CH—CH$_2$—NHBOC); 4.56 (m, 1H, BOCNH—CH$_2$—CH—CH$_2$—NHBOC); 5.04-5.11 (multiplet, 2H, —NHBOC); 7.36 (d, 2H, aromatics, J=8.5 Hz); 7.36 (d, 2H, aromatics, J=8.5 Hz). MS (MALDI-TOF): M+23=467 (M+Na$^+$); M+39=483 (M+K$^+$)

Preparation of 1,3-di(tert-butyloxycarbonylamino)-2-acetylthiopropane (example 15b)

1,3-(ditert-butoxycarbonylamino)-2-(p-toluenesulfonyloxy)propane (example 15a) (0.500 g, 1.12 mmol) and potassium thioacetate (0.161 g, 1.41 mmol) were dissolved in acetone and the medium was refluxed for 48 hours. One equivalent of potassium thioacetate was added after 24 hours of reflux. The reaction was brought to room temperature and the solvent evaporated. The residue was taken up in diethyl ether and filtered on Celite®. The filtrate was evaporated. The product obtained (0.48 g) was purified by chromatography on silica gel (eluent: dichloromethane/ethyl acetate 98:2) to give the desired compound as an ochre solid.

Yield: 84% Rf (dichloromethane/methanol 98:2): 0.45 IR: νNH 3350 cm$^{-1}$; νCO ester 1719 cm$^{-1}$; νCO carbamate 1691 cm$^{-1}$ MP: 93-96° C. NMR ($^1$H, CDCl$_3$): 1.45 (s, 18H, CH$_3$ (BOC)); 2.34 (s, 3H, CH$_3$); 3.23-3.32 (m, 2H, BOCNH—CH$_a$H$_b$—CH—CH$_a$H$_b$—NHBOC); 3.38-3.43 (m, 2H, BOCNH—CH$_a$H$_b$—CH—CH$_a$H$_b$—NHBOC); 3.58-3.66 (m, 1H, BOCNH—CH$_2$—CH—CH$_2$—NHBOC); 5.22 (multiplet, 2H, —NHBOC). MS (MALDI-TOF): M+23=371 (M+Na$^+$)

Preparation of 1,3-di(tert-butyloxycarbonylamino)-2-mercantopropane (example 15c)

1,3-di(tert-butoxycarbonylamino)-2-(acetylthio)propane (example 15b) (0.380 g, 1,2 mmol) diluted in methanol (10 ml) was added to a 20% potassium carbonate solution in methanol (2.14 ml, 12.4 mmol), deoxygenated under a stream of nitrogen. The reaction mixture was stirred under nitrogen at room temperature for 20 hours, then acidified to pH 6 with acetic acid. The solvents were vacuum evaporated. The residue was taken up in water and extracted with chloroform. The organic phases were combined, dried on magnesium sulfate, then filtered and dried to give the desired product in the form of a white solid which was promptly used in the next reaction.

Yield: 90% Rf (dichloromethane/methanol 98/2): 0.56 IR: $\nu$NH 3370 cm$^{-1}$; $\nu$CO carbamate 1680 cm$^{-1}$ NMR ($^1$H, CDCl$_3$): 1.46 (s, 18H, CH$_3$ (BOC)); 2.98-3.12 (multiplet, 3H, BOCNH—CH$_a$H$_b$—CH—CH$_a$H$_b$—NHBOC and BOCNH—CH$_2$—CH—CH$_2$—NHBOC); 3.46-3.50 (m, 2H, BOCNH—CH$_a$H$_b$—CH—CH$_a$H$_b$—NHBOC); 5.27 (multiplet, 2H, —NHBOC).

Preparation of 1,3-di(tert-butyloxycarbonylamino)-2-(tetradecylthioacetylthio)propane (example 15d)

1,3-[di(tert-butoxycarbonylamino)]-2-mercaptopropane (example 15c) (0.295 g, 0.963 mmol) was dissolved in dichloromethane (40 ml). Dicyclohexylcarbodiimide (0.199 g, 0.963 mmol), dimethylaminopyridine (0.118 g, 0.963 mmol) and tetradecylthioacetic acid (example 1) (0.278 g, 0.963 mmol) were then added. The reaction mixture was stirred at room temperature and the progress of the reaction was monitored by TLC. After 20 hours of reaction, the dicyclohexylurea precipitate was filtered, washed with dichloromethane and the filtrate was evaporated. The residue obtained (0.73 g) was purified by chromatography on silica gel (eluent:dichloromethane) to give the desired comopund in the form of a white powder.

Yield: 72% Rf (dichloromethane/ethyl acetate 95:5): 0.29 IR: $\nu$NH 3328 cm$^{-1}$; $\nu$CO thioester 1717 cm$^{-1}$; $\nu$CO carbamate 1687 cm$^{-1}$ MP: 47-51° C. NMR ($^1$H, CDCl$_3$): 0.88 (t, 9H, CH$_3$, J=6.1 Hz); 1.26 (multiplet, 22H, —CH$_2$—); 1.44 (s, 18H, CH$_3$ (BOC)); 1.53-1.65 (m, 2H, —CH$_2$—CH$_2$—S—CH$_2$—CO); 2.59 (t, 2H, —CH$_2$—CH$_2$—S—CH$_2$—COS—, J=7.8 Hz); 3.21-3.30 (m, 2H, BOCNH—CH$_a$H$_b$—CH—CH$_a$H$_b$—NHBOC); 3.40 (s, 2H, CH$_2$—S—CH$_2$—COS—); 3.42-3.49 (m, 2H, BOCNH—CH$_a$H$_b$—CH—CH$_a$H$_b$—NHBOC); 3.62-3.65 (m, 1H, BOCNH—CH$_2$—CH—CH$_2$—NHBOC); 5.24 (multiplet, 2H, —NHBOC). MS (MALDI-TOF): M+23=599 (M+Na$^+$); M+39=615 (M+K$^+$)

Preparation of 1,3-diamino-2-(tetradecylthioacetylthio)propane dihydrdochloride (example 15)

1,3-[di(tert-butoxycarbonylamino)]-2-tetradecylthioacetylthiopropane (example 15d) (0.300 g, 0.52 mmol) was dissolved in ether saturated in gaseous hydrochloric acid (55 ml). The mixture was stirred at room temperature. After 96 hours of reaction, the precipitate which formed was filtered, washed several times with diethyl ether and dried to give the desired compound in the form of a white powder.

Yield: 59% Rf (dichloromethane/methanol 9:1): 0.11 IR: $\nu$NH.HCl 2700-3250 cm$^{-1}$; $\nu$CO thioester 1701 cm$^{-1}$ MP: 181° C. (decomposition) NMR ($^1$H, CDCl$_3$): 0.86 (t, 3H, CH$_3$, J=6 Hz); 1.24 (multiplet, 22H, —CH$_2$—); 1.49-1.54 (m, 2H, —CH$_2$—CH$_2$—S—CH$_2$—CO); 2.59 (m, 2H, —CH$_2$—CH$_2$—S—CH$_2$—COS—); 2.80-2.84 (m, 1H, BOCNH—CH$_a$H$_b$—CH—CH$_a$H$_b$—NHBOC); 3.03-3.09 (m, 1H, BOCNH—CH$_a$H$_b$—CH—CH$_a$H$_b$—NHBOC); 3.14 (s, 2H, CH$_2$—S—CH$_2$—COS—); 3.27-3.38 (m, 2H, BOCNH—CH$_a$H$_b$—CH—CH$_a$H$_b$—NHBOC); 3.86-3.90 (m, 1H, BOCNH—CH$_2$—CH—CH$_2$—NHBOC); 8.21 and 8.52 (2m, 2H+4H, NH$_2$.HCl).

Example 16

Preparation of 1,3-ditetradecylthioacetylamino-2-(tetradecylthioacetylthio)propane 1,3-diamino-2-tetradecylthioacetylthiopropane dihydrochloride (example 15) (100 mg, 0.225 mmol) and tetradecylthioacetic acid (example 1) (130 mg, 0.450 mmol) were dissolved in dichloromethane (30 ml) at 0° C. followed by the addition of triethylamine (68 µl), dicyclohexylcarbodiimide (139 mg, 0.675 mmol) and hydroxybenzotriazole (61 mg, 0.450 mmol). The reaction mixture was stirred at 0° C. for 1 hour then brought to room temperature for 48 hours. The dicyclohexylurea precipitate was filtered and washed with dichloromethane and the filtrate was evaporated. The residue obtained (430 mg) was purified by chromatography on silica gel (eluent: dichloromethane/ethyl acetate 95:5) to give the desired compound in the form of a white powder.

Yield: 82% Rf (dichloromethane/methanol 98:2): 0.54 IR: $\nu$CO thioester 1660 cm$^{-1}$; $\nu$CO amide 1651 cm$^{-1}$ MP: 83-85° C. NMR ($^1$H, CDCl$_3$): 0.89 (t, 9H, CH$_3$, J=6.6 Hz); 1.26 (multiplet, 66H, —CH$_2$—); 1.56-1.62 (multiplet, 6H, —CH$_2$—CH$_2$—S—CH$_2$—CO); 2.56 (t, 4H, —CH$_2$—CH$_2$—S—CH$_2$—CONH—, J=7.5 Hz); 2.61 (t, 2H, —CH$_2$—CH$_2$—S—CH$_2$—COS—, J=7 Hz); 3.26 (s, 4H, CH$_2$—S—CH$_2$—CONH—); 3.42 (s, 2H, CH$_2$—S—CH$_2$—COS—); 3.44-3.49 (m, 2H, —CONH—CH$_a$H$_b$—CH—CH$_a$H$_b$—NH—CO); 3.55-3.61 (m, 2H, —CONH—CH$_a$H$_b$—CH—CH$_a$H$_b$—NHCO—); 3.70-3.71 (m, 1H, BOCNH—CH$_2$—CH—CH$_2$—NHBOC); 7.58-7.62 (m, 2H, NHCO). MS (MALDI-TOF): M+1=917 (M+H$^+$); M+23=939 (M+Na$^+$)

Example 17

Preparation of 1-amino-2,3-di(tetradecylthioacetylthio)propane hydrochloride

Preparation of 1-(tert-butyloxycarbonylamino)propane-2,3-diol (example 17a)

1-aminopropane-2,3-diol (5 g, 55 mmol) was dissolved in methanol (200 ml) followed by dropwise addition of triethylamine (0.5 ml per mmol of amine) and di-tert-butyl dicarbonate [(BOC)2O] wherein BOC corresponds to tert-butyloxycarbonyl (17.97 g, 82 mmol). The reaction medium was heated at 40-50° C. for 20 min then stirred at room temperature for 1 hour. After evaporation of the solvent, the colorless oily residue was purified by chromatography on silica gel (eluent: dichloromethane/methanol 95:5) to give the desired compound in the form of a colorless oil which crystallized slowly.

Yield: 99% Rf (dichloromethane/methanol 9:1): 0.39 IR: $\nu$NH 3350 cm$^{-1}$; $\nu$CO ester 1746 cm$^{-1}$; $\nu$CO amide 1682 cm$^{-1}$ MP<15° C. NMR ($^1$H, CDCl$_3$): 1.44 (s, 9H, CH$_3$ (BOC)); 3.16-3.31 (m, 2H, BOCNH—CH$_2$—CH—CH$_2$—OH); 3.44 (multiplet, 2H, OH); 3.16-3.31 (m, 2H, BOCNH—CH$_2$—CH—CH$_2$—OH); 3.71-3.78 (m, 1H, BOCNH—CH$_2$—CH—CH$_2$—OH); 5.24 (m, 1H, —NHBOC). MS (MALDI-TOF): M+23=214 (M+Na$^+$)

Preparation of 1-(tert-butyloxycarbonylamino)-2,3-di(n-toluenesulfonyloxy)propane (example 17b)

This compound was synthesized according to the method described hereinabove (example 15a) from 1-(tert-butyloxycarbonylamino)-propane-2,3-diol (example 17a) and p-toluenesulfonyl chloride. The reaction produced a white powder.

Yield: 45% Rf (dichloromethane/methanol 98:2): 0.49 IR: $\nu$NH 3430 cm$^{-1}$; $\nu$CO ester and carbamate 1709 cm$^{-1}$ MP: 112-116° C. NMR ($^1$H, CDCl$_3$): 1.40 (s, 9H, CH$_3$ (BOC)); 2.46 (s, 6H, CH$_3$); 3.26-3.45 (m, 2H, BOCNH—CH$_2$—CH—CH$_2$—OTs); 4.04-4.14 (m, 2H, BOCNH—CH$_2$—CH—CH$_2$—OTs); 4.68 (m, 1H, BOCNH—CH$_2$—CH—CH$_2$—OTs); 4.71 (s, 1H, —NHBOC); 7.34 (d, 4H, aromatics, J=8.5 Hz); 7.69 (d, 2H, aromatics, J=8.1 Hz); 7.76 (d, 2H, aromatics, J=8.1 Hz). MS (MALDI-TOF): M+23=522 (M+Na$^+$); M+39=538 (M+K$^+$)

Preparation of 1-(tert-butyloxycarbonylamino)-2,3-di(acetylthio)propane (example 17c)

This compound was synthesized according to the method described hereinabove (example 15b) from 1-(tert-butyloxycarbonylamino)-2,3-di(p-toluenesulfonyloxy)-propane (example 17b) and potassium thioacetate. The reaction produced a white solid.

Yield: 59% Rf (dichloromethane/ethyl acetate 95:5): 0.55 IR: $\nu$NH 3430 cm$^{-1}$; $\nu$CO thioester 1718 cm$^{-1}$; $\nu$CO carbamate 1690 cm$^{-1}$ MP: 62-63° C. NMR ($^1$H, CDCl$_3$): 1.45 (s, 9H, CH$_3$ (BOC)); 2.35 (s, 3H, CH$_3$); 2.37 (s, 3H, CH$_3$); 3.12-3.38 (multiplet, 4H, BOCNH—CH$_2$—CH—CH$_2$—SCO—); 3.69-3.78 (m, 1H, BOCNH—CH$_2$—CH—CH$_2$—SCO—); 5.02 (s, 1H, —NHBOC). MS (MALDI-TOF): M+23=330 (M+Na$^+$)

Preparation of 1-(tert-butyloxycarbonylamino)-2,3-dimercantopropane (example 17d)

This compound was synthesized according to the method described hereinabove (example 15c) by saponification of 1-(tert-butyloxycarbonylamino)-2,3-di(acetylthio)-propane (example 17c). The reaction produced a white solid which was promptly used in the next reaction.

Yield: 95% Rf (dichloromethane/ethyl acetate 95:5): 0.45 IR: $\nu$NH 3368 cm$^{-1}$; $\nu$CO carbamate 1688 cm$^{-1}$ MP: 62-63° C. NMR ($^1$H, CDCl$_3$): 1.46 (s, 9H, CH$_3$ (BOC)); 3.04-3.11 (m, 1H, BOCNH—CH$_2$—CHSH—CH$_2$—SH); 3.26-3.35 (m, 2H, BOCNH—CH$_2$—CHSH—CH$_2$—SH); 3.43-3.52 (m, 2H, BOCNH—CH$_2$—CH—CH$_2$—SH); 4.91 (m, 2H, SH); 5.08 (s, 1H, —NHBOC).

Preparation of 1-(tert-butyloxycarbonylamino)-2,3-di(tetradecylthioacetylthio)pronane (example 17e)

This compound was synthesized according to the method described hereinabove (example 15d) from 1-(tert-butyloxycarbonylamino)-2,3-dimercaptopropane (example 17d) and tetradecylthioacetic acid (example 1). The reaction produced a white solid.

Yield: 50% Rf (dichloromethane): 0.38 IR: $\nu$NH 3421 cm$^{-1}$; $\nu$CO thioester 1721 cm$^{-1}$; $\nu$CO carbamate 1683 cm$^{-1}$ MP: 60-62° C. NMR ($^1$H, CDCl$_3$): 0.87 (t, 6H, CH$_3$, J=6.3 Hz); 1.26 (multiplet, 44H, —CH$_2$—); 1.45 (s, 9H, CH$_3$ (BOC)); 1.57-1.62 (m, 4H, —CH$_2$—CH$_2$—COS—); 2.60 (t, 4H, —CH$_2$—CH$_2$—S—CH$_2$—COS—, J=6.9 Hz); 3.17-3.29 (m, 2H, BOCNH—CH$_a$H$_b$—CH—CH$_a$H$_b$—NHBOC); 3.29-3.38 (m, 2H, BOCNH—CH$_a$H$_b$—CH—CH$_a$H$_b$—NHBOC); 3.41 (s, 2H, CH$_2$—S—CH$_2$—COS—); 3.43 (s, 2H, CH$_2$—S—CH$_2$—COS—); 3.76-3.80 (m, 1H, BOCNH—CH$_2$—CH—CH$_2$—NHBOC); 5.03 (s, 1H, —NHBOC). MS (MALDI-TOF): M+23=786 (M+Na$^+$)

Preparation of 1-amino-2,3-ditetradecylthioacetylthio)propane hydrochloride (example 17)

This compound was synthesized according to the method described hereinabove (example 15) from 1-(tert-butyloxycarbonylamino)-2,3-ditetradecylthioacetyl-thiopropane (example 17e). The reaction produced a white solid.

Yield: 43% Rf (dichloromethane): 0.19 IR: $\nu$NH.HCl 2700-3250 cm$^{-1}$; $\nu$CO thioester 1701 and 1676 cm$^{-1}$ MP: 117-128° C. NMR ($^1$H, CDCl$_3$): 0.86 (t, 6H, CH$_3$, J=6 Hz); 1.24 (multiplet, 44H, —CH$_2$—); 1.51 (m, 4H, —CH$_2$—CH$_2$—S—CH$_2$—COS—); 2.61 (m, 4H, —CH$_2$—CH$_2$—S—CH$_2$—COS—); 2.93-3.04 (m, 2H, —S—CH$_a$H$_b$—CH—CH$_a$H$_b$—NH$_2$.HCl); 3.11-3.20 (m, 2H, —S—CH$_a$H$_b$—CH—CH$_a$H$_b$—NH$_2$.HCl); 3.59-3.63 (multiplet, 4H, CH$_2$—S—CH$_2$—COS—); 3.72-3.84 (m, 1H, —S—CH$_2$—CH—CH$_2$—NH$_2$.HCl); 8.12 (m, 3H, NH$_2$.HCl).

Example 18

Preparation of 1-tetradecylthioacetylamino-2,3-di(tetradecylthioacetylthio)propane 1-amino-2,3-ditetradecylthioacetylthiopropane hydrochloride (example 17) (100 mg, 0.140 mmol) and tetradecylthioacetic acid (example 1) (62 mg, 0.210 mmol) were dissolved in dichloromethane (40 ml) at 0° C. followed by the addition of triethylamine (43 ml), dicyclohexylcarbodiimide (59 mg, 0.28 mmol) and hydroxybenzotriazole (29 mg, 0.210 mmol). The reaction mixture was stirred at 0° C. for 1 hour then brought to room temperature for 24 hours. It was then heated under gentle reflux for 48 hours, then dried. The residue obtained (310 mg) was purified by chromatography on silica gel (eluent: dichloromethane/cyclohexane 8:2) and produced the desired comopund as a white powder.

Yield: 96% Rf (dichloromethane): 0.20 IR: $\nu$NH amide 3306 cm$^{-1}$; $\nu$CO thioester 1674 cm$^{-1}$; $\nu$CO amide 1648 cm$^{-1}$ MP: 78-80° C. NMR ($^1$H, CDCl$_3$): 0.89 (t, 9H, CH$_3$, J=6.6 Hz); 1.26 (multiplet, 66H, —CH$_2$—); 1.58-1.62 (multiplet, 6H, —CH$_2$—CH$_2$—S—CH$_2$—COS—); 2.56 (t, 4H, —CH$_2$—CH$_2$—S—CH$_2$—COS—, J=7.5 Hz); 2.61 (t, 2H, —CH$_2$—CH$_2$—S—CH$_2$—CONH—, J=7 Hz); 3.26 (s, 4H, CH$_2$—S—CH$_2$—COS—); 3.42 (s, 2H, CH$_2$—S—CH$_2$—CONH—); 3.44-3.49 (m, 2H, —S—CH$_a$H$_b$—CH—CH$_a$H$_b$—NHCO—); 3.55-3.61 (m, 2H, —S—CH$_a$H$_b$—CH—CH$_a$H$_b$—NHCO—); 3.70-3.71 (m, 1H, —S—CH$_2$—CH—CH$_2$—NHCO—); 7.58-7.62 (m, 1H, NHCO). MS (MALDI-TOF): M+1=934 (M+H$^+$); M+23=956 (M+Na$^+$); M+39=972 (M+K$^+$)

Example 19

Preparation of 1-tetradecylthioacetylthio-2,3-di(tetradecylthioacetylamino)propane Preparation of 2,3-di(tetradecylthioacetylamino)-1-iodopropane (example 19a)

2,3-ditetradecylthioacetylaminopropan-1-ol (example 13) (0.200 g, 0.317 mmol) was dissolved in toluene (30 ml).

Imidazole (0.054 g, 0.792 mmol), triphenylphosphine (0.208 g, 0.792 mmol) and iodine (0.161 g, 0.634 mmol) were then added in that order and the reaction was heated at 75-80° C. with stirring. After 6 hours of reaction, the solvent was evaporated and the residual product was used without further purification. Rf (dichloromethane/methanol 98:2): 0.55

Preparation of 2,3-di(tetradecylthioacetylamino)-1-mercaptopronane (example 19b)

Sodium hydrogen sulfide (0.089 g, 1.59 mmol) was added to 2,3-ditetradecylthioacetylamino-1-iodopropane (example 19a) (0.235 g, 0.32 mmol) dissolved in acetone (80 ml). The reaction medium was heated at 70° C. for 16 hours. The solvent was evaporated and the residue taken up in water and extracted with chloroform. The aqueous phase was acidified to pH 6 with acetic acid, then extracted again with chloroform. The organic phases were dried on magnesium sulfate and filtered and the solvent was evaporated. The residue obtained was used without further purification.

Preparation of 1-tetradecylthioacetylthio-2,3-di(tetradecylthioacetylamino)propane (example 19)

2,3-ditetradecylthioacetylamino-1-mercaptopropane (example 19b) (0.205 g, 0.32 mmol) was dissolved in tetrahydrofuran (50 ml). Dicyclohexylcarbodiimide (98 mg, 0.47 mmol), dimethylaminopyridine (58 mg, 0.47 mmol) and tetradecylthioacetic acid (example 1) (137 mg, 0.47 mmol) were then added. The mixture was stirred at room temperature for 20 hours. The dicyclohexylurea precipitate was filtered, washed with tetrahydrofuran and the filtrate was evaporated. The residue obtained (1.14 g) was purified by chromatography on silica gel (eluent: dichloromethane) to give the desired compound in the form of an ochre powder.

Yield: 10% Rf (dichloromethane/ethyl acetate 98:2): 0.19 IR: $\nu$CO thioester 1711-1745 cm$^{-1}$; $\nu$CO amide 1651 cm$^{-1}$ MP: 48.8-49.8° C. NMR ($^1$H, CDCl$_3$): 0.89 (t, 9H, CH$_3$, J=6.3 Hz); 1.26 (multiplet, 66H, —CH$_2$); 1.58 (m, 6H, —CH$_2$—CH$_2$—S—CH$_2$—COS—); 2.46-55 (m, 4H, —CH$_2$—CH$_2$—S—CH$_2$—CONH); 2.65 (t, 2H, —CH$_2$—CH$_2$—S—CH$_2$—COS—, J=7.4 Hz); 3.24 (s, 2H, CH$_2$—S—CH$_2$—CONH—); 3.26 (s, 2H, CH$_2$—S—CH$_2$—CONH—); 3.66 (t, 2H, —COS—CH$_2$—CH—CH$_2$—NHCO); 3.79 (t, 2H, CH$_2$—S—CH$_2$—COS—, J=6.3 Hz); 4.31-4.41 (m, 2H, —COS—CH$_2$—CH—CH$_2$—NHCO); 5.00-5.05 (m, 1H, —COS—CH$_2$—CH—CH$_2$—NHCO); 7.33 (sl, 1H, NHCO); 9.27 (d, 1H, NHCO, J=8.6 Hz). MS (MALDI-TOF): M+1=917 (M+H$^+$); M+23=939 (M+Na$^+$); M+39=955 (M+K$^+$)

Example 20

Preparation of 3-tetradecylthioacetylamino-2-tetradecylthioacetylthiopropan-1-ol Preparation of 3-tetradecylthioacetylamino-1-triphenylmethyloxypropan-2-ol (example 20a)

Chlorotriphenylmethane (2.833 g, 10.16 mmol) was added to a solution of 3-tetradecylthioacetylaminopropane-1,2-diol (example 2) (3 g, 8.30 mmol) in pyridine (2.5 ml). The reaction mixture was stirred at 50° C. for 24 hours and the solvent was then vacuum evaporated. The residue was taken up in water and extracted with dichloromethane. The organic phase was washed with 1 N aqueous hydrochloric acid then with an aqueous solution saturated in sodium chloride. It was dried on magnesium sulfate, filtered and the solvent was evaporated. The residue obtained (6.36 g) was purified by chromatography on silica gel (eluent: dichloromethane/ethyl acetate 98:2) to give the desired compound in the form of a white powder.

Yield: 69% Rf (dichloromethane/ethyl acetate 8:2): 0.61 IR: $\nu$NH amide 3225 cm$^{-1}$; $\nu$CO amide 1654 cm$^{-1}$ MP: 62.6-65.4° C. NMR ($^1$H, CDCl$_3$): 0.89 (t, 3H, CH$_3$, J=6.7 Hz); 1.26 (multiplet, 22H, —CH$_2$); 1.50-1.57 (m, 2H, —CH$_2$—CH$_2$—S—CH$_2$—CONH—); 2.48 (t, 2H, —CH$_2$—CH$_2$—S—CH$_2$—CONH, J=7.2 Hz); 3.01 (m, 1H, OH); 3.17 (s, 2H, CH$_2$—S—CH$_2$—CONH—); 3.19 (m, 2H, —O—CH$_2$—CH—CH$_2$—NHCO or trityl-O—CH$_2$—CH—CH$_2$—NHCO); 3.27-3.36 (m, 1H, —O—CH$_2$—CH—CH$_2$—NHCO or trityl-O—CH$_2$—CH—CH$_2$—NHCO); 3.54-3.62 (m, 1H, —O—CH$_2$—CH—CH$_2$—NHCO or trityl-O—CH$_2$—CH—CH$_2$—NHCO); 3.93 (m, 1H, —O—CH$_2$—CH—CH$_2$—NHCO); 7.16 (t, 1H, NHCO, J=5.7 Hz); 7.23-7.35 (multiplet, 9H, aromatic H); 7.41-7.45 (multiplet, 6H, aromatic H). MS (MALDI-TOF): M+23=626 (M+Na$^+$).

Preparation of 2-iodo-3-tetradecylthioacetylamino-1-triphenylmethyloxypropane (example 20b)

3-tetradecylthioacetylamino-1-triphenylmethyloxypropan-2-ol (example 20a) (2 g, 3.31 mmol) was dissolved in toluene (100 ml). Imidazole (0.564 g, 8.28 mmol), triphenylphosphine (2.171 g, 8.28 mmol) and iodine (1.681 g, 6.62 mmol) were then added in that order. The reaction medium was stirred at room temperature for 20 hours. A saturated sodium bisulfite solution was added until complete blanching of the reaction medium. The phases were separated and the aqueous phase was extracted with toluene. The organic phases were combined, washed with saturated sodium chloride solution, dried on magnesium sulfate and filtered. The residue obtained after evaporation of the solvent (4.65 g) was purified by chromatography on silica gel (eluent: dichiromethane) to give the desired compound in the form of a yellow oil.

Yield: 21% Rf (dichloromethane/ethyl acetate 95:5): 0.58 IR: $\nu$CO amide 1668 cm$^{-1}$; $\nu$CH arom. monosubstituted 748 and 698 cm$^{-1}$ NMR ($^1$H, CDCl$_3$): 0.89 (t, 3H, CH$_3$, J=6.5 Hz); 1.26 (multiplet, 20H, —CH$_2$); 1.53-1.63 (m, 2H, —CH$_2$—CH$_2$—CH$_2$—S—CH$_2$—CONH—); 2.63 (m, 2H, —CH$_2$—CH$_2$—CH$_2$—S—CH$_2$—CONH); 3.13-3.30 (m, 2H, —CH$_2$—CH$_2$—S—CH$_2$—CONH); 3.34 (s, 2H, CH$_2$—S—CH$_2$—CONH—); 3.67-3.71 (m, 2H, —O—CH$_2$—CH—CH$_2$—NHCO or trityl-O—CH$_2$—CH—CH$_2$—NHCO); 3.88-3.94 (m, 2H, —O—CH$_2$—CH—CH$_2$—NHCO or trityl-O—CH$_2$—CH—CH$_2$—NHCO); 4.76 (m, 1H, —O—CH$_2$—CH—CH$_2$—NHCO); 7.25-7.36 (multiplet, 9H, aromatic H); 7.45-7.49 (multiplet, 6H, aromatic H). MS (MALDI-TOF): M-127=586 (M-1)

Preparation of 2-mercapto-3-tetradecylthioacetylamino-1-triphenylmethyloxypropane (example 20c)

Sodium hydrogen sulfate hydrate (38 mg, 0.68 mmol) was prepared as a suspension in ethanol (20 ml) followed by the addition of 2-iodo-3-tetradecylthioacetylamino-1-triphenylmethyloxypropane (example 20b) (200 mg, 0.28 mmol). The reaction medium was heated at 70° C. 238 mg of sodium hydrogen sulfate hydrate were added over several days. After 6.5 days, the solvent was evaporated and the residue taken up in dichloromethane and washed with water. The aqueous phase was re-extracted and the combined organic phases were washed with 0.5N hydrochloric acid then with saturated sodium chloride solution, then dried on magnesium sulfate. The salt was filtered and the solvent evaporated. The residue obtained was used without further purification.

Rf (dichloromethane/ethyl acetate 95:5): 0.33

Preparation of 3-tetradecylthioacetylamino-2-tetradecylthioacetylthio-1-triphenylmethyloxy-pronane (example 20d)

2-mercapto-3-tetradecylthioacetylamino-1-triphenylmethyloxypropane (example 20c) (174 mg, 0.28 mmol) was dissolved in tetrahydrofuran (20 ml). Dicyclohexylcarbodiimide (88 mg, 0.42 mmol), dimethylaminopyridine (51 mg, 0.42 mmol) and tetradecylthioacetic acid (121 mg, 0.42 mmol) were then added and the reaction medium was stirred at room temperature. After 20 hours of reaction, the solvent was evaporated and the residue obtained (450 mg) was purified by flash chromatography (eluent: dichloromethane/cyclohexane 3:7 to 5-5) to give the desired compound in the form of a white powder.

Yield: 76% Rf (dichloromethane): 0.39 IR: νCO thioester and amide 1745 to 1640 cm$^{-1}$ MP: 48.5-51.9° C. NMR ($^1$H, CDCl$_3$): 0.89 (t, 6H, CH$_3$, J=6.3 Hz); 1.26 (multiplet, 44H, —CH$_2$); 1.62 (m, 4H, —CH$_2$—CH$_2$—S—CH$_2$—CO—); 2.42 (t, 2H, —CH$_2$—CH$_2$—S—CH$_2$—CONH—, J=7.5 Hz); 2.68 (t, 2H, —CH$_2$—CH$_2$—S—CH$_2$—COS—, J=7.5 Hz); 3.14 (s, 2H, CH$_2$—S—CH$_2$—CONH—); 3.25 (s, 2H, CH$_2$—S—CH$_2$—COS—); 3.50-3.59 (m, 1H, —O—CH$_2$—CH—CH$_2$—NHCO or trityl-O—CH$_2$—CH—CH$_2$—NHCO); 3.66-3.72 (m, 1H, —O—CH$_2$—CH—CH$_2$—NHCO or trityl-O—CH$_2$—CH—CH$_2$—NHCO); 3.96 (m, 1H, —O—CH$_2$—CH—CH$_2$—NHCO or trityl-O—CH$_2$—CH—CH$_2$—NHCO); 3.54-3.62 (m, 1H, —O—CH$_2$—CH—CH$_2$—NHCO or trityl-O—CH$_2$—CH—CH$_2$—NHCO); 5.16 (m, 1H, —O—CH$_2$—CH—CH$_2$—NHCO); 7.04 (m, 1H, NHCO, J=5.7 Hz); 7.25-7.34 (multiplet, 9H, aromatic H); 7.42-7.45 (multiplet, 9H, aromatic H). MS (MALDI-TOF): M+23=889 (M+Na$^+$)

Preparation of 3-tetradecylthioacetylamino-2-tetradecylthioacetylthiopropan-1-ol (example 20)

3-tetradecylthioacetylamino-2-tetradecylthioacetylthio-1-triphenylmethyloxy-propane (example 20d) (187 mg, 0.21 mmol) was dissolved in ether saturated with gaseous hydrochloric acid (12 ml). The reaction medium was stirred at room temperature for 20 hours. The precipitate which formed was filtered and washed with diethyl ether to give the desired compound in the form of a white powder.

Yield: 52% Rf (dichloromethane/methanol 98:2): 0.48 IR: νCO thioester 1704 cm$^{-1}$; νCO amide 1646 cm$^{-1}$ MP: 88.4-94.1° C. NMR ($^1$H, CDCl$_3$): 0.89 (t, 6H, CH$_3$, J=6.4 Hz); 1.26-1.37 (multiplet, 44H, —CH$_2$); 1.55-1.61 (m, 4H, —CH$_2$—CH$_2$—S—CH$_2$—CO—); 2.55 (t, 2H, —CH$_2$—CH$_2$—S—CH$_2$—CONH—, J=7 Hz); 2.65 (t, 2H, —CH$_2$—CH$_2$—S—CH$_2$—COS—, J=7 Hz); 3.26 (s, 2H, CH$_2$—S—CH$_2$—CONH—); 3.27 (s, 2H, CH$_2$—S—CH$_2$—COS—); 3.36-3.38 (m, 1H, —O—CH$_2$—CH—CH$_2$—NHCO); 3.58-3.64 (m, 1H, —O—CH$_2$—CH—CH$_2$—NHCO); 4.02 (m, 1H, —O—CH$_2$—CH—CH$_2$—NHCO); 4.11-4.25 (m, 2H, HO—CH$_2$—CH—CH$_2$—NHCO); 7.34 (m, 1H, NHCO). MS (MALDI-TOF): M+23=670 (M+Na$^+$)

Example 21

Preparation of 3-tetradecylthioacetylamino-1-tetradecylthiacetyloxy-2-tetradecylthioacetylthiopropane 3-tetradecylthioacetylamino-2-tetradecylthioacetylthiopropan-1-ol (example 20) (64 mg, 0.10 mmol) was dissolved in tetrahydrofuran (7 ml). Dicyclohexylcarbodiimide (31 mg, 0.15 mmol), dimethylaminopyridine (18 mg, 0.15 mmol) and tetradecylthioacetic acid (example 1) (43 mg, 0.15 mmol) were then added. The mixture was stirred at room temperature for 20 hours. The dicyclohexylurea precipitate was filtered and the filtrate was evaporated. The residue obtained (140 mg) was purified by flash chromatography (eluent: dichloromethane) to give the desired compound in the form of a white powder.

Yield: 17% Rf (dichloromethane/ethyl acetate 98:2): 0.23 IR: νCO ester 1730 cm$^{-1}$; νCO thioester 1671 cm$^{-1}$; νCO amide 1645 cm$^{-1}$ MP: 59.0-63.4° C. NMR ($^1$H, CDCl$_3$): 0.89 (t, 9H, CH$_3$, J=6.5 Hz); 1.26-1.37 (multiplet, 66H, —CH$_2$); 1.58-1.63 (m, 6H, —CH$_2$—CH$_2$—S—CH$_2$—CO—); 2.53 (t, 2H, —CH$_2$—CH$_2$—S—CH$_2$—CONH—, J=7.6 Hz); 2.61-2.67 (m, 4H, —CH$_2$—CH$_2$—S—CH$_2$—COS— and —CH$_2$—CH$_2$—S—CH$_2$—COO); 3.23 (s, 4H, CH$_2$—S—CH$_2$—CONH— and CH$_2$—S—CH$_2$—COO—); 3.24 (s, 2H, CH$_2$—S—CH$_2$—COS—); 3.50-3.57 (m, 1H, —O—CH$_2$—CH—CH$_2$—NHCO); 3.63-3.72 (m, 1H, —O—CH$_2$—CH—CH$_2$—NHCO); 4.19-4.25 (m, 1H, —O—CH$_2$—CH—CH$_2$—OCO); 3.63-3.72 (m, 1H, —O—CH$_2$—CH—CH$_2$—OCO); 5.19 (m, 1H, —O—CH$_2$—CH—CH$_2$—NHCO); 7.20 (m, 1H, NHCO). MS (MALDI-TOF): M+23=940 (M+Na$^+$)

Example 22

Preparation of 1-amino-2-tetradecylthioacetyloxy-3-tetradecylthioacetylthiopropane hydrochloride

Preparation of 1-tert-butyloxycarbonylamino-3-iodopronan-2-ol (example 22a)

1-[(tert-butyloxycarbonyl)amino]propane-2,3-diol (example 17a) (3.88 g, 20 mmol) was dissolved in toluene (250 ml). Imidazole (1.73 g, 25 mmol), triphenylphosphine (6.65 g, 25 mmol) and iodine (5.15 g, 20 mmol) were then added in that order. The reaction medium was stirred at room temperature for 17 hours and 0.5 equivalents of imidazole, triphenylphosphine and iodine were added. After 21 hours of reaction, a saturated sodium sulfite solution was added until complete blanching of the reaction medium. The phases were allowed to settle and the aqueous phase was extracted twice with toluene. The combined organic phases were washed with saturated sodium chloride solution, dried on magnesium sulfate, filtered and the solvent evaporated. The residue obtained (11.02 g) was purified by chromatography on silica gel (eluent: dichloromethane/ethyl acetate 95:5) to give the desired compound as a yellow paste which was promptly used in the next reaction.

Yield: 41% Rf (dichloromethane/methanol 98:2): 0.24 IR: νNH amide 3387 cm$^{-1}$; νCO carbamate 1678 cm$^{-1}$

Preparation of 3-acetylthio-1-tert-butyloxycarbonylaminopropan-2-ol (example 22b)

1-(tert-butyloxycarbonylamino)-3-iodopropan-2-ol (example 22a) (2 g, 6.64 mmol) and potassium thioacetate (0.948 g, 8.30 mmol) were dissolved in acetone (30 ml) and the medium was refluxed for 16 hours. The solvent was vacuum evaporated and the residue was taken up in diethyl ether, then filtered on Celite®. The filtrate was evaporated. The residue obtained (1.69 g) was purified by chromatography on silica gel (eluent: dichloromethane/ethyl acetate 98:2) then repurified by flash chromatography (eluent: dichloromethane) to give the desired compound in the form of a yellow oil.

Yield: 27% Rf (dichloromethane/ethyl acetate 95:5): 0.31 IR: νNH amide 3367 cm$^{-1}$; νCO thioester 1744 cm$^{-1}$; νCO carbamate 1697 cm$^{-1}$ NMR ($^1$H, CDCl$_3$): 1.26 (m, 9H, CH$_3$ (boc)); 2.37 (s, 3H, COCH$_3$); 3.04 (m, 1H, —NH—CH$_2$—CH—CH$_2$—S— or —NHCH$_2$—CH—CH$_2$—S—); 3.24 (m, 1H, —NH—CH$_2$—CH—CH$_2$—S-ou —NHCH$_2$—CH—CH$_2$—S—); 3.30-3.41 (m, 2H, —NH—CH$_2$—CH—CH$_2$—S— or —NHCH$_2$—CH—CH$_2$—S—); 4.86 (sl, 1H, OH); 4.96 (m, 1H, —NH—CH$_2$—CH—CH$_2$—S—).

Preparation of 1-tert-butyloxycarbonylamino-3-mercaptopronan-2-ol (example 22c)

3-acetylthio-1-tert-butyloxycarbonylaminopropan-2-ol (example 22b) (0.307 g, 1.23 mmol) diluted in a minimum of methanol (7 ml) was added to a 20% potassium carbonate solution (3.49 ml, 12.31 mmol) in methanol, deoxygenated under a stream of nitrogen. The medium was stirred at room temperature under a stream of nitrogen for 20 hours, then acidified to pH 6 with acetic acid and concentrated to dryness. The residue obtained was taken up in water and extracted with dichloromethane. The organic phase was dried on magnesium sulfate, filtered and concentrated. The oily residue obtained was used immediately in the next reaction without further purification.

Yield: 78% Rf (dichloromethane/ethyl acetate): 0.07

Preparation of 1-tert-butyloxycarbonylamino-2-tetradecylthioacetyloxy-3-tetradecylthioacetylthiopronane (example 22d)

1-(tert-butyloxycarbonylamino)-3-mercaptopropan-2-ol (example 22c) (0.200 g, 96 mmol) was dissolved in dichloromethane (50 ml). Dicyclohexylcarbodiimide (0.398 g, 1.93 mmol), dimethylaminopyridine (0.236 g, 1.93 mmol) and tetradecylthioacetic acid (example 1) (0.557 g, 1.93 mmol) were then added. The mixture was stirred at room temperature for 20 hours. The dicyclohexylurea precipitate was filtered, washed with dichloromethane and the filtrate was evaporated. The residue obtained (1,2 g) was purified by chromatography on silica gel (eluent: dichloromethane) to give the desired compound in the form of a white paste.

Yield: 47% Rf (dichloromethane): 0.26 IR: νNH amide 3314 cm$^{-1}$; νCO ester, amide and thioester 1682 to 1744 cm$^{-1}$ NMR ($^1$H, CDCl$_3$): 0.89 (t, 6H, CH$_3$, J=6.5 Hz); 1.27 (multiplet, 40H, CH$_2$); 1.45 (multiplet, 9H, CH$_3$ (BOC)); 1.56-1.63 (m, 4H, —CH$_2$—CH$_2$—CH$_2$—S—CH$_2$—CO—); 2.65 (m, 4H, —CH$_2$—CH$_2$—S—CH$_2$—CO—); 2.92 (s, 4H, —CH$_2$—S—CH$_2$—CO—); 2.96 (m, 4H, —CH$_2$—S—CH$_2$—CO—); 3.24-3.40 (m, 2H, —NH—CH$_2$—CH—CH$_2$—S— or —NHCH$_2$—CH—CH$_2$—S); 3.44-3.51 (m, 2H, —NH—CH$_2$—CH—CH$_2$—S— or —NHCH$_2$—CH—CH$_2$—S—); 4.91 (m, 1H, —NH—CH$_2$—CH—CH$_2$—S—); 5.19 (m, 1H, NHCO). MS (MALDI-TOF): M+23=770 (M+Na$^+$)

Preparation of 1-amino-2-tetradecylthioacetyloxy-3-tetradecylthioacetylthio propane hydrochloride (example 22)

1-(tert-butoxycarbonylamino)-2-tetradecylthioacetyloxy-3-tetradecylthioacetyl-thiopropane (example 22d) (300 mg, 0.40 mmol) was dissolved in diethyl ether saturated with gaseous hydrochloric acid (70 ml) and the reaction medium was stirred at room temperature for 72 hours. The precipitate which formed was filtered, washed with diethyl ether and dried to give the desired compound in the form of a white powder.

Yield: 42% IR: νCO ester 1733 cm$^{-1}$; νCO thioester 1692 cm$^{-1}$ MP: 82° C. (decomposition) NMR ($^1$H, CDCl$_3$): 0.86 (t, 6H, CH$_3$, J=6.6 Hz); 1.24 (multiplet, 44H, —CH$_2$); 1.52 (m, 4H, —CH$_2$—CH$_2$—S—CH$_2$—CO—); 2.52-2.62 (m, 4H, —CH$_2$—CH$_2$—S—CH$_2$—CO—); 3.07-3.15 (multiplet, 4H, —S—CH$_2$—CH—CH$_2$—NH$_2$); 3.40 (s, 2H, CH$_2$—S—CH$_2$—COO—); 3.61 (s, 2H, CH$_2$—S—CH$_2$—COS—); 5.12 (m, 1H, —S—CH$_2$—CH—CH$_2$—NH$_2$); 8.01 (m, 3H, —NH$_2$.HCl)

Example 23

Preparation of 1-tetradecylthioacetylamino-2-tetradecylthiacetyloxy-3-tetradecylthioacetylthiopropane 3-amino-2-tetradecylthioacetyloxy-1-tetradecylthioacetyl-thiopropane hydrochloride (example 22) (100 mg, 0.15 mmol) and tetradecylthioacetic acid (example 1) (63 mg, 0.22 mmol) were dissolved in dichloromethane (30 ml) at 0° C. followed by the addition of triethylamine (0.044 ml), dicyclohexylcarbodiimide (60 mg, 0.29 mmol) and hydroxybenzotriazole (30 mg, 0.22 mmol). The reaction medium was stirred at 0° C. for 1 hour then brought to room temperature for 48 hours. The dicyclohexylurea precipitate was filtered, washed with dichloromethane and the filtrate was evaporated. The residue obtained (263 mg) was purified by flash chromatography (eluent: dichloromethane/ethyl acetate 98:2) to give the desired compound in the form of a white powder.

Yield: 98% Rf (dichloromethane/ethyl acetate 95:5): 0.38 IR: νNH amide 3340 cm$^{-1}$; νCO ester 1727 cm$^{-1}$; νCO amide and thioester 1655 and 1669 cm$^{-1}$ MP: 63.9-67.1° C. NMR ($^1$H, CDCl$_3$): 0.89 (t, 9H, CH$_3$, J=6.2 Hz); 1.26 (multiplet, 66H, —CH$_2$); 1.54-1.66 (m, 6H, —CH$_2$—CH$_2$—S—CH$_2$—CO—); 2.52-2.67 (m, 6H, —CH$_2$—CH$_2$—S—CH$_2$—CO—); 3.08 (m, 1H, —S—CH$_2$—CH—CH$_2$—NHCO or —S—CH$_2$—CH—CH$_2$—NHCO); 3.21 (s, 2H, CH$_2$—S—CH$_2$—CONH—); 3.23 (s, 2H, CH$_2$—S—CH$_2$—COO—); 3.27 (m, 1H, —S—CH$_2$—CH—CH$_2$—NHCO or —S—CH$_2$—CH—CH$_2$—NHCO); 3.43 (s, 2H, CH$_2$—S—CH$_2$—COS—); 3.50 (m, 1H, —S—CH$_2$—CH—CH$_2$—NHCO or —S—CH$_2$—CH—CH$_2$—NHCO); 3.62 (m, 1H, —S—CH$_2$—CH—CH$_2$—NHCO or —S—CH$_2$—CH—CH$_2$—NHCO); 5.06 (m, 1H, —COS—CH$_2$—CH—CH$_2$—NHCO); 7.24 (t, 1H, —NHCO, J=6.7 Hz) MS (MALDI-TOF): M+1=918 (M+H$^+$); M+23=940 (M+Na$^+$)

Example 24

Method of Preparation of the Compounds Represented by Formula (I) According to the Invention To perform the in vitro experiments described in the following examples, the inventive compounds were prepared in the form of an emulsion as described below.

An emulsion comprising an inventive compound and phosphatidylcholine (PC) was prepared as described by Spooner et al. (Spooner, Clark et al. 1988). The inventive compound was mixed with PC in a 4:1 (m/m) ratio in chloroform, the mixture was dried under nitrogen, then vacuum evaporated overnight; the resulting powder was taken up in 0.16 M KCl containing 0.01 M EDTA and the lipid particles were then dispersed by ultrasound for 30 minutes at 37° C. The liposomes so formed were then separated by ultracentrifugation (XL 80 ultracentrifuge, Beckman Coulter, Villepinte, France) at 25,000 rpm for 45 minutes to recover liposomes having a size greater than 100 nm and close to that of chylomicrons. Liposomes composed only of PC were prepared concurrently to use as negative control.

The composition of the liposomes in the inventive compound was estimated by using the enzyme calorimetric triglyceride assay kit. The assay was carried out against a standard curve, prepared with the lipid calibrator CFAS, Ref. 759350 (Boehringer Mannheim GmbH, Germany). The standard curve covered concentrations ranging from 16 to 500 μg/ml. 100 μl of each sample dilution or calibration standard were deposited per well on a titration plate (96 wells). 200 μl of triglyceride reagents, ref. 701912 (Boehringer Mannheim GmbH, Germany) were then added to each well, and the entire plate was incubated at 37° C. for 30 minutes. Optical densities (OD) were read on a spectrophotometer at 492 nm. Triglyceride concentrations in each sample were calculated from the standard curve plotted as a linear function y=ax+b, where y represents OD and x represents triglyceride concentrations.

Liposomes containing the inventive compounds, prepared in this manner, were used for in vitro experiments described in examples 26, 27 and 28.

Example 25

Evaluation of the Antioxidant Properties of the Inventive Compounds

A Protection against LDL oxidation induced by copper:

Oxidation of LDL is an important modification which plays a major role in the onset and development of atherosclerosis (Jurgens, Hoff et al. 1987). The following protocol allows demonstration of the antioxidant properties of compounds. Unless otherwise indicated, all reagents were from Sigma (St Quentin, France).

LDL were prepared as described in Lebeau et al. (Lebeau, Furman et al. 2000). The solutions of the test compounds were prepared at $10^{-2}$ M in ethanol and diluted in PBS so that the final concentration ranged from 0.1 to 100 μM with a total ethanol concentration of 1% (VN).

Before oxidation, EDTA was removed from the LDL preparation by dialysis. The oxidation reaction was then carried out at 30° C. by adding 100 μl of 16.6 μM $CuSO_4$ to 800 μl of LDL (125 μg protein/ml) and 100 μl of a test compound solution. The formation of dienes, the species to be followed, was measured by the optical density at 234 nm in the samples treated with the compounds in the presence or absence of copper. Optical density at 234 nm was measured every 10 minutes for 8 hours on a thermostated spectrophotometer (Kontron Uvikon 930). The analyses were carried out in triplicate. A compound was considered to have antioxidant activity when it shifted the lag phase latency relative to the control sample. The inventors demonstrate that the inventive compounds delayed LDL oxidation (induced by copper), indicating that the inventive compounds possess intrinsic antioxidant activity. FIG. 2 presents an example of the results obtained with the inventive compounds.

FIG. 2a shows that the inventive compounds shifted the lag phase latency by more than 13% for compound Ex 2 up to 34.3% for compound Ex 4. The inventive compounds did not appear to modify the oxidation rate (FIG. 2b) or the amount of dienes formed (FIG. 2c).

Figure 1:
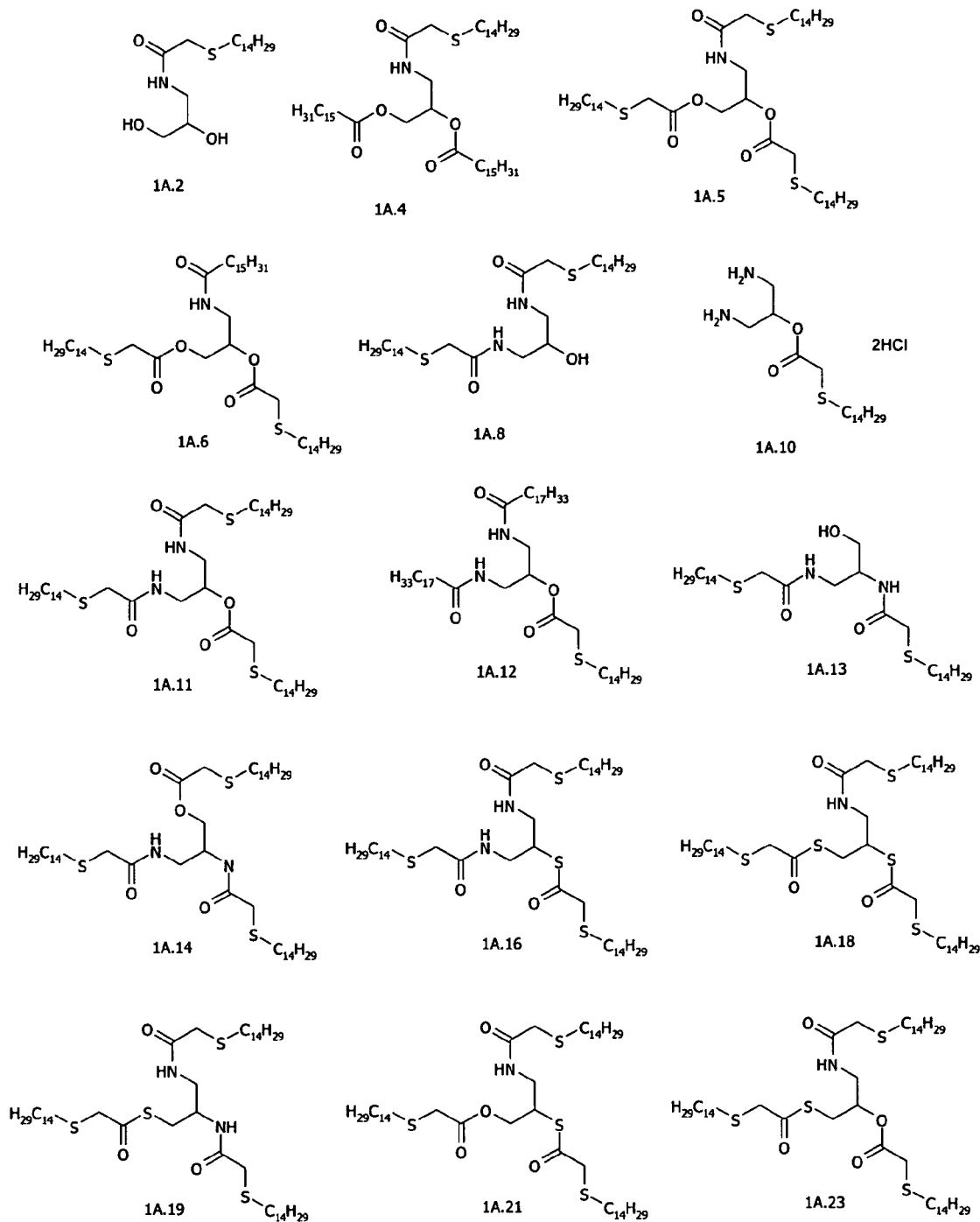
Figure 2:
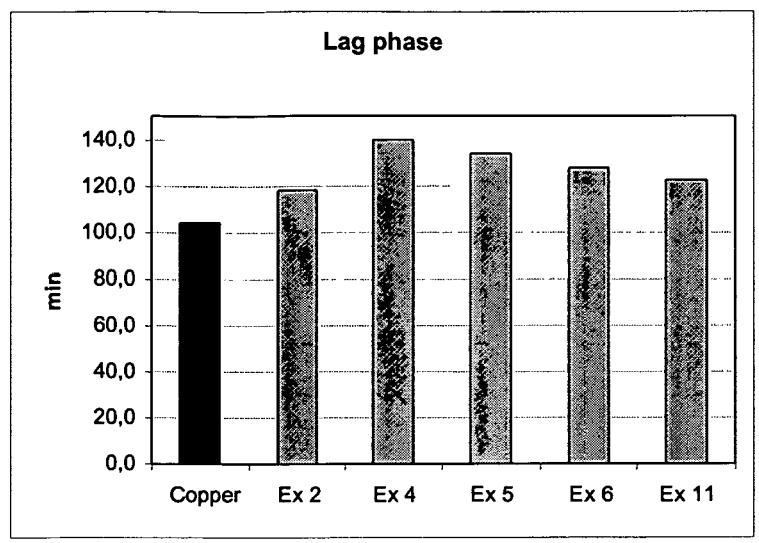
FIG. 2 shows that inventive compounds Ex 2, 4, 5, 6 et 11, exhibit intrinsic antioxidant properties.
Figure 2:
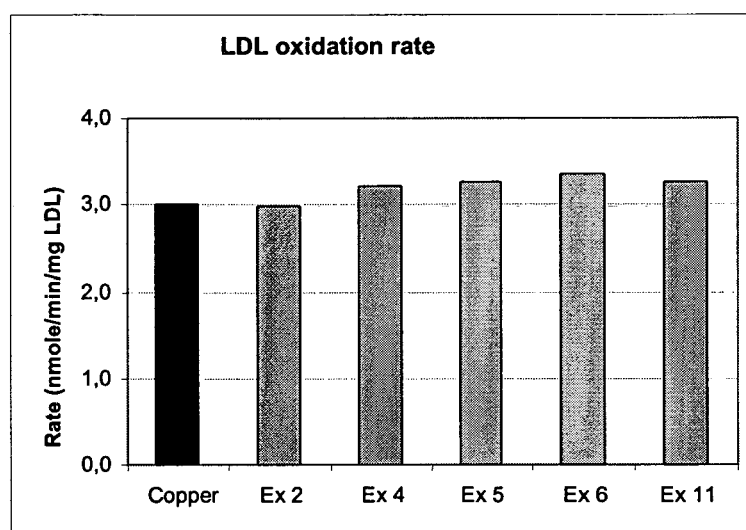
Figure 2:
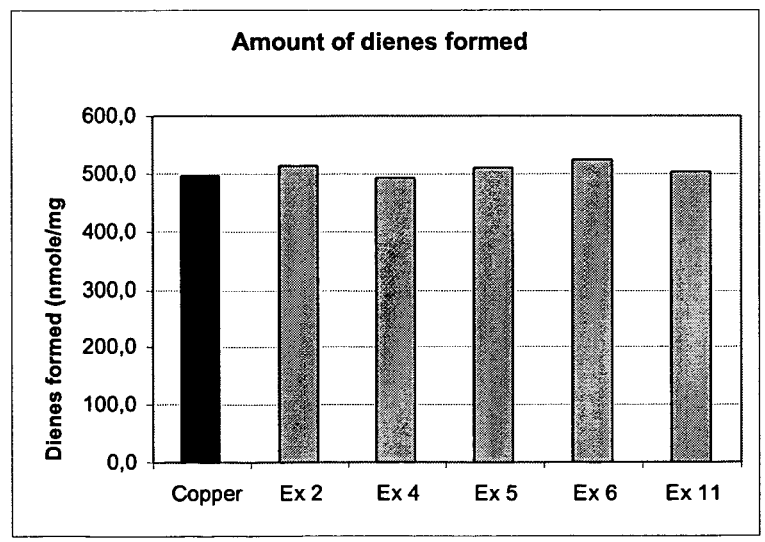

B—Evaluation of the protection conferred by the inventive compounds against lipid peroxidation:

The inventive compounds which were tested are the compounds whose preparation is described in examples 2 to 23.

LDL oxidation was measured by the TBARS method (Thiobarbituric Acid Reactive Substrates).

According to the same principle as that described hereinabove, LDL were oxidized in the presence of $CuSO_4$ and lipid peroxidation was evaluated as follows:

TBARS were measured by a spectrophotometric method, lipid hydroperoxidation was measured by using lipid peroxide-dependent oxidation of iodide to iodine.

The results are expressed as nmol of malondialdehyde (MDA) or as nmol hydroperoxide/mg protein.

The results obtained hereinabove by measuring the inhibition of conjugated diene formation, were confirmed by the experiments measuring LDL lipid peroxidation. Thus, the inventive compounds also afforded efficient protection of LDL against lipid peroxidation induced by copper (an oxidizing agent).

Example 26

Measurement of the Antioxidant Properties of the Inventive Compounds on Cell Cultures A—Culture Protocol:

Neuronal, neuroblastoma (human) and PC12 cells (rat) were the cell lines used for this type of study. PC12 cells were prepared from a rat pheochromocytoma and have been characterized by Greene and Tischler (Greene and Tischler, 1976). These cells are commonly used in studies of neuron differentiation, signal transduction and neuronal death. PC12 cells were grown as previously described (Farinelli, Park et al. 1996) in complete RPMI medium (Invitrogen) supplemented with 10% horse serum and 5% fetal calf serum.

Primary cultures of endothelial and smooth muscle cells were also used. Cells were obtained from Promocell (Promocell GmBH, Heidelberg) and cultured according to the supplier's instructions.

The cells were treated with different doses of the compounds ranging from 5 to 100 μM for 24 hours. The cells were then recovered and the increase in expression of the target genes was evaluated by quantitative PCR.

B—mRNA Measurement:

mRNA was extracted from the cultured cells treated or not with the inventive compounds. Extraction was carried out with the reagents of the Absolutely RNA RT-PCR miniprep kit (Stratagene, France) as directed by the supplier. mRNA was then assayed by spectrometry and quantified by quantitative RT-PCR with a Light Cycler Fast Start DNA Master Sybr Green I kit (Roche) on a Light Cycler System (Roche, France). Primer pairs specific for the genes encoding the antioxidant enzymes superoxide dismutase (SOD), catalase and glutathione peroxidase (GPx) were used as probes. Primer pairs specific for the □-actin and cyclophilin genes were used as control probes.

An increase in mRNA expression of the antioxidant enzyme genes, measured by quantitative RT-PCR, was demonstrated in the different cell types used, when the cells were treated with the inventive compounds.

C—Control of Oxidative Stress:

Measurement of Oxidizing Species in the Cultured Cells:

The antioxidant properties of the compounds were also evaluated by means of a fluorescent tag the oxidation of which is followed by appearance of a fluorescence signal. The reduction in the intensity of the emitted fluorescence signal was determined in cells treated with the compounds in the following manner: PC12 cells cultured as described earlier (black 96-well plates, transparent bottom, Falcon) were incubated with increasing doses of $H_2O_2$ (0.25 mM-1 mM) in serum-free medium for 2 and 24 hours. After incubation, the medium was removed and the cells were incubated with 10 μM dichlorodihydrofluorescein diacetate solution (DCFDA, Molecular Probes, Eugene, USA) in PBS for 30 min at 37° C. in a 5% $CO_2$ atmosphere. The cells were then rinsed with PBS. The fluorescence emitted by the oxidation tag was measured on a fluorimeter (Tecan Ultra 384) at an excitation wavelength of 495 nm and an emission wavelength of 535 nm. The results are expressed as the percentage of protection relative to the oxidized control. Fluorescence intensity was lower in the cells incubated with the inventive compounds than in untreated cells. These findings indicate that the inventive compounds promote inhibition of the production of oxidative species in cells subjected to oxidative stress. The previously described antioxidant properties are also effective at inducing antiradical protection in cultured cells.

D—Measurement of Lipid Peroxidation:

The different cell lines (cell models noted hereinabove) and the primary cell cultures were treated as described earlier. The cell supernatant was recovered after treatment and the cells were lysed and recovered for determination of protein concentration. Lipid peroxidation was detected as follows: lipid peroxidation was measured by using thiobarbituric acid (TBA) which reacts with lipid peroxidation of aldehydes such as malondialdehyde (MDA). After treatment, the cell supernatant was collected (900 μl) and 90 μl of butylated hydroxytoluene were added (Morliere, Moysan et al. 1991). One milliliter of 0.375% TBA solution in 0.25 M hydrochloric acid containing 15% trichloroacetic acid was also added to the reaction medium. The mixture was heated at 80° C. for 15 min, cooled on ice and the organic phase was extracted with butanol. The organic phase was analyzed by spectrofluorimetry ($\lambda exc$=515 nm and $\lambda em$=550 nm) on a Shimazu 1501 spectrofluorimeter (Shimadzu Corporation, Kyoto, Japan). TBARS are expressed as MDA equivalents using tetra-ethoxypropane as standard. The results were normalized for protein concentration.

The decrease in lipid peroxidation observed in the cells treated with the inventive compounds confirms the previous results.

The inventive compounds advantageously exhibit intrinsic antioxidant properties allowing to slow and/or inhibit the effects of an oxidative stress. The inventors also show that the inventive compounds are capable of inducing the expression of genes encoding antioxidant enzymes. These particular features of the inventive compounds allow cells to more effectively fight against oxidative stress and therefore be protected against free radical-induced damage.

Example 27

Evaluation of PPAR Activation In Vitro by the Inventive Compounds

Nuclear receptors of the PPAR subfamily which are activated by two major pharmaceutical classes—fibrates and glitazones, widely used in the clinic for the treatment of dyslipidemias and diabetes—play an important role in lipid and glucose homeostasis. The following experimental data show that the inventive compounds activate PPARα in vitro.

PPAR activation was tested in vitro in RK13 fibroblast cell lines or in a hematocyte line HepG2 by measuring the transcriptional activity of chimeras composed of the DNA binding domain of the yeast gal4 transcription factor and the ligand binding domain of the different PPARs. The example below is given for HepG2 cells.

A—Culture Protocols:

HepG2 cells were from ECACC (Porton Down, UK) and were grown in DMEM medium supplemented with 10% (VN) fetal calf serum, 100 U/ml penicillin (Gibco, Paisley, UK) and 2 mM L-glutamine (Gibco, Paisley, UK). The culture medium was changed every two days. Cells were kept at 37° C. in a humidified 95% air/5% $CO_2$ atmosphere.

B—Description of Plasmids used for Transfection:

The plasmids pG5TkpGL3, pRL-CMV, pGal4-hPPAR□, pGal4-hPPAR□ and pGal4-f have been described by Raspe et al. (Raspe, Madsen et al. 1999). The pGal4-mPPARα and pGal4-hPPARβ constructs were obtained by cloning PCR-amplified DNA fragments corresponding to the DEF domains of the mouse PPARα and human PPARα nuclear receptors, respectively, into the pGal4-f vector.

C—Transfection

HepG2 cells were seeded in 24-well culture dishes at $5 \times 10^4$ cells/well and transfected for 2 hours with the reporter plasmid pG5TkpGL3 (50 ng/well), the expression vectors pGal4-f, pGal4-mPPARα, pGal4-hPPARα, pGal4-hPPARγ, pGal4-hPPARβ (100 ng/well) and the transfection efficiency control vector pRL-CMV (1 ng/well) according to the previously described protocol (Raspe, Madsen et al. 1999), then incubated for 36 hours with the test compounds. At the end of the experiment, the cells were lysed (Gibco, Paisley, UK) and luciferase activity was determined with a Dual-Luciferase™ Reporter Assay System kit (Promega, Madison, Wis., USA) according to the supplier's instructions. The protein content of the cell extracts was then measured with the Bio-Rad Protein Assay kit (Bio-Rad, Munich, Germany) as directed by the supplier.

Figure 3:
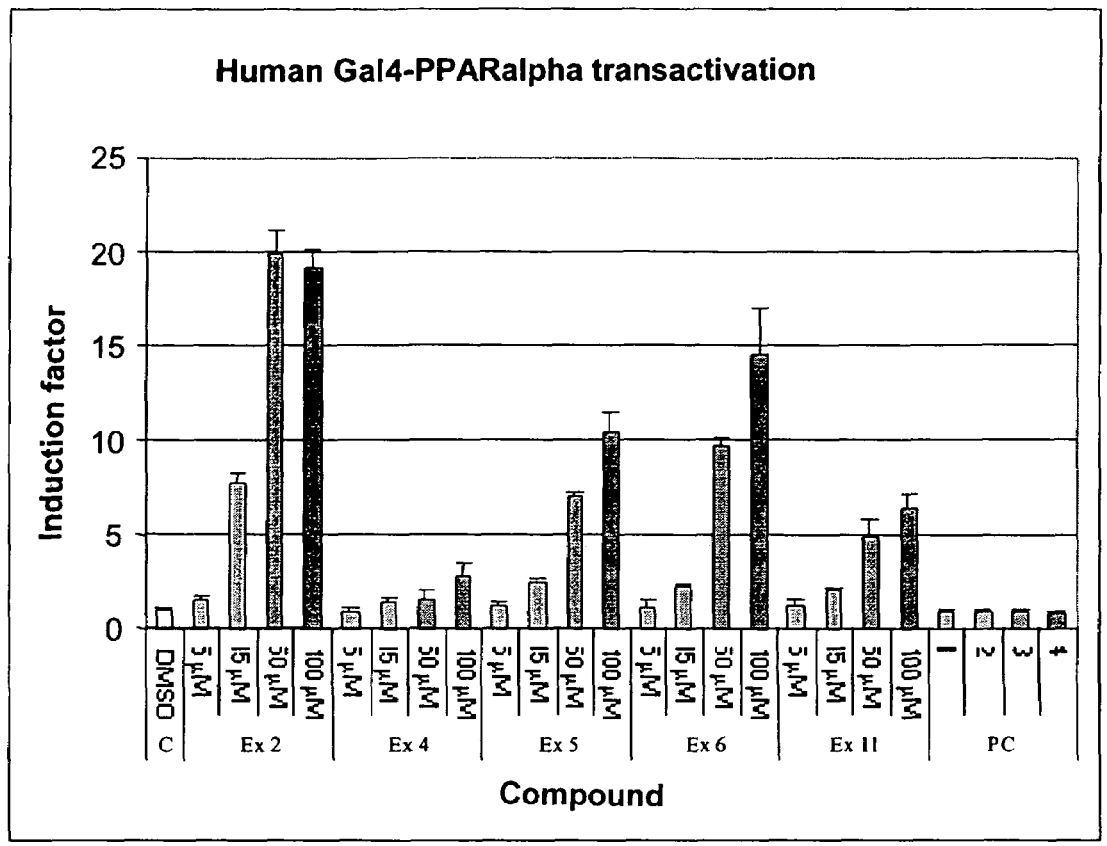

The inventors demonstrate an increase in luciferase activity in cells treated with the inventive compounds and transfected with the pGal4-hPPARα plasmid. Said induction of luciferase activity indicates that the inventive compounds are activators of PPARα. FIG. 3 gives an example of the results obtained with the inventive compounds.

FIG. 3: HepG2 cells transfected with Gal4/PPARα plasmids were incubated with different concentrations (5, 15, 50 and 100 μM) of the inventive comopunds (Ex 2, Ex 4, Ex 5, Ex 6, Ex 11) for 24 h and with different concentrations of the vehicle (PC) noted 1, 2, 3, 4 as controls for the 5, 15, 50 and 100 μM concentrations of the inventive compounds (according to the 4:1 (m/m) ratio described in example 24 (Method of preparation of compounds represented by formula (I) according to the invention)). The results are expressed as the induction factor (luminescent signal of treated cells divided by luminescent signal of untreated cells) after the different treatments. The higher the induction factor the more potent the PPARα agonist activity. The results show that inventive compound Ex 2 produced a maximum 19.8-fold induction of the luminescent signal at 50 µM, 19.2 at 100 µM, 7.7 at 15 µM and 1.5 at 5 µM. Inventive compound Ex 5 also showed a dose-dependent increase in the induction factor of 10.5 at 100 µM, 7 at 50 µM, 2.5 at 15 µM and 1,2 at 5 µM. Inventive compound Ex 6 also induced an increase in the luminescent signal, revealing an activity on the PPARα nuclear receptor. The induction factors for inventive compound Ex 6 were 14.5 at 100 µM, 9.6 at 50 µM, 2.2 at 15 µM and 1.1 at 5 µM. In contrast, when the cells were incubated with the vehicle (PC liposome), no significant induction was observed.

These results demonstrate that the inventive compounds tested exhibit significant PPARα ligand activity and therefore enable the transcriptional activation thereof.

Example 28

Evaluation of the Anti-inflammatory Properties of the Inventive Compounds

An inflammatory response is observed in many neurological disorders, such as cerebral ischemias. Inflammation is also an important factor in neurodegeneration. In stroke, one of the first reactions of glial cells is to release cytokines and free radicals. This release of cytokines and free radicals results in an inflammatory response in the brain which can lead to neuronal death (Rothwell 1997).

Cell lines and primary cells were cultured as described hereinabove.

Lipopolysaccharide (LPS) bacterial endotoxin (*Escherichia coli* 0111:B4) (Sigma, France) was reconstituted in distilled water and stored at 4° C. Cells were treated with LPS 1 µg/ml for 24 hours. To avoid interference from other factors, the culture medium was completely changed.

TNF-α is an important factor in the inflammatory response to stress (oxidative stress for example). To evaluate TNF-α secretion in response to stimulation by increasing doses of LPS, the culture medium of stimulated cells was removed and TNF-α was assayed with an ELISA-TNF-α kit (Immunotech, France). Samples were diluted 50-fold so as to be in the range of the standard curve (Chang, Hudson et al. 2000).

The anti-inflammatory property of the compounds was characterized as follows: the cell culture medium was completely changed and the cells were incubated with the test compounds for 2 hours, after which LPS was added to the culture medium at 1 µg/ml final concentration. After a 24-hour incubation, the cell supernatant was recovered and stored at −80° C. when not treated directly. Cells were lysed and protein was quantified with the Bio-Rad Protein Assay kit (Bio-Rad, Munich, Germany) according to the supplier's instructions.

The measurement of the decrease in TNF-α secretion induced by treatment with the test compounds is expressed as pg/ml/µg protein and as the percentage relative to the control. These results show that the inventive compounds have anti-inflammatory properties.

Example 29

Evaluation of the Neuroprotective Effects of the Inventive Compounds in a Cerebral Ischemia-reperfusion Model A—Prophylactic Model:

1—Treatment of Animals 1.1 Animals and Administration of the Compounds

Wistar rats weighing 200 to 350 g were used for this experiment.

Animals were maintained on a 12 hour light-dark cycle at a temperature of 20° C.±3° C. Water and food were available ad libitum. Food intake and weight gain were recorded.

Animals were treated by gavage with the inventive compounds (600 mg/kg/day) in suspension in the vehicle (0.5% carboxycellulose (CMC) and 0.1% Tween) or with the vehicle alone, for 14 days before ischemia induction by occlusion of the middle cerebral artery.

The carboxymethylcellulose used is a sodium salt of intermediate viscosity carboxymethylcellulose (Ref. C4888, Sigma-Aldrich, France). Tween used is Polyoxyethylenesorbitan Monooleate (Tween 80, Ref. P8074, Sigma-Aldrich, France).

1,2 Ischemia Induction-reperfusion by Intraluminal Occlusion of the Middle Cerebral Artery:

Animals were anesthetized by intraperitoneal injection of 300 mg/kg chloral hydrate. A rectal probe was inserted and body temperature was maintained at 37° C.±0.5° C. Blood pressure was monitored throughout the experiment. Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2—Measurement of Brain Infarct Volume:

Twenty-four hours after reperfusion, animals previously treated or not with the inventive compounds were euthanized by pentobarbital overdose.

Brains were rapidly frozen and sliced. Sections were stained with cresyl violet. Unstained zones of the brain sections were considered to be damaged by the infarct. Areas (of the infarct and the two hemispheres) were measured and the volume of the infarct and the two hemispheres was calculated and the corrected infarct volume was determined by the following formula: (corrected infarct volume=infarct volume−(volume of right hemisphere−volume of left hemisphere)) to compensate for cerebral oedema.

Analysis of the brain sections from animals treated with the inventive compounds revealed a marked decrease in infarct volume as compared with untreated animals. When the inventive compounds were administered to the animals before the ischemia (prophylactic effect), they were capable of inducing neuroprotection.

3—Measurement of Antioxidant Enzyme Activity:

The rat brains were frozen, crushed and reduced to powder, then resuspended in saline solution. The different enzyme activities were then measured as described by the following authors: superoxide dismutase (Flohe and Otting 1984); glutathione peroxidase (Paglia and Valentine 1967); glutathione reductase (Spooner, Delides et al. 1981); glutathione-S-transferase (Habig and Jakoby 1981); catalase (Aebi 1984).

Said different enzyme activities were increased in brain preparations from animals treated with the inventive compounds.

B—Curative or Acute Phase Treatment Model:

1—Ischemia Induction/reperfusion by Intraluminal Occlusion of the Middle Cerebral Artery:

Animals such as those described previously were used for this experiment. Animals were anesthetized by intraperitoneal injection of 300 mg/kg chloral hydrate. A rectal probe was inserted and body temperature was maintained at 37° C.±0.5° C. Blood pressure was monitored throughout the experiment. Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2—Treatment of Animals:

Animals first subjected to ischemia-reperfusion were treated with the inventive compounds by the oral route (such as previously described in CMC+Tween vehicle) one or more times after reperfusion (600 mg/kg/day or 300 mg/kg/day bid).

3—Measurement of Brain Infarct Volume:

24, 48 or 72 hours after reperfusion, animals previously treated or not with the compounds were euthanized by pentobarbital overdose.

Brains were rapidly frozen and sliced. Sections were stained with cresyl violet. Unstained zones of the brain sections were considered to be damaged by the infarct. Areas (of the infarct and the two hemispheres) were measured, the volume of the infarct and the two hemispheres was calculated and the corrected infarct volume was determined by the following formula: (corrected infarct volume=infarct volume−(volume of right hemisphere−volume of left hemisphere)) to compensate for cerebral oedema.

In the case of curative treatment (treatment of the acute phase), animals treated with the inventive compounds had less brain damage than untreated animals. In fact, the infarct volume was smaller when the inventive compounds were administered for 24, 48 or 72 after ischemia-reperfusion.

The inventive compounds therefore exhibit neuroprotective activity during treatment following acute ischemia.

The use of the inventive compounds in different experimental models shows that said novel compounds have intrinsic antioxidant activity, are capable of delaying and reducing the effects of an oxidative stress, and furthermore also induce the expression of genes coding for antioxidant enzymes, which together with their antioxidant property reinforces the protection against free radicals. In addition, the inventive compounds exhibit anti-inflammatory activity and are capable of activating the PPARα nuclear receptor Finally, use of the inventive compounds in an animal ischemia-reperfusion model revealed the beneficial neuroprotective effect of both preventive and curative treatment

BIBLIOGRAPHIC REFERENCES

Adams, E. P., F. P. Doyle, et al. (1960). "Antituberculous sulphur compounds. Part IV. Some dimercaptopropyl esters and related dithiouronium bromides." *J Chem Soc*: 2674-80.

Adams, H. P., Jr. (2002). "Emergent use of anticoagulation for treatment of patients with ischemic stroke." *Stroke* 33(3): 856-61.

Aebi, H. (1984). "Catalase in vitro." *Methods Enzymol* 105: 121-6.

Antoniadou-Vyzas, A., G. B. Foscolos, et al. (1986). "Diadamantane derivatives of a,o-polymethylenediamines with antimicrobial activity." *Eur J Med Chem Chim Ther* 2(1): 73-74.

Bhatia, S. K. and J. Hajdu (1987). "Stereospecific synthesis of 2-thiophosphatidylcholines; a new class of biologically active phospholipid analogues." *Tetrahedron Lett* 28(33): 3767-3770.

Bordet, R., D. Deplanque, et al. (2000). "Increase in endogenous brain superoxide dismutase as a potential mechanism of lipopolysaccharide-induced brain ischemic tolerance." *J Cereb Blood Flow Metab* 20(8): 1190-6.

Chang, R. C., P. Hudson, et al. (2000). "Influence of neurons on lipopolysaccharide-stimulated production of nitric oxide and tumor necrosis factor-alpha by cultured glia." *Brain Res* 853(2): 236-44.

Clark, R. B. (2002). "The role of PPARs in inflammation and immunity." *J Leukoc Biol* 71(3): 388-400.

Dimagl, U., C. Iadecola, et al. (1999). "Pathobiology of ischaemic stroke: an integrated view." *Trends Neurosci* 22(9): 391-7.

Farinelli, S. E., D. S. Park, et al. (1996). "Nitric oxide delays the death of trophic factor-deprived PC12 cells and sympathetic neurons by a cGMP-mediated mechanism." *J Neurosci* 16(7): 2325-34.

Flohe, L. and F. Otting (1984). "Superoxide dismutase assays." *Methods Enzymol* 105: 93-104.

Fruchart, J. C., B. Staels, et al. (2001). "PPARS, metabolic disease and atherosclerosis." *Pharmacol Res* 44(5): 345-52.

Gaffney, P. R. J. and C. B. Reese (1997). "Preparation of 2-O-arachidonoyl-1-O-stearoyl-sn-glycerol and other di-O-acyl glycerol derivatives." *Tetrahedron Lett* 38(14): 2539-2542.

Gilgun-Sherki, Y., E. Melamed, et al. (2001). "Oxidative stress induced-neurodegenerative diseases: the need for antioxidants that penetrate the blood brain barrier." *Neuropharmacology* 40(8): 959-75.

Gorelick, P. B. (2002). "Stroke prevention therapy beyond antithrombotics: unifying mechanisms in ischemic stroke pathogenesis and implications for therapy: an invited review." *Stroke* 33(3): 862-75.

Greene, L. A. and A. S. Tischler (1976). "Establishment of a noradrenergic clonal line of rat adrenal pheochromocytoma cells which respond to nerve growth factor." *Proc Natl Acad Sci USA* 73(7): 2424-8.

Gronowitz, S., B. Herslöf, et al. (1978). "Syntheses and chroptical properties of some derivatives of 1-thioglycerol." *Chem Phys Lipids* 22: 307-320.

Habig, W. H. and W. B. Jakoby (1981). "Assays for differentiation of glutathione S-transferases." *Methods Enzymol* 77: 398-405.

Jurgens, G., H. F. Hoff, et al. (1987). "Modification of human serum low density lipoprotein by oxidation—characterization and pathophysiological implications." *Chem Phys Lipids* 45(2-4): 315-36.

Kainu, T., A. C. Wikstrom, et al. (1994). "Localization of the peroxisome proliferator-activated receptor in the brain." *Neuroreport* 5(18): 2481-5.

Kitchin, J., R. C. Bethell, et al. (1994). "Synthesis and structure-activity relationships of a series of penicillin-derived HIV proteinase inhibitors: heterocyclic ring systems containing P1' and P2' substituents." *J Med Chem* 37(22): 3707-16.

Kotsovolou, S., A. Chiou, et al. (2001). "Bis-2-oxo amide triacylglycerol analogues: a novel class of potent human gastric lipase inhibitors." *J Org Chem* 66(3): 962-7.

Lebeau, J., C. Furman, et al. (2000). "Antioxidant properties of di-tert-butylhydroxylated flavonoids." *Free Radic Biol Med* 29(9): 900-12.

Lutsep, H. L. and W. M. Clark (2001). "Current status of neuroprotective agents in the treatment of acute ischemic stroke." *Curr Neurol Neurosci Rep* 1(1): 13-8.

Marx, M. H., C. Piantadosi, et al. (1988). "Synthesis and evaluation of neoplastic cell growth inhibition of 1-N-alkylamide analogues of glycero-3-phosphocholine." *J Med Chem* 31(4): 858-63.

Mates, J. M., C. Perez-Gomez, et al. (1999). "Antioxidant enzymes and human diseases." *Clin Biochem* 32(8): 595-603.

Morliere, P., A. Moysan, et al. (1991). "UVA-induced lipid peroxidation in cultured human fibroblasts." *Biochim Biophys Acta* 1084(3): 261-8.

Morris, A. D., G. Atassi, et al. (1997). "The synthesis of novel melphalan derivatives as potential antineoplastic agents." *Eur J Med Chem* 32(4): 343-50.

Murata, M., S. Ikoma, et al. (1991). "New synthesis of 2-thio-PAF and related compounds as substrates of PAF acetylhydrolase and phospholipase A2." *Chem Pharm Bull* 39(5): 1335-1336.

Nandagopal, K., T. M. Dawson, et al. (2001). "Critical role for nitric oxide signaling in cardiac and neuronal ischemic preconditioning and tolerance." *J Pharmacol Exp Ther* 297(2): 474-8.

Nazih, A., Y. Cordier, et al. (1999). "Synthesis and stability study of the new pentaammonio lipidpcTG90, a gene transfer agent." *Tetrahedron Lett* 40(46): 8089-92.

Nazih, A., Y. Cordier, et al. (2000). "One-pot transformation of a t-butyl carbamate to a bromoacetamide in the synthesis of the gene transfer agent pcTG201." *Synlett* 5: 635-6.

Paglia, D. E. and W. N. Valentine (1967). "Studies on the quantitative and qualitative characterization of erythrocyte glutathione peroxidase." *J Lab Clin Med* 70(1): 158-69.

Rahman, M. D., D. L. Ziering, et al. (1988). "Effects of sulfur-containing analogues of stearic acid on growth and fatty acid biosynthesis in the protozoan Crithidia fasciculata." *J Med Chem* 31(8): 1656-9.

Ramalingan, K., N. Raju, et al. (1995). "Synthesis of nitroimidazole substituted 3,3,9,9-tetramethyl-4,8-diazaundecane-2,10-dione dioximes (propylene amine oximes, PnAOs): ligands for technetium-99m complexes with potential for imaging hypoxic tissue." *Tetrahedron* 51(10): 2875-94.

Raspe, E., L. Madsen, et al. (1999). "Modulation of rat liver apolipoprotein gene expression and serum lipid levels by tetradecylthioacetic acid (TTA) via PPARalpha activation." *J Lipid Res* 40(11): 2099-110.

Rothwell, N. J. (1997). "Cytokines and acute neurodegeneration." *Mol Psychiatry* 2(2): 120-1.

Shealy, Y. F., J. L. Frye, et al. (1984). "Synthesis and properties of some 13-cis- and all-trans-retinamides." *J Pharm Sci* 73(6): 745-51.

Smith, K. J., E. Dipreta, et al. (2001). "Peroxisomes in dermatology. Part II." *J Cutan Med Surg* 5(4): 315-22.

Spooner, P. J., S. B. Clark, et al. (1988). "The ionization and distribution behavior of oleic acid in chylomicrons and chylomicron-like emulsion particles and the influence of serum albumin." *J Biol Chem* 263(3): 1444-53.

Spooner, R. J., A. Delides, et al. (1981). "Heat stability and kinetic properties of human serum glutathione reductase activity in various disease states." *Biochem Med* 26(2): 239-48.

Urakami, C. and K. Kakeda (1953). "Derivatives of dl-aminopropanediols." *Bull Chem Soc Jpn* 26(5): 276-278.

The invention claimed is:

1. A compound represented by general formula (I):

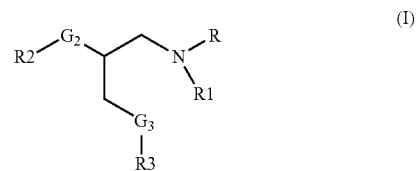

in which:

G2 and G3 independently represent an oxygen atom, a sulfur atom or a N—R4 group, wherein G2 and G3 do not simultaneously represent a N—R4 group, R and R4 independently represent a hydrogen atom or a linear or branched alkyl group, saturated or not, optionally substituted, containing from 1 to 5 carbon atoms, R1, R2 and R3, which are the same or different, represent a hydrogen atom, a CO—R5 group or a group corresponding to the formula CO—$(CH_2)_{2n+1}$—X—R6, wherein at least one of the groups R1, R2 or R3 is a group corresponding to the formula CO—$(CH_2)_{2n+1}$—X—R6, R5 is a linear or branched alkyl group, saturated or not, optionally substituted, optionally substituted by a cyclic group, the main chain of which contains from 1 to 25 carbon atoms, X is a sulfur atom, a selenium atom, a SO group or a $SO_2$ group n is a whole number comprised between 0 and 11, R6 is a linear or branched alkyl group, saturated or not, substituted or not, comprising or not a cyclic group, the main chain of which contains from 3 to 23 carbon atoms and comprising or not one or more heterogroups selected from the group consisting of an oxygen atom, a sulfur atom, a selenium atom, a SO group and a $SO_2$ group, with the exception of a compound represented by formula (I) in which G2R2 and G3R3 simultaneously represent hydroxyl groups, the optical and geometrical isomer, racemate, salt, hydrate thereof and mixtures thereof.

2. The compound according to claim 1, wherein a single one of the groups R1, R2 or R3 represents a hydrogen atom.

3. The compound according to claim 1, wherein, in the CO—$(CH_2)_{2n+1}$—X—R6 group, X represents a sulfur atom.

4. The compound according to claim 1, wherein, in the CO—$(CH_2)_{2n+1}$—X—R6 group, n is comprised between 0 and 3.

5. The compound according to claim 1, wherein R6 contains one or more heterogroups selected from the group consisting of an oxygen atom, a sulfur atom, a selenium atom, a SO group and a $SO_2$ group.

6. The compound according to claim 1, wherein CO—$(CH_2)_{2n+1}$—X—R6 is the CO—$CH_2$—S—$C_{14}H_{29}$ group.

7. The compound according to claim 1, wherein at least one of the groups R1, R2 and R3 represents a CO—$(CH_2)_{2n+1}$—X—R6 group in which X represents a sulfur atom and/or R6 is a saturated and linear alkyl group containing from 3 to 23 carbon atoms.

8. The compound according to claim 1, wherein at least two of the groups R1, R2 and R3 are CO—$(CH_2)_{2n+1}$—X—R6 groups, which are the same or different, in which X represents a sulfur atom.

9. The compound according to claim 1, wherein G2 represents an oxygen atom.

10. The compound according to claim 1, wherein G2 represents an oxygen or sulfur atom and R2 represents a group corresponding to the formula CO—$(CH_2)_{2n+1}$—X—R6.

11. The compound according to claim 1, wherein:
G3 is a N—R4 group in which R4 is a hydrogen atom or a methyl group, and G2 is an oxygen atom; and/or
R2 represents a CO—$(CH_2)_{2n+1}$—X—R6 group.

12. The compound according to claim 1, wherein R1, R2 and R3, which are the same or different, represent a CO—$(CH_2)_{2n+1}$—X—R6 group, in which X represents a sulfur atom and/or R6 is a saturated and linear alkyl group containing from 13 to 17 carbon atoms in which n is comprised between 0 and 3.

13. The compound according to claim 1, selected from the group consisting of:
1-tetradecylthioacetylamino-2,3-(dipalmitoyloxy)propane;
3-tetradecylthioacetylamino-1,2-(ditetradecylthioacetyloxy)propane;
3-palmitoylamino-1,2-(ditetradecylthioacetyloxy)propane;
1,3-di(tetradecylthioacetylamino)propan-2-ol;
1,3-diamino-2-(tetradecylthioacetyloxy)propane;
1,3-ditetradecylthioacetylamino-2-(tetradecylthioacetyloxy)propane;
1,3-dioleoylamino-2-(tetradecylthioacetyloxy)propane;
1,3-ditetradecylthioacetylamino-2-(tetradecylthioacetythio)propane; and
1-tetradecylthioacetylamino-2,3-di(tetradecylthioacetylthio)propane.

14. A pharmaceutical composition comprising, in a pharmaceutically acceptable excipient or vehicle, at least one compound represented by formula (I) defined in any of the previous claims.

15. The pharmaceutical composition according to claim 14, for the treatment or prophylaxis of cerebrovascular pathologies.

16. A method for the treatment of cerebral ischemia comprising administering to a subject in need of such treatment an effective amount of a compound represented by general formula (I):

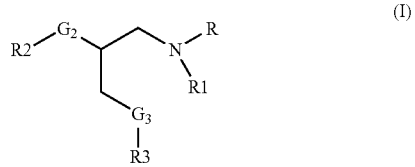

in which:
G2 and G3 independently represent an oxygen atom, a sulfur atom or a N—R4 group, wherein G2 and G3 do not simultaneously represent a N—R4 group,
R and R4 independently represent a hydrogen atom or a linear or branched alkyl group, saturated or not, optionally substituted, containing from 1 to 5 carbon atoms,
R1, R2 and R3, which are the same or different, represent a hydrogen atom, a CO—R5 group or a group corresponding to the formula CO—$(CH_2)_{2n+1}$—X—R6, wherein at least one of the groups R1, R2 or R3 is a group corresponding to the formula CO—$(CH_2)_{2n+1}$—X—R6, R5 is a linear or branched alkyl group, saturated or not, optionally substituted, optionally substituted by a cyclic group, the main chain of which contains from 1 to 25 carbon atoms,
X is a sulfur atom, a selenium atom, a SO group or a $SO_2$ group
n is a whole number comprised between 0 and 11,
R6 is a linear or branched alkyl group, saturated or not, substituted or not, comprising or not a cyclic group, the main chain of which contains from 3 to 23 carbon atoms and comprising or not one or more heterogroups selected from the group consisting of an oxygen atom, a sulfur atom, a selenium atom, a SO group and a $SO_2$ group,
the optical and geometrical isomer, racemate, salt, hydrate thereof and mixtures thereof.

17. The compound according to claim 1, wherein R6 is a linear or branched alkyl group, saturated or not, substituted or not, comprising or not a cyclic group, the main chain of which contains from 10 to 23 carbon atoms and comprising or not one or more heterogroups selected from the group consisting of an oxygen atom, a sulfur atom, a selenium atom, a SO group and a $SO_2$ group.

18. The compound according to claim 1, wherein, in the CO—$(CH_2)_{2n+1}$—X—R6 group, X represents a selenium atom.

19. The compound according to claim 1, wherein in the CO—$(CH_2)_{2n+1}$—X—R6 group, n is comprised between 0 and 2.

20. The compound according to claim 1, wherein in the CO—$(CH_2)_{2n+1}$—X—R6 group, n is equal to 0.

21. The compound according to claim 1, wherein R6 contains 0, 1 or 2 heterogroups selected from the group consisting of an oxygen atom, a sulfur atom, a selenium atom, a SO group and a $SO_2$ group.

22. The compound according to claim 1, wherein R6 contains 0 or 1 heterogroup selected from the group consisting of an oxygen atom, a sulfur atom, a selenium atom, a SO group and a $SO_2$ group.

23. The compound according to claim 1, wherein at least one of the groups R1, R2 and R3 represents a CO—$(CH_2)_{2n+1}$—X—R6 group in which X represents a sulfur atom and/or R6 is a saturated and linear alkyl group containing from 13 to 20 carbon atoms.

24. The compound according to claim 1, wherein at least one of the groups R1, R2 and R3 represents a CO—$(CH_2)_{2n+1}$—X—R6 group in which X represents a sulfur atom and/or R6 is a saturated and linear alkyl group containing from 14 to 17 carbon atoms.

25. The compound according to claim 1, wherein at least one of the groups R1, R2 and R3 represents a CO—$(CH_2)_{2n+1}$—X—R6 group in which X represents a sulfur atom and/or R6 is a saturated and linear alkyl group containing 14 carbon atoms.

26. The compound according to claim 1, wherein G2 represents a sulfur atom.

27. The compound according to claim 1, wherein , R2 and R3, which are the same or different, represent a CO—$(CH_2)_{2n+1}$—X—R6 group, in which X represents a sulfur atom and/or R6 is a saturated and linear alkyl group containing 14 carbon atoms and n is comprised between 0 and 3.

28. The compound according to claim 1, wherein R1, R2 and R3, which are the same or different, represent a CO—$(CH_2)_{2n+1}$—X—R6 group, in which X represents a sulfur atom and/or R6 is a saturated and linear alkyl group containing 14 carbon atoms and n is equal to 0.

29. The compound according to claim 1, wherein R1, R2 and R3, which are the same, represent a CO—$(CH_2)_{2n+1}$—X—R6 group, in which X represents a sulfur atom and/or R6 is a saturated and linear alkyl group containing from 13 to 17 carbon atoms and n is comprised between 0 and 3.

30. The compound according to claim 1, wherein R1, R2 and R3, which are the same, represent a CO—$(CH_2)_{2n+1}$—X—R6 group, in which X represents a sulfur atom and/or R6 is a saturated and linear alkyl group containing 14 carbon atoms and n is comprised between 0 and 3.

31. The compound according to claim 1, wherein R1, R2 and R3, which are the same, represent a CO—$(CH_2)_{2n+1}$—X—R6 group, in which X represents a sulfur atom and/or R6 is a saturated and linear alkyl group containing from 13 to 17 carbon atoms and n is equal to 0.

32. The compound according to claim 1, wherein R1, R2 and R3 represent CO—$CH_2$—S—$C_{14}H_{29}$ groups.

33. The pharmaceutical composition according to claim 14, for the treatment or prophylaxis of cerebral ischemia or stroke.

* * * * *

UNITED STATES PATENT AND TRADEMARK OFFICE
CERTIFICATE OF CORRECTION

| | | |
|---|---|---|
| PATENT NO. | : 7,253,296 B2 | Page 1 of 1 |
| APPLICATION NO. | : 10/541225 | |
| DATED | : August 7, 2007 | |
| INVENTOR(S) | : Darteil et al. | |

It is certified that error appears in the above-identified patent and that said Letters Patent is hereby corrected as shown below:

On the Title Page, delete the following:

Item "(*) Notice: Subject to any disclaimer the term of this patent is extended or adjusted under 35 U.S.C. 154(b) by 0 days."

and insert the following therefor:

Item --(*) Notice: Subject to any disclaimer the term of this patent is extended or adjusted under 35 U.S.C. 154(b) by 0 days.

This patent is subject to a terminal disclaimer.--

Signed and Sealed this

Eighth Day of July, 2008

JON W. DUDAS
*Director of the United States Patent and Trademark Office*